United States Patent
Nishio et al.

(10) Patent No.: US 10,052,590 B2
(45) Date of Patent: Aug. 21, 2018

(54) FILTER DEVICE, MANUFACTURING DEVICE FOR CHEMICAL, AND OPERATION METHOD FOR FILTER DEVICE

(71) Applicant: TORAY INDUSTRIES, INC., Tokyo (JP)

(72) Inventors: Aya Nishio, Shiga (JP); Norihiro Takeuchi, Shiga (JP); Atsushi Kobayashi, Shiga (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/900,051

(22) PCT Filed: Jun. 20, 2014

(86) PCT No.: PCT/JP2014/066481
§ 371 (c)(1),
(2) Date: Dec. 18, 2015

(87) PCT Pub. No.: WO2014/204002
PCT Pub. Date: Dec. 24, 2014

(65) Prior Publication Data
US 2016/0144320 A1  May 26, 2016

(30) Foreign Application Priority Data
Jun. 21, 2013 (JP) ................. 2013-130368

(51) Int. Cl.
*B01D 21/24* (2006.01)
*B01D 61/58* (2006.01)
(Continued)

(52) U.S. Cl.
CPC ............ *B01D 61/58* (2013.01); *B01D 61/08* (2013.01); *B01D 61/147* (2013.01); *B01D 61/18* (2013.01);
(Continued)

(58) Field of Classification Search
None
See application file for complete search history.

(56) References Cited

U.S. PATENT DOCUMENTS

| 4,545,940 A | 10/1985 | Mutoh et al. |
| 5,182,023 A * | 1/1993 | O'Connor ............... C02F 1/441 210/650 |
| 2013/0280773 A1 | 10/2013 | Takeuchi et al. |

FOREIGN PATENT DOCUMENTS

| CN | 1311055 A | 9/2001 |
| CN | 102847368 A | 1/2013 |

(Continued)

OTHER PUBLICATIONS

International Search Report, issued in PCT/JP2014/066481, dated Sep. 22, 2014.
(Continued)

*Primary Examiner* — Richard C Gurtowski
(74) *Attorney, Agent, or Firm* — Birch, Stewart, Kolasch & Birch, LLP

(57) ABSTRACT

In order to efficiently transport a filtration target liquid to a separation membrane module and to facilitate additional simplification of equipment in a filtration device including the separation membrane modules in which a plurality of lines thereof are disposed in series, a filtration device according to the present invention is a filtration device including a plurality of separation membrane modules each of which separates a liquid to be filtrated into a permeated liquid and a non-permeated liquid, in which the filtration device includes: a series non-permeated liquid flow channel that forms a series unit by connecting non-permeation sides of the plurality of separation membrane modules in series; and a parallel permeated liquid flow channel that forms a
(Continued)

parallel unit by connecting permeation sides of the plurality of separation membrane modules in parallel.

13 Claims, 18 Drawing Sheets

(51) Int. Cl.
*B01D 61/22* (2006.01)
*B01D 65/02* (2006.01)
*B01D 61/14* (2006.01)
*B01D 61/18* (2006.01)
*B01D 63/02* (2006.01)
*B01D 63/04* (2006.01)
*B01D 61/08* (2006.01)
*C12M 1/00* (2006.01)

(52) U.S. Cl.
CPC ............ *B01D 61/22* (2013.01); *B01D 63/02* (2013.01); *B01D 63/04* (2013.01); *B01D 65/02* (2013.01); *C12M 29/04* (2013.01); *B01D 2311/14* (2013.01); *B01D 2311/16* (2013.01); *B01D 2315/10* (2013.01); *B01D 2315/12* (2013.01); *B01D 2317/022* (2013.01); *B01D 2317/04* (2013.01); *B01D 2321/04* (2013.01); *B01D 2321/16* (2013.01)

(56) References Cited

FOREIGN PATENT DOCUMENTS

| | | |
|---|---|---|
| EP | 2308586 A1 | 4/2011 |
| JP | 54-6873 A | 1/1979 |
| JP | 10-156156 A | 6/1998 |
| JP | 2008-237101 A | 10/2008 |
| JP | 2009-72708 A | 4/2009 |
| WO | WO 2012/086720 A | 6/2012 |

OTHER PUBLICATIONS

Written Opinion of the International Searching Authority, issued in PCT/JP2014/066481, dated Sep. 22, 2014.
Chinese Office Action and Search Report for Chinese Application No. 201480035402.3, dated Aug. 31, 2016, with a partial English translation of the Office Action only.
Extended European Search Report issued in European Application No. 14813317.6 dated Apr. 5, 2017.
Chinese Office Action and Search Report, dated May 27, 2017, for Chinese Application No. 201480035402.3, as well as an Partial English translation.
Chinese Office Action, dated Nov. 27, 2017, for Chinese Application No. 201480035402.3, along with an English translation.

\* cited by examiner

FILTER DEVICE, MANUFACTURING DEVICE FOR CHEMICAL, AND OPERATION METHOD FOR FILTER DEVICE

TECHNICAL FIELD

The present invention relates to a filtration device including separation membrane modules in which a plurality of lines thereof are disposed in series, a chemical manufacturing apparatus utilizing the filtration device, and a method for operating a filtration device.

BACKGROUND ART

Separation membranes are utilized in various fields, for example, the field of water treatment such as manufacturing of drinking water, water purification processing, and effluent treatment; the field of fermentation in which production of substances accompanied with cultivation of microorganisms or cultured cells is carried out; and the field of the food industry. In the field of water treatment such as manufacturing of drinking water, water purification processing, and effluent treatment, the separation membranes are used so as to eliminate impurities in the water, as substitutions of the sand filtration and the coagulation settling process in the background art.

There are various types of separation membrane modules, and the generally known technology uses hollow fiber membrane modules in which an installation area per membrane area is small and replacement cost for the separation membrane modules is inexpensive. As a filtration method, there are (1) a total amount filtration method in which filtration is performed by supplying a filtration target liquid to the separation membrane modules, and (2) a cross-flow filtration method in which a filtration target liquid is supplied to the separation membrane modules, a portion thereof is filtrated, and most of other portions thereof are caused to circulate to a storage tank or the like of the filtration target liquid. In the cross-flow filtration, an effect of removing sediments on a separation membrane surface by the shearing force of a stream of cross-flow which is parallel to separation membranes can be expected. Therefore, the cross-flow filtration is preferably used when processing a target liquid having high turbidity concentration.

As an application example of filtration technology using the separation membranes, a continuous fermentation method can be exemplified. In other words, according to the continuous fermentation method, it is proposed that microorganisms or cultured cells are filtrated through the separation membranes, thereby collecting a chemical from a filtrated liquid, and at the same time, retaining the microorganisms or the cultured cells in a fermentation cultured liquid or refluxing the microorganisms or the cultured cells in a concentrated liquid to the fermentation cultured liquid. In accordance with the method, the concentration of microorganisms or cultured cells in the fermentation cultured liquid can be maintained to be high.

With regard to a continuous-fermentation apparatus, a technology has been disclosed in order to perform the production through more efficient continuous-fermentation. The technology uses hollow fiber membrane modules in which an installation area per membrane area is small and replacement cost for the separation membrane modules is inexpensive (refer to Patent Document 1). According to the technology using the hollow fiber membranes as separation membranes, the concentration of microorganisms or cultured cells in the fermentation cultured liquid can be maintained to be high by collecting a chemical from a filtrated liquid, and at the same time, retaining the microorganisms or the cultured cells in a fermentation cultured liquid or refluxing the microorganisms or the cultured cells in a concentrated liquid to the fermentation cultured liquid. The technology employs cross-flow filtration in which a fermentation cultured liquid is supplied to the hollow fiber membrane modules, a portion thereof is filtrated, and most of other portions thereof are refluxed to a fermentor. Contaminants on a membrane surface can be removed by the shearing force of a stream of cross-flow, and thus, efficient filtration can be continued for a long period of time.

Here, in continuous fermentation which is carried out on the industrial scale, a large fermentor is used, and volume thereof is assumed to be several hundred $m^3$. A significant membrane area is necessary in order to perform filtration with a fermentation liquid in large quantity including highly concentrated microorganisms. In order to realize the significant membrane area, it is effective to use a plurality of the separation membrane modules with respect to one fermentor. For example, when a fermentation liquid of hundred $m^3$ is filtrated, hundreds or thousands of the plurality of separation membrane modules are used at most. However, the most suitable number of the separation membrane modules may vary depending on filtration properties of the fermentation liquid and performance of the separation membrane modules.

According to Patent Document 2, cross-flow filtration is employed in order to obtain an effect of cleaning the separation membranes. From a view point of reduction of operational cost, the separation membrane modules are disposed in series so that the flow rate of cross-flow can be reduced (Patent Document 2).

Since a large amount of water is processed also in the field of water treatment such as manufacturing of drinking water, water purification processing, and effluent treatment, many separation membrane modules are used. There is a disclosed technology in which the separation membrane modules for cross-flow filtration are disposed in series so as to reduce the used amount of a raw liquid and the processing amount of waste liquid when flushing cleaning is performed by causing the raw liquid to flow outside the hollow fiber membranes (Patent Document 3).

BACKGROUND ART DOCUMENT

Patent Document

Patent Document 1: JP-A-2008-237101
Patent Document 2: WO 2012/086720
Patent Document 3: JP-A-2009-72708

SUMMARY OF THE INVENTION

Problems that the Invention is to Solve

When a plurality of separation membrane modules are applied to cross-flow filtration, as the number of the separation membrane modules increases, the total volume of a flow rate of cross-flow supplied to each of the modules increases, thereby resulting in an increased power cost for a cross-flow liquid supply pump. Moreover, the diameter of the cross-flow liquid supply pipe increases, and cost of equipment including measuring gauges also increases.

When the modules are disposed in series, the total amount of the flow rate of cross-flow can be reduced as compared to a case of being disposed in parallel, and it is considered to be able to prevent the liquid supply equipment from being increased in size. However, the equipment is required to be simplified further. Therefore, an object of the present invention is to provide a technology which can cope with such demands.

Means for Solving the Problems

In order to solve the aforementioned problems, the present invention includes any one of the configurations described below.

(1) A filtration device including a plurality of separation membrane modules each of which separates a liquid to be filtrated into a permeated liquid and a non-permeated liquid,
in which the filtration device includes:
a series non-permeated liquid flow channel that forms a series unit by connecting non-permeation sides of the plurality of separation membrane modules in series; and
a parallel permeated liquid flow channel that forms a parallel unit by connecting permeation sides of the plurality of separation membrane modules in parallel.

(2) A filtration device including a plurality of separation membrane modules each of which separates a liquid to be filtrated into a permeated liquid and a non-permeated liquid,
in which the filtration device includes:
a series non-permeated liquid flow channel that forms a series unit by connecting non-permeation sides of the plurality of separation membrane modules in series; and
a filtrating operation control device that controls at least one of a filtration flow rate and a transmembrane pressure difference of the separation membrane modules by collectively controlling pressures of the permeated liquids flowing out from the plurality of separation membrane modules.

(3) The filtration device according to (2), in which the filtrating operation control device collectively controls the pressures of the permeated liquids flowing out from the plurality of separation membrane modules which are included in the series units different from one another and are disposed in a same stage.

(4) The filtration device according to (2) or (3), further including:
a unit-crossing parallel flow channel that forms a parallel unit by connecting permeation sides of the plurality of separation membrane modules belonging to the series units different from one another in parallel,
in which the filtrating operation control device is disposed on the unit-crossing parallel flow channel and controls at least one of the filtration flow rate and the transmembrane pressure difference of the separation membrane modules by collectively controlling the pressures of the permeated liquids flowing out from the plurality of separation membrane modules belonging to the same parallel unit.

(5) The filtration device according to (1), including, as the parallel permeated liquid flow channel, at least a unit-crossing parallel flow channel that connects the plurality of separation membrane modules belonging to the series units different from one another,
in which the filtration device further includes a filtrating operation control device that controls at least one of a filtration flow rate and a transmembrane pressure difference of the separation membrane modules by collectively controlling pressures of the permeated liquids flowing out from the plurality of separation membrane modules belonging to the same parallel unit and that is disposed on the unit-crossing parallel flow channel (6) The filtration device according to (4) or (5), including, as the parallel unit, at least a first parallel unit and a second parallel unit that is disposed in a later stage than the separation membrane modules included in the first parallel unit.

(7) The filtration device according to any of (4) to (6), in which the filtrating operation control device controls the pressures of the permeated liquids flowing out from the separation membrane modules so as to reduce a difference in the filtration flow rate between the separation membrane modules belonging to the parallel units different from one another.

(8) The filtration device according to any of (4) to (6), in which the filtrating operation control device controls the pressures of the permeated liquids flowing out from the separation membrane modules so as to reduce a difference in the transmembrane pressure difference between the separation membrane modules belonging to the parallel units different from one another.

(9) The filtration device according to (5), further including a cleaning liquid supply unit that is connected to the parallel permeated liquid flow channel and supplies a cleaning liquid for backwashing.

(10) The filtration device according to any of (2) to (9), including a plurality of the filtrating operation control devices.

(11) The filtration device according to any of (1) to (10), in which a longitudinal direction of the separation membrane module is perpendicular to or inclined with respect to a horizontal direction.

(12) A chemical manufacturing apparatus including:
a fermentor that accommodates a fermentation liquid including a raw material and a cell which causes the raw material to ferment, thereby producing a chemical;
the filtration device according to any of (1) to (11), which is connected to the fermentor and which performs filtration using the separation membrane modules so as to separate the fermentation liquid into a non-permeated liquid containing the cell, and a permeated liquid containing the chemical; and
a flow channel through which the non-permeated liquid is refluxed to the fermentor.

(13) A method for operating a filtration device which includes a plurality of series units having two or more stages of separation membrane modules which are connected in series via each entrance thereof for a liquid to be filtrated, the method including:
a step (a) of performing filtration in which the liquid to be filtrated is separated into a permeated liquid and a non-permeated liquid using the separation membrane modules;
a step (b) of controlling at least one of a filtration flow rate and a transmembrane pressure difference of the separation membrane modules by collectively controlling pressures of the permeated liquids flowing out from a plurality of the separation membrane modules included in the series units different from one another; and
a step (c) of performing intermittent filtration in which execution of filtration and suspension of the filtration are alternately repeated,
in which the step (c) includes the intermittent filtration which is collectively performed with respect to the plurality of the separation membrane modules in which the pressures of the permeated liquids are collectively controlled through the step (b).

(14) The method for operating a filtration device according to (13), further including:

a step (d) of performing backwashing of the separation membrane module which is under suspension of the filtration.

(15) The method for operating a filtration device according to (13) or (14), in which the step (a) includes:

a step (a1) of suspending the filtration of a part of the separation membrane modules; and a step (a2) of executing the filtration of the separation membrane modules other than the separation membrane modules of which filtration is suspended through the step (a1).

Advantage of the Invention

According to the present invention, in a filtration device, equipment can be shared among a plurality of separation membrane modules by mutually connecting exits for a permeated liquid of the plurality of separation membrane modules or providing, in the filtration device, a filtrating operation control device to collectively control pressures of the permeated liquids discharged from the plurality of separation membrane modules. Therefore, according to the present invention, a flow rate of cross-flow can be reduced by disposing the separation membrane modules in series, and also the equipment can be simplified.

MODE FOR CARRYING OUT THE INVENTION

The present invention can be applied when using a plurality of separation membrane modules in various fields, for example, the field of water treatment such as manufacturing of drinking water, water purification processing, and effluent treatment; the field of fermentation in which production of substances accompanied with cultivation of microorganisms or cultured cells is carried out; and the field of the food industry. Herein, descriptions will be given by exemplifying embodiments of a continuous-fermentation apparatus.

I. Chemical Manufacturing Apparatus

The embodiments of the present invention will be described by exemplifying the continuous-fermentation apparatus with reference to the drawings. The below-described continuous-fermentation apparatus is an example of an apparatus for executing a method for manufacturing a chemical described below. Therefore, descriptions regarding the configuration to be mentioned in the section of the manufacturing method as a configuration of the apparatus for executing the manufacturing method may be omitted.

Figure 1:
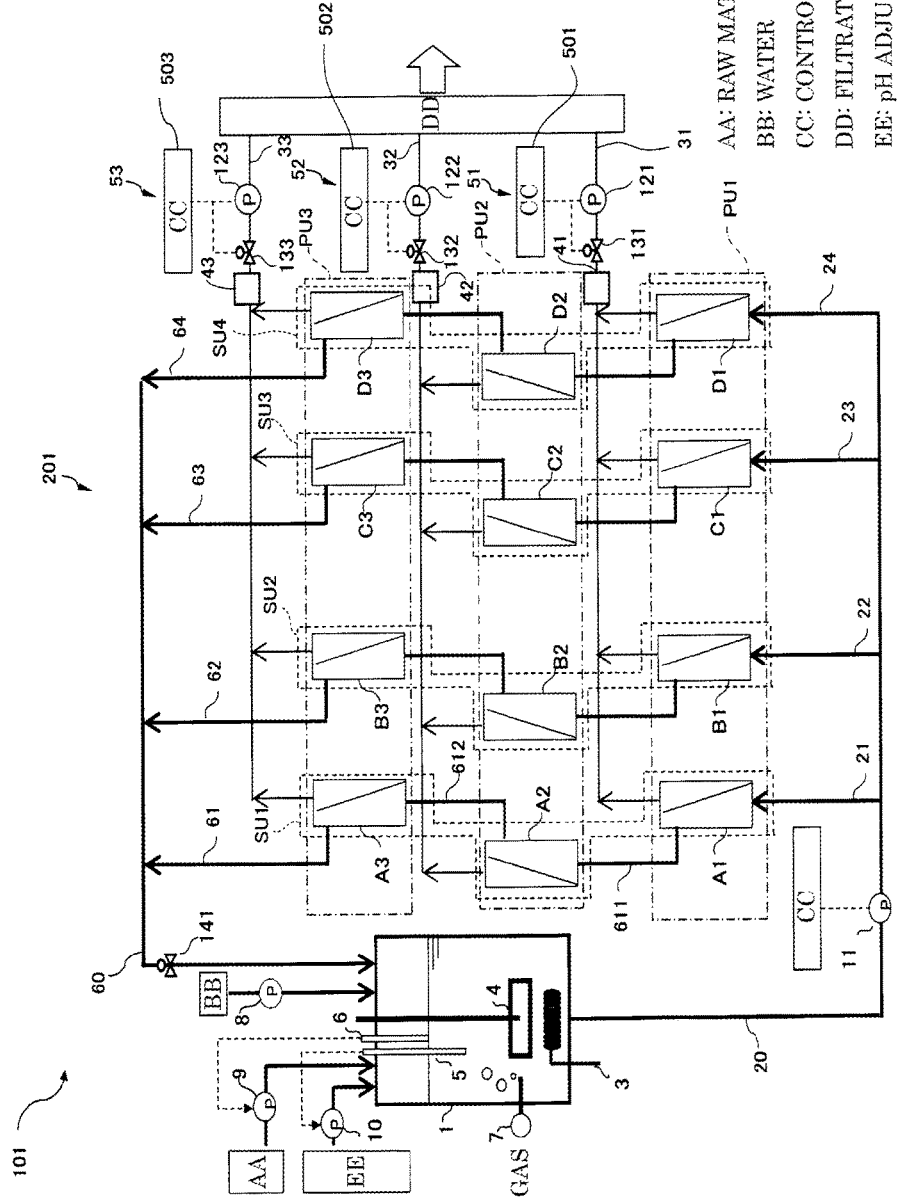
FIG. 1 is a schematic diagram of a continuous-fermentation apparatus according to a first embodiment of the present invention.

(1) First Embodiment (1-1) Overall Configuration of Chemical Manufacturing Apparatus FIG. 1 is a schematic diagram of the continuous-fermentation apparatus according to a first embodiment. A continuous-fermentation apparatus 101 (hereinafter, may be simply referred to as "the fermentation apparatus") according to the first embodiment includes a fermentor 1, a temperature control device 3, an agitation device 4, a pH sensor 5, a level sensor 6, a gas supply device 7, a water supply pump 8, a culture medium supply pump 9, and a pH adjuster supply pump 10. The fermentation apparatus 101 further includes a filtration device 201. The fermentor 1 and the filtration device 201 are connected to each other by a liquid supply line (a liquid supply flow channel) 20 through which a fermentation liquid in the fermentor is supplied to the filtration device 201, and a reflux line (a reflux flow channel) 60 through which a circulating liquid is returned to the fermentor 1 from the filtration device 201.

The fermentation liquid is supplied to the separation membrane module as a liquid to be filtrated, thereby being separated into a non-permeated liquid and a permeated liquid. In this Description, inside the continuous-fermentation apparatus, among the flow channels through which the liquid to be filtrated, the non-permeated liquid and the permeated liquid, respectively flow and a space inside the separation membrane module, a side for the non-permeated liquid will be referred to as "the non-permeation side" and a side for the permeated liquid will be referred to as "the permeation side" while taking a separation membrane inside the separation membrane module as a boundary.

Cells and a raw material are incorporated into the fermentor 1. Inside the fermentor 1, as fermentation progresses due to the cells, the raw material is converted into a fermentation liquid containing a chemical. Cells and fermentation will be described later in detail.

The temperature control device 3 includes a temperature sensor, a heating unit, a cooling unit, and a control unit. The temperature control device 3 causes the control unit to control operations of the heating unit and the cooling unit based on a temperature inside the fermentor 1 detected by the temperature sensor so as to have the temperature which indicates a value within a predetermined range. In this manner, since the temperature of the fermentor 1 is uniformly maintained, high cell concentration is maintained.

The agitation device 4 agitates the fermentation liquid inside the fermentor 1.

The pH sensor 5 detects a pH value of the fermentation liquid inside the fermentor 1. A pH control unit (not illustrated) controls an operation of the pH adjuster supply pump 10 based on a detection result of the pH sensor 5 so that the pH value of the fermentation liquid inside the fermentor 1 is retained within a predetermined range. The pH adjuster supply pump 10 is connected to a pH adjuster tank and supplies a pH adjuster to the fermentor 1. An alkaline solution or an acid solution serving as the pH adjuster is stored in the pH adjuster tank. The pH adjuster supply pump 10 may be connected to two or more pH adjuster tanks. In such a case, the alkaline solution and the acid solution are individually stored in the pH adjuster tanks.

The level sensor 6 detects a liquid level in the fermentor 1. A level control unit (not illustrated) controls operation of mechanisms such as the water supply pump 8 and the culture medium supply pump 9 which supply a liquid to the fermentor 1, based on a detection result of the level sensor 6 so as to maintain the liquid level inside the fermentor 1 to be within a predetermined range.

The gas supply device 7 supplies gas to the fermentor 1 via a gas supply port. The gas supply port may be disposed so as to supply gas directly to the fermentor 1 or may be disposed so as to supply gas to a line through which the fermentation liquid is supplied to the separation membrane module, or the separation membrane module. As gas is supplied to the line or the separation membrane module, oxygen can be dissolved in the fermentation liquid, and at the same time, cells and the like sedimented on a separation membrane surface can be removed by the shearing force of the gas.

When providing the gas supply port at a position where gas is supplied to the liquid supply line or the separation membrane module, the gas supply port may be provided at a lower portion of the separation membrane module. Otherwise, the gas supply port may be provided in a pipe (that is, the flow channel) through which the fermentor 1 and the separation membrane module communicate with each other. When supplying the fermentation liquid from the fermentor 1 to the separation membrane module by using a circulation pump 11, the gas supply port can be provided between the fermentation liquid and the circulation pump 11, or between the circulation pump 11 and the separation membrane module disposed on the foremost stage.

If the gas supply line is installed for each of series units described below, gas can be individually supplied to each of the series units. Moreover, gas can be intermittently supplied, and the consumption amount of gas can be controlled.

When aerobic fermentation is performed in the fermentor 1, it is preferable that gas supplied by the gas supply device 7 includes oxygen. The gas including oxygen may be pure oxygen or may be gas which causes no adverse influence on fermentation, for example, air, nitrogen, carbon dioxide, methane, or gas of which oxygen concentration is adjusted by mixing mixed gas and the like of the aforementioned gases with oxygen. When anaerobic fermentation is performed in the fermentor 1, if the supply rate of oxygen needs to be reduced, the gas supply device 7 can supply gas obtained by mixing gas which includes no oxygen, such as carbon dioxide, nitrogen, methane, and argon, with air.

A gas supply source may be an apparatus which can supply gas at uniform pressure after compressing the gas. Otherwise, the gas supply source may be a tank in which gas is compressed and gas can be supplied at uniform pressure. It is possible to use compressed gas or the like which is supplied by a gas cylinder, a blower, a compressor, or a pipe.

The water supply pump 8 supplies water directly to the fermentor 1. Water can be supplied indirectly to the fermentor 1 through supplying of a raw material, adding of the pH adjuster, and the like. Water may be supplied indirectly to the fermentor 1 by supplying water from the permeation side to the non-permeation side of the separation membrane module. As water is supplied from the permeation side to the non-permeation side of the separation membrane module, water is supplied to the fermentor 1, and at the same time, cells and the like sedimented on the separation membrane surface can be removed.

In order to prevent contamination caused by contaminants and to efficiently perform fermentation, it is preferable that a substance to be added to the continuous-fermentation apparatus is sterilized. For example, a culture medium to be used as a raw material may be sterilized by being heated after an adjustment. Water to be added to the culture medium, the pH adjuster and the fermentor may be caused to pass through a sterilization filter as necessary so as to be in an aseptic condition.

(1-2) Filtration Device

The filtration device 201 mainly includes a plurality of separation membrane modules A1, A2, A3, B1, B2, B3, C1, C2, C3, D1, D2 and D3; the circulation pump 11; and filtrating operation control devices (the control units) 51, 52 and 53.

(A) Overview of Separation Membrane Module

The separation membrane module is acceptable as long as the module can separate a filtrated liquid (that is, the permeated liquid) from the liquid to be filtrated, and the structure thereof is not limited to specific examples described in this Description.

The separation membrane module includes a casing; the separation membrane which is accommodated inside the casing and separates the liquid to be filtrated into the permeated liquid and the non-permeated liquid; an entrance for the liquid to be filtrated through which the liquid to be filtrated is supplied to the separation membrane from the outside of the casing; an exit for the permeated liquid through which the permeated liquid is discharged to the outside of the casing; and an exit for the non-permeated liquid through which the non-permeated liquid is discharged to the outside of the casing. It is preferable that the entrance for the liquid to be filtrated and the exit for the permeated liquid are respectively provided in the vicinity of both ends of the casing in a longitudinal direction. The longitudinal direction of the casing can be interpreted as the longitudinal direction of the separation membrane module. The non-permeated liquid is returned to the fermentor 1 as a circulation liquid. The structure will be described later in more detail.

(B) Disposition of Separation Membrane Module

In the present embodiment, the separation membrane modules A1, A2, and A3 are arranged in this order from the upstream side in a flowing direction of the fermentation liquid. The non-permeation sides of the separation membrane modules A1, A2, and A3 are connected in series. In other words, the separation membrane modules A1, A2, and A3 form a first series unit SU1. The separation membrane modules A1, A2, and A3 are respectively disposed in the first stage, the second stage, and the third stage in one series unit SU1.

The expression "the non-permeation sides of the separation membrane modules are connected in series" denotes that the two modules are connected to each other so as to cause a non-permeated liquid obtained from a liquid to be filtrated which is supplied to a certain separation membrane module, to be supplied to a different separation membrane module as a liquid to be filtrated.

Specifically, the exit for the non-permeated liquid of the separation membrane module A1 and the entrance for the liquid to be filtrated of the separation membrane module A2 in a later stage thereof are connected to each other with a series non-permeated liquid flow channel 611, and the exit for the non-permeated liquid of the separation membrane module A2 and the entrance for the liquid to be filtrated of the separation membrane module A3 in a later stage thereof are connected to each other with a series non-permeated liquid flow channel 612.

Similarly, the separation membrane modules B1, B2, and B3 form a second series unit SU2 by connecting the non-permeation sides thereof in series. The separation membrane modules C1, C2, and C3 also form a third series unit SU3 by connecting the non-permeation sides thereof in series. Moreover, the separation membrane modules D1, D2, and D3 form a fourth series unit SU4 by connecting the non-permeation sides thereof in series. Similar to the first series unit, the separation membrane modules inside the second, third, and fourth series units are also connected to the series non-permeated liquid flow channel. The series non-permeated liquid flow channels of the units will be illustrated but the reference numerals and signs will be omitted due to circumstances of blank space.

According to the configuration of such a series unit, the non-permeated liquid obtained from modules in a fore stage is supplied to modules in a later stage as the liquid to be filtrated. In this Description, liquids inside the filtration device, such as a fermentation liquid which enters into none of the separation membrane modules, a non-permeated liquid which flows out from a certain separation membrane module before arriving at a subsequent separation membrane module, and a non-permeated liquid which flows out from the separation membrane module in the lattermost stage may be collectively referred to as "the circulation liquid". The circulation liquid may also be referred to as "the cross-flow".

In this Description, "the stage" such as the first stage and the second stage, represents the order of the modules which are arranged along the flowing direction of the fermentation liquid supplied from the fermentor 1. Accordingly, in the first series unit SU1, the module A1 on the uppermost stream side is the module in the first stage, and the module A2 next thereto is the module in the second stage.

In the series unit, it is preferable that the modules in a fore stage (on the upstream side) are disposed at positions lower than the modules in a later stage (on the downstream side). The expression "the modules in a fore stage are disposed at positions lower than the modules in a later stage" specifically indicates that upper portions of the modules in a fore stage are disposed at positions lower than lower portions of the modules in a later stage, or the exits for the non-permeated liquid of the modules in a fore stage are disposed at positions lower than the entrances for the liquid to be filtrated of the modules in a later stage.

Modules which belong to the same series unit do not need to be arranged along a vertical direction. In other words, modules in a later stage may be disposed obliquely above the modules in a fore stage.

In the configuration of FIG. 1, each of the separation membrane modules is disposed so as to cause the entrance for the liquid to be filtrated to be at the bottom and to cause the exit for the non-permeated liquid to be at the top. In other words, the circulation liquid goes up from the bottom to the top of each separation membrane module, thereby being supplied to another separation membrane module which is disposed at a position further upward. Namely, the fermentation liquid is supplied to the separation membrane module A1 from the entrance for the liquid to be filtrated which is positioned at a lower portion of the separation membrane module A1. The non-permeated liquid which has not permeated the separation membrane of the separation membrane module A1 advances upward inside the separation membrane module A1, thereby being supplied from the exit for the non-permeated liquid which is positioned at an upper portion of the module A1 to the entrance for the liquid to be filtrated which is positioned at a lower portion of the separation membrane module A2. The non-permeated liquid sequentially ascending inside the modules A2 and A3 is eventually refluxed to the fermentor from the exit for the non-permeated liquid of the separation membrane module A3 in the uppermost stage.

The first to fourth series units (the first to fourth separation membrane module series units) (SU1 to SU4) are also connected in parallel. In other words, the pipes through which the fermentation liquid comes out from the fermentor 1, that is, four pipes (the pipes for the liquid to be filtrated) 21, 22, 23, and 24 are branched from the liquid supply line 20, and the four pipes are respectively connected to the entrances for the liquid to be filtrated of the separation membrane modules in the first stage of four series units. Then, four pipes (the circulation liquid pipes) 61, 62, 63, and 64 through which the circulation liquid comes out from each of the separation membrane modules in the lattermost stage of the first to fourth series units (SU1 to SU4) are connected to one pipe through which the circulation liquid is returned to the fermentor 1, that is, are connected to the reflux line 60. A valve 141 is disposed on the reflux line 60.

Moreover, in different series units, the permeation sides of the separation membrane modules disposed in the same stage are connected in parallel. In other words, the separation membrane modules A1, B1, C1, and D1 which are disposed in the first stage of each of the series units are mutually connected in parallel by a pipe 31 via the exits for the permeated liquid of the modules, thereby forming a first parallel unit PU1. Similarly, sets of four separation membrane modules respectively disposed in the second stage and the third stage are connected to one another by pipes 32 and 33, thereby forming a second parallel unit PU2 and a third parallel unit PU3. A flow channel, for example, the pipe 31 by which the permeation sides of the separation membrane modules are connected in parallel is referred to as a parallel permeated liquid flow channel, and particularly, a flow channel by which the permeation sides of the separation membrane modules included in different series units are connected in parallel can be referred to as a unit-crossing parallel flow channel.

The filtration device of the present embodiment includes only the unit-crossing parallel flow channel as the parallel flow channel. However, the present invention is not limited thereto, and the filtration device may include the parallel permeated liquid flow channel which connects the modules in the same series unit.

In this manner, the plurality of separation membrane modules form a matrix of three rows by four columns.

The circulation pump 11 is disposed on an upstream side of the separation membrane modules which are disposed in a matrix state. In other words, the circulation pump 11 is disposed on the liquid supply line 20 which is connected to the fermentor 1. The circulation pump 11 supplies the fermentation liquid in the fermentor 1 to the separation membrane modules via the pipes. A portion of the fermentation liquid supplied to the separation membrane modules is filtrated by the separation membranes inside the modules, and the remaining portion thereof is supplied to the reflux line 60 through the pipes 61, 62, 63, and 64, as the circulation liquid, thereby returning to the fermentor. In this manner, as the fermentation liquid circulates between the fermentor and the filtration device, a stream of cross-flow can be generated on the separation membrane surface. The circulation pump 11 applies mechanical energy (that is, pressure) to the stream of cross-flow so that the stream from the fermentor can pass through the separation membrane modules and can return again to the fermentor. In this case, as a degree of the open state of the valve 141 on the reflux line 60 becomes smaller, liquid-passing resistance becomes larger. Therefore, the energy to be applied becomes greater. In other words, as the degree of the open state of the valve 141 becomes smaller, pressure of the stream of cross-flow in the valve 141 on the non-permeation side increases further.

The first to third filtrating operation control devices (51 to 53) are respectively provided in the stages of the matrix, that is, in the first to third parallel units (PU1 to PU3). The first filtrating operation control device 51 includes a permeated liquid flow rate sensor 41, a filtration pump 121, a valve 131, and a control unit 501. The filtrating operation control device 52 includes a permeated liquid flow rate sensor 42, a filtration pump 122, a valve 132, and a control unit 502. The filtrating operation control device 53 includes a permeated liquid flow rate sensor 43, a filtration pump 123, a valve 133, and a control unit 503.

Particularly in FIG. 1, the permeated liquid flow rate sensor 41 is disposed on the pipe 31 by which the permeated liquids of the separation membrane modules A1, B1, C1, and D1 included in the first parallel unit PU1 are connected in parallel. Similarly, the remaining permeated liquid flow rate sensors 42 and 43 are respectively disposed on the pipes 32 and 33 by which the permeated liquids of the separation membrane modules respectively included in the second parallel unit PU2 and the third parallel unit PU3 are connected in parallel. In this manner, the permeated liquid flow rate sensor is acceptable as long as the sensor can detect a flow rate of a liquid in the pipe which is connected to the permeation sides of the separation membrane modules included in each of the parallel units. As the permeated liquid flow rate sensor, for example, a mass flowmeter, an area flowmeter, an ultrasonic flowmeter, a differential pressure flowmeter, an electromagnetic flowmeter or the like can be used. The permeated liquid may be collected in a beaker or the like from the permeated liquid pipe for a predetermined time and a quantity per unit time may be calculated by measuring the weight or the volume so as to substitute the flow rate measurement. However, when being used in the continuous-fermentation apparatus, since steam sterilization is performed by heating the inside of the pipes in order to prevent contamination caused by contaminants, the flowmeter needs to be durable with respect to the steam sterilization.

Each of the permeated liquid flow rate sensors 41 to 43 is merely a type of a detection unit which detects operation states of the separation membrane modules in the parallel unit. Therefore, the permeated liquid flow rate sensors can be replaced by other configurations as described below.

The filtration pump 121 is disposed on the pipe 31 by which the permeated liquids of the separation membrane modules A1, B1, C1, and D1 included in the first parallel unit PU1 are connected in parallel. The filtration pump 122 of the second filtrating operation control device 52 and the filtration pump 123 of the third filtrating operation control device 53 are respectively disposed on the pipes 32 and 33 by which the permeated liquids of the separation membrane modules respectively included in the second parallel unit PU2 and the third parallel unit PU3 are connected in parallel.

The filtration control valve 131 is disposed on the pipe 31 between the first parallel unit PU1 and the filtration pump 121. Similarly, with regard to other filtration control valves, the filtration control valve 132 is disposed on the line 32 between the second parallel unit PU2 and the filtration pump 122, and the filtration control valve 133 is disposed on the line 33 between the third parallel unit PU3 and the filtration pump 123.

The filtrating operation control devices 51 to 53 control pressure of the permeated liquid so as to reduce the difference in the filtration flow rate or the transmembrane pressure difference among the parallel units. The controlling thereof can be outlined as follows. Detailed descriptions of the controlling will be given later. The transmembrane pressure difference indicates the difference between the pressure on the non-permeation side and the pressure of the permeated liquid in the separation membrane module.

The control unit 501 can control at least one of driving power of the filtration pump 121 and the degree of the open state of the valve 131 based on an output result of the permeated liquid flow rate sensor 41 which is provided on the pipe 31 of the first parallel unit. In this manner, the control unit 501 can collectively control the pressures of the permeated liquids in the separation membrane modules A1, B1, C1, and D1 included in the first parallel unit PU1.

The filtrating operation control devices 52 and 53 are disposed so as to respectively correspond to the second parallel unit PU2 and the third parallel unit PU3. Then, similar to the filtrating operation control device 51, each of the filtrating operation control devices 52 and 53 collectively controls the pressures of the permeated liquids in the separation membrane modules included in the second parallel unit PU2 and the third parallel unit PU3 based on the output results of the permeated liquid flow rate sensors 42 and 43.

The filtrating operation control devices 51 to 53 perform controlling for each of the parallel units in accordance with the degrees of the open states of the valves 131, 132, and 133, and the three filtration pumps 121 to 123 can be substituted with one pump. In such a case, the filtration pump is disposed on a pipe that connects the three pipes 31 to 33 in parallel on the downstream side of the valves 131 to 133.

As the non-permeation sides of the plurality of separation membrane modules are connected in series, a flow rate (a flow rate of cross-flow) of circulation in the entire filtration device is reduced. In addition, since the liquid supply lines, measuring gauges and the like can be shared among the separation membrane modules disposed in series, equipment can be simplified.

In the filtration device of the present embodiment, as the separation membrane modules are connected in parallel via the exits for the permeated liquid, the measuring gauges and the like for monitoring the pipe through which the permeated liquid flows and for monitoring the flow of the permeated liquid can be shared, and the equipment can be simplified further.

Moreover, in the present embodiment, the separation membrane modules respectively included in the series units different from one another and disposed in the same stage are connected together. Since a difference of the pressure of the liquid to be filtrated is small among the separation membrane modules disposed in the same stage, as the exits for the permeated liquid of the separation membrane modules are connected in parallel, even though the plurality of separation membrane modules share the permeated liquid pipe, the difference in the transmembrane pressure difference among the separation membrane modules is small. Therefore, inequality of the filtration amounts caused by the difference in the transmembrane pressure difference is unlikely to occur among the separation membrane modules. In this manner, when a member such as a pipe on the permeation sides is shared among the plurality of separation membrane modules, it is preferable to connect the permeation sides of the separation membrane modules indicating equivalent pressure on the non-permeation sides. Hereinafter, descriptions will be given in detail.

If the non-permeation sides of the separation membrane modules are disposed in series, due to pressure loss caused by the separation membrane modules and the pipes, a difference occurs in pressure on the non-permeation sides between a separation membrane module in a fore stage (the upstream side in the stream of cross-flow) and a separation membrane module in a later stage (the downstream side in the stream of cross-flow), thereby leading to an occurrence of a difference in the transmembrane pressure differences. As a result thereof, a difference occurs among the filtration amounts. For example, compared to the module in the fore stage, pressure on the non-permeation side becomes smaller in the module in the later stage. In other words, as the stage of the module becomes later, transmembrane pressure difference thereof becomes smaller, and thus, the filtration amount thereof become smaller.

Among the separation membrane modules which can obtain the filtration amounts similar to one another under the same pressure condition such as a case where all the separation membrane modules are brand-new products, as the transmembrane pressure difference of the separation membrane module becomes smaller, the filtration amount thereof becomes smaller.

When similar filtration amounts cannot be obtained under the same pressure condition, for example, in a case where a portion of the separation membrane modules has been used for a long period and clogging is in progress in the membrane, if the module is disposed in a later stage, the filtration amount becomes much smaller.

Particularly, when the flow rate of cross-flow increases, pressure loss caused by the pipes increases. Moreover, in a case where the flow rate of cross-flow is significant, a rectification member may be disposed inside the module so as to cause the stream of cross-flow inside the module to be equal. If the rectification member is provided, pressure loss increases further.

In the separation membrane modules exhibiting significant filtration amounts, clogging is more likely to occur in the membranes as compared to the separation membrane modules exhibiting smaller filtration amounts. In other words, when there is a difference among the filtration amounts, a burden of maintenance increases.

Therefore, in order to reduce the difference between the filtration amounts of the separation membrane module in a fore stage and the separation membrane module in a later stage which are disposed in series, and to stably continue the operation, it is preferable to adjust the transmembrane pressure difference of the separation membrane module in a fore stage and that of the separation membrane module in a later stage to be approximately the same. In the case where the flow rate of cross-flow is stationary, a chronological change in pressure on the non-permeation side is small, and a chronological change in pressure on the permeation side is large, and therefore, it is desirable to adjust the pressure on the permeation side.

Here, as the exits for the permeated liquid of the plurality of separation membrane modules are connected in parallel, the pressures of the permeated liquids in the plurality of separation membrane modules can be collectively controlled. The pressure of the permeated liquid can be chronologically adjusted by changing the degree of the open state of the valve on the pipe through which the permeated liquid passes.

Since the pressures of the permeated liquids can be individually controlled for each of the stages disposed in series, the filtration amounts thereof can also be set for each of the stages. In other words, even though there is a difference in pressure on the non-permeation side between the separation membrane modules in a fore stage and a later stage, the difference between the filtration amounts thereof can be reduced by boosting/reducing pressure on the permeation side. Moreover, it is possible to perform an operation so as to decrease the difference in the transmembrane pressure difference.

Particularly, as described above, when the transmembrane pressure difference of the parallel unit in the fore stage becomes large due to pressure loss as compared to the transmembrane pressure difference of the parallel unit in the later stage, it is possible to reduce the difference between the filtration amounts of the stages by controlling the pressure of the permeated liquid of the parallel unit in the later stage to be lower than the pressure of the permeated liquid in the parallel unit in the fore stage. Specifically, as the driving power of the filtration pump which is connected to the modules in the later stage is increased, the difference in the transmembrane pressure difference is reduced. In other words, the filtration flow rates thereof in the fore stage and the later stage are averaged. Moreover, the degree of the open state of the filtration control valve which is connected to the modules in the later stage may be increased, or the degree of the open state of the filtration control valve which is connected to the modules in the fore stage may be decreased.

When the configuration is changed, for example, when a boosting pump is disposed on the flow channel for the liquid to be filtrated connecting the separation membrane modules in series, the magnitude relationship between the transmembrane pressure difference of the parallel unit in the fore stage and the transmembrane pressure difference of the parallel unit in the later stage can be reversed. In other words, for example, when the boosting pump is provided on each of the flow channels for the non-permeated liquid between the separation membrane module A2 and the separation membrane module A3, between the separation membrane module B2 and the separation membrane module B3, between the separation membrane module C2 and the separation membrane module C3, and between the separation membrane module D2 and the separation membrane module D3, as the boosting pumps are in operation, the transmembrane pressure difference generated in the modules in the later stage may become larger than the transmembrane pressure difference generated in the modules in the fore stage. In such a case as well, for example, the parallel unit in the fore stage may be provided with one filtrating operation control device. The filtrating operation control device can collectively control the filtration amounts of the modules included in one parallel unit separately from the modules in the later stage. In this manner, the difference between the filtration amounts thereof in the fore stage and the later stage can be averaged.

The transmembrane pressure difference can be controlled by applying different means. For example, a liquid-passing resistor such as a valve (the valve 141) and an orifice is installed on the liquid supply line on the liquid to be filtrated side and the pressure of the liquid to be filtrated is increased so that the transmembrane pressure difference of all the modules can be increased. In addition, the liquid-passing resistors such as the orifices different from one another in size are installed in the pipe on the permeation side for each of the stages and pressure on the permeation side is reduced so that the transmembrane pressure differences and the filtration amounts of each of the stages can be averaged.

For example, in the apparatus of FIG. 1, equipment such as the orifice causing a pressure loss is provided in each of the lines on the permeation sides of the separation membrane modules in the separation membrane module parallel unit PU1 or is provided at a portion where each of the lines on the permeation sides of the separation membrane modules is merged, and then, when the pressure loss of the orifice and the like is similar to the pressure loss caused by the separation membrane module A1 and the pipes, even though a filtrating operation is performed for the separation membrane module parallel units PU1 and PU2 by using the same filtration control device, it is possible to perform the filtrating operation under the same level of the transmembrane pressure difference of each separation membrane module in the separation membrane module parallel units PU1 and PU2.

When it is difficult to adjust the pressure on the permeation side, for example, in a case where the valve on the permeation side is fully opened, the pressure of the liquid to be filtrated can be adjusted by manipulating the valve 141 and the like on the reflux line as described above.

A pipe 20 which is a line for supplying the fermentation liquid from the fermentor 1 to the separation membrane modules may be connected with a bypass which allows the fermentation liquid to return to the fermentor 1 without passing through the separation membrane modules. By providing such a bypass line, when a portion of the separation membrane modules is suspended, for example, in a case where filtration properties thereof are deteriorated, cross-flow as much as that of the suspended separation membrane modules can flow through the bypass. Therefore, it is possible to prevent pressure of the entire apparatus from varying.

(1-3) Filtrating Operation Control Device

Figure 7:
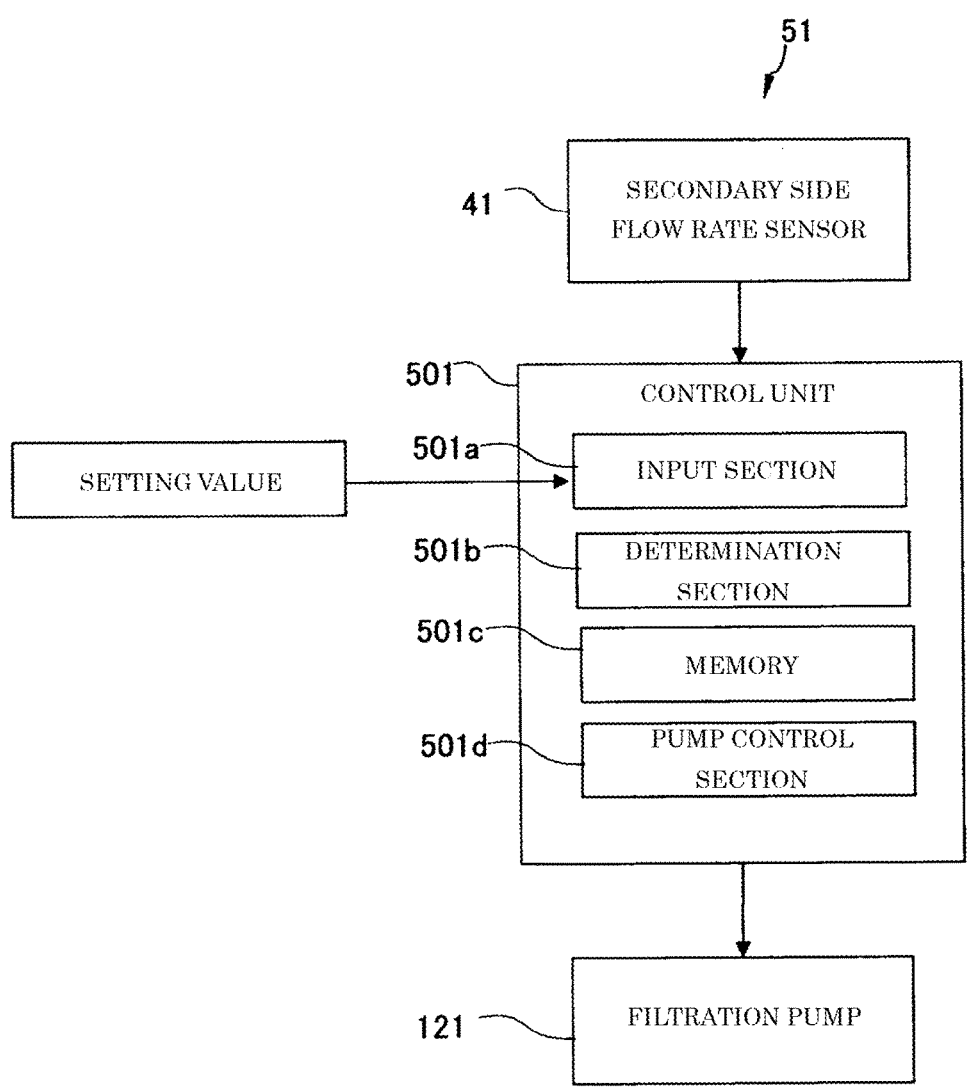
FIG. 7 is a functional block diagram illustrating an example of a filtrating operation control device.

FIG. 7 illustrates an example of a functional block diagram of the filtrating operation control device. The filtrating operation control device 51 illustrated in FIG. 7 is an example of a control device which is connected to the parallel unit PU1 in the first stage. The filtrating operation control device 51 includes the permeated liquid flow rate sensor 41, the control unit 501, and the filtration pump 121.

The control unit 501 includes an input section 501a, a determination section 501b, a memory 501c, and a pump control section 501d.

Figure 8:
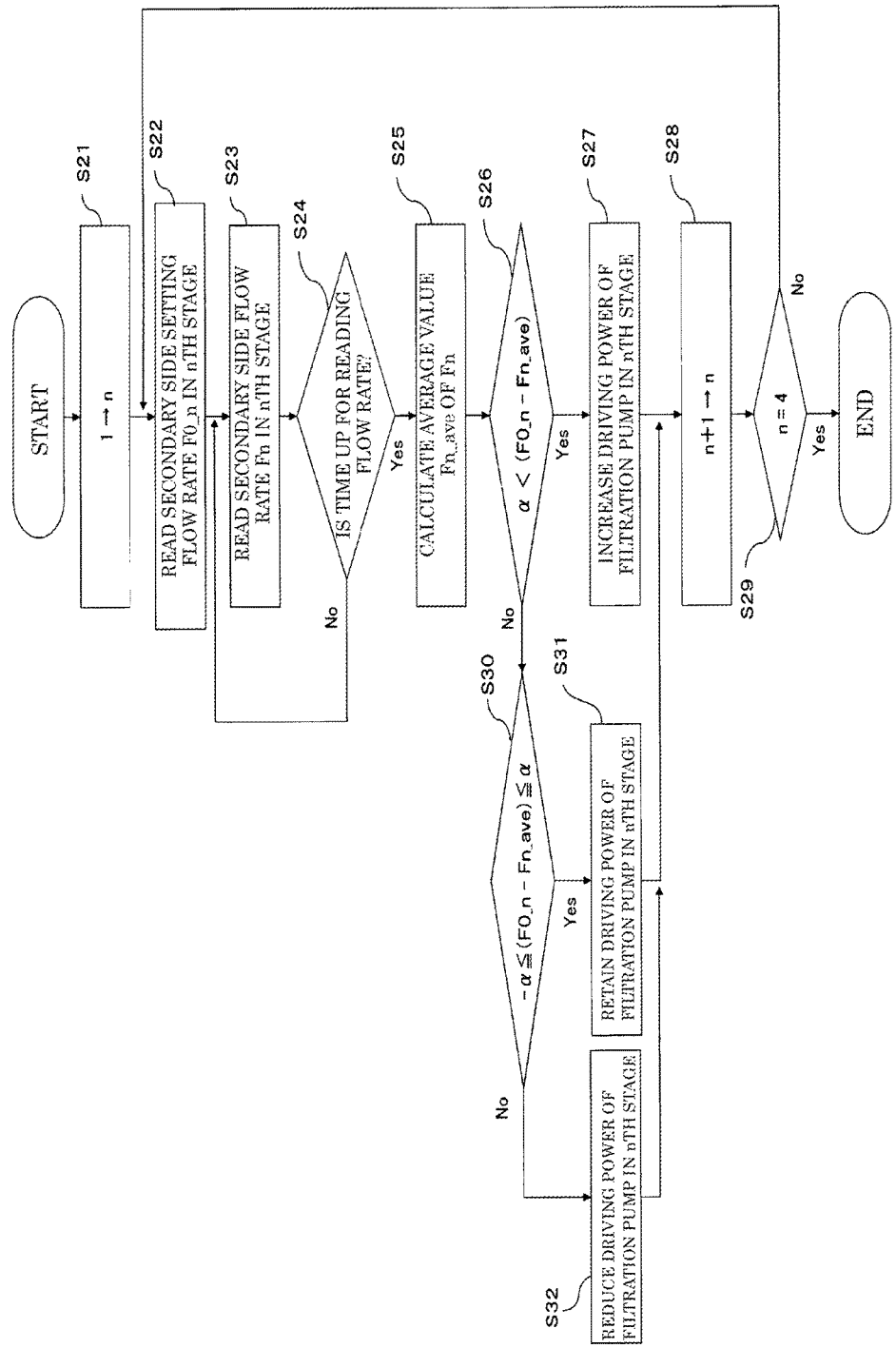
FIG. 8 is a flow chart illustrating an example of an operation of controlling a filtrating operation.

FIG. 8 illustrates a flow chart showing an example of an operation of controlling a filtrating operation. The determination section 501b determines necessity of driving and the driving power of the filtration pump 121 based on an output result of the permeated liquid flow rate sensor 41. When approximating the flow rate of the permeated liquid in the first stage to a criterial set flow rate, the determination section 501b calculates a difference between a detection result of the permeated liquid flow rate sensor 41 in the first stage and the criterial set flow rate, thereby determining the magnitude relationship between the obtained difference and a predetermined value (a threshold value). The memory 501c stores a value of the driving power of the filtration pump corresponding to the difference between the criterial set flow rate and the flow rate of the permeated liquid in the first stage.

The pump control section 501d controls the filtration pump 121 based on a comparison result of the determination section 501b and information stored in the memory 501c. For example, with regard to the pump control section 501d, when the flow rate of the permeated liquid in the first stage is smaller than the criterial set flow rate and a difference therebetween is greater than a predetermined amount, the pump control section 501d raises the driving power of the filtration pump. When the flow rate of the permeated liquid in the first stage is greater than the criterial set flow rate and the difference therebetween is greater than a predetermined amount, the pump control section 501d reduces the driving power of the filtration pump. Even though the flow rate of the permeated liquid in the first stage is the same as or different from the criterial set flow rate, as long as the flow rate is within a permissible range, the pump control section 501d maintains the driving power of the filtration pump 121. In this manner, the filtrating operation is controlled.

As a criterial value for determination, an upper limit value and a lower limit value of pressure may be stored in the memory 501c in advance. In this case, when pressure exceeds the upper limit value, the determination section 501b determines that the driving power of the filtration pump 121 needs to be decreased, and when pressure falls below the lower limit value, the determination section 501b determines that the driving power of the filtration pump 121 needs to be increased.

With regard to inputting of a setting flow rate to the input section 501a, a worker may judge and perform the inputting, or a setting value may be output to the input section 501a by providing an input device in which a different detection sensor is applied.

It is preferable that the flow rate to be individually set to each of the stages is set so as to cause the ratio of a maximum setting value to a minimum setting value to be equal to or less than three times, to be preferably equal to or less than twice, and to be further preferably equal to or less than 1.5 times, thereby preventing the separation membrane modules from being locally applied with an overload.

When collectively controlling each of the stages, the separation membrane modules applied with large transmembrane pressure difference tend to have the filtration amounts larger than those of other separation membrane modules, thereby obtaining relatively more filtration amounts. When the number of the stages in series for the separation membrane modules becomes greater, the filtration amount of the entire apparatus becomes greater. Therefore, larger filtration amounts are concentrated on a local portion of the modules, and it is assumed that the modules differ from one another in the filtration amount up to five times or more depending on the number of the stages of the modules.

In contrast, in the present embodiment, since each of the stages is individually controlled, it is possible to suppress such tendency and to stably perform the operation.

The filtrating operation control device for driving the filtration pump may be used while using a permeated liquid pressure sensor as the detection sensor in place of the permeated liquid flow rate sensor.

(2) Second Embodiment

Figure 3:
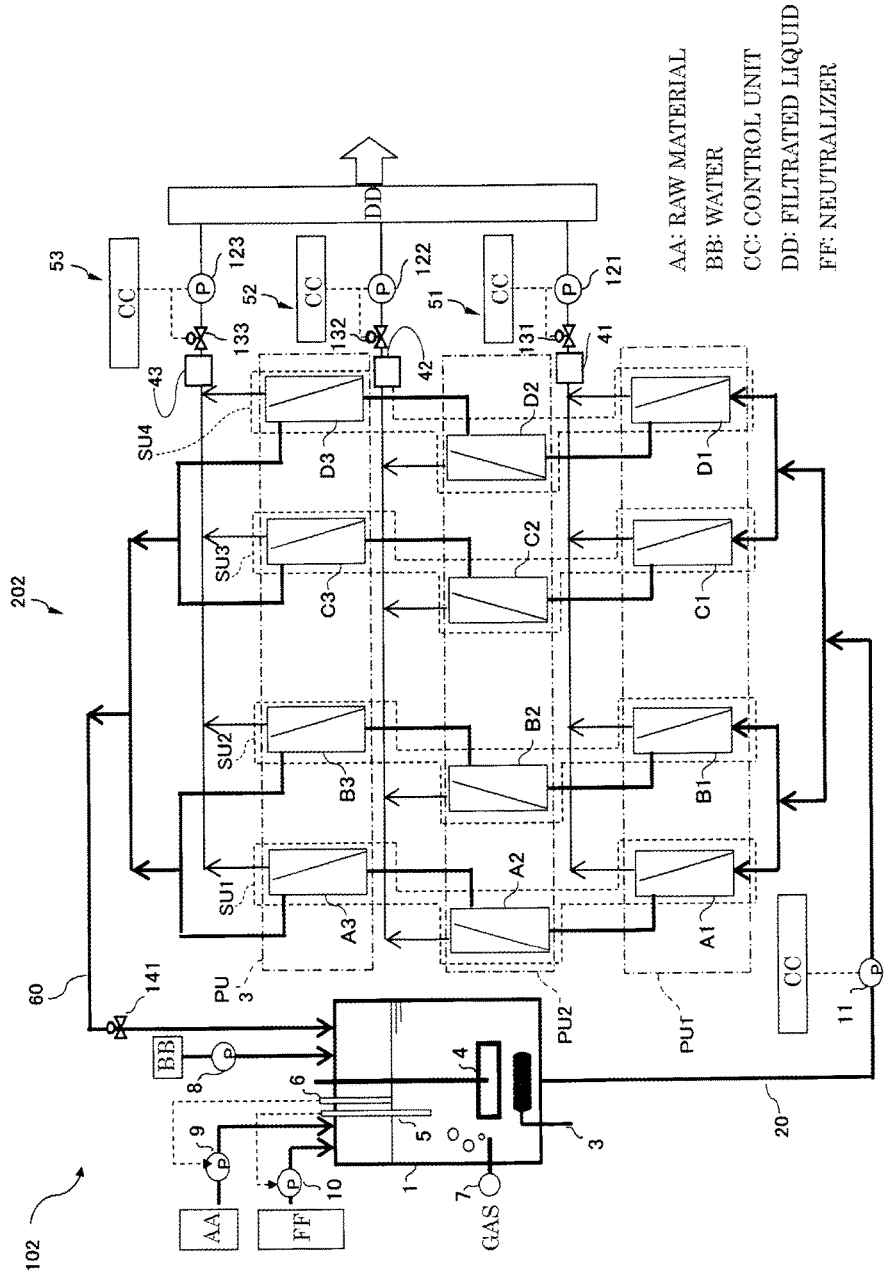
FIG. 3 is a schematic diagram of the continuous-fermentation apparatus according to a second embodiment of the present invention.

FIG. 3 is a schematic diagram of the continuous-fermentation apparatus used in a second embodiment of the present invention. In a continuous-fermentation apparatus 102 according to the second embodiment of the present invention, the lengths of the pipes for supplying the fermentation liquid from the circulation pump 11 to each of the separation membrane modules A1, B1, C1, and D1 in the first stage are set to be substantially equal to one another. The lengths of the pipes provided from the separation membrane modules A3, B3, C3 and D3 in the lattermost stage to the fermentor 1 are also set to be substantially equal to one another. The continuous-fermentation apparatus 102 includes a filtration device 202.

Specifically, the series units SU1 and SU2 are connected in parallel through the flow channel for the non-permeated liquid, and the series units SU3 and SU4 are connected in parallel through the flow channel for the non-permeated liquid. In other words, the liquid supply line 20 through which the fermentation liquid is supplied from the fermentor 1 to the separation membrane module group branches off into two lines, and then, one line therebetween branches off into two lines further, thereby being connected to the separation membrane modules A1 and B1 of the series units SU1 and SU2 in the foremost stage. The other pipe which has branched off also branches off into two lines furthermore, thereby being connected to the separation membrane modules C1 and D1 of the series units SU3 and SU4 in the foremost stage. The separation membrane modules A3 and B3 of the series units SU1 and SU2 in the lattermost stage are connected in parallel via each of the exits for the non-permeated liquid so as to cause the non-permeated liquid flowing out from the two separation membrane modules to merge together. With regard to the remaining two series units SU3 and SU4 as well, the modules in the lattermost stage respectively belonging thereto are connected in parallel via the exits for the non-permeated liquid.

In the first embodiment, the non-permeation sides of all the series units SU1 to SU4 in the foremost stage and the lattermost stage are connected in parallel, whereas in the second embodiment, the series units SU1 and SU2 are disposed as a set and the series units SU3 and SU4 are disposed as a set so as to cause the disposition of the modules and the pipes to be bilaterally symmetrical in the entire module group.

(3) Third Embodiment

Figure 4:
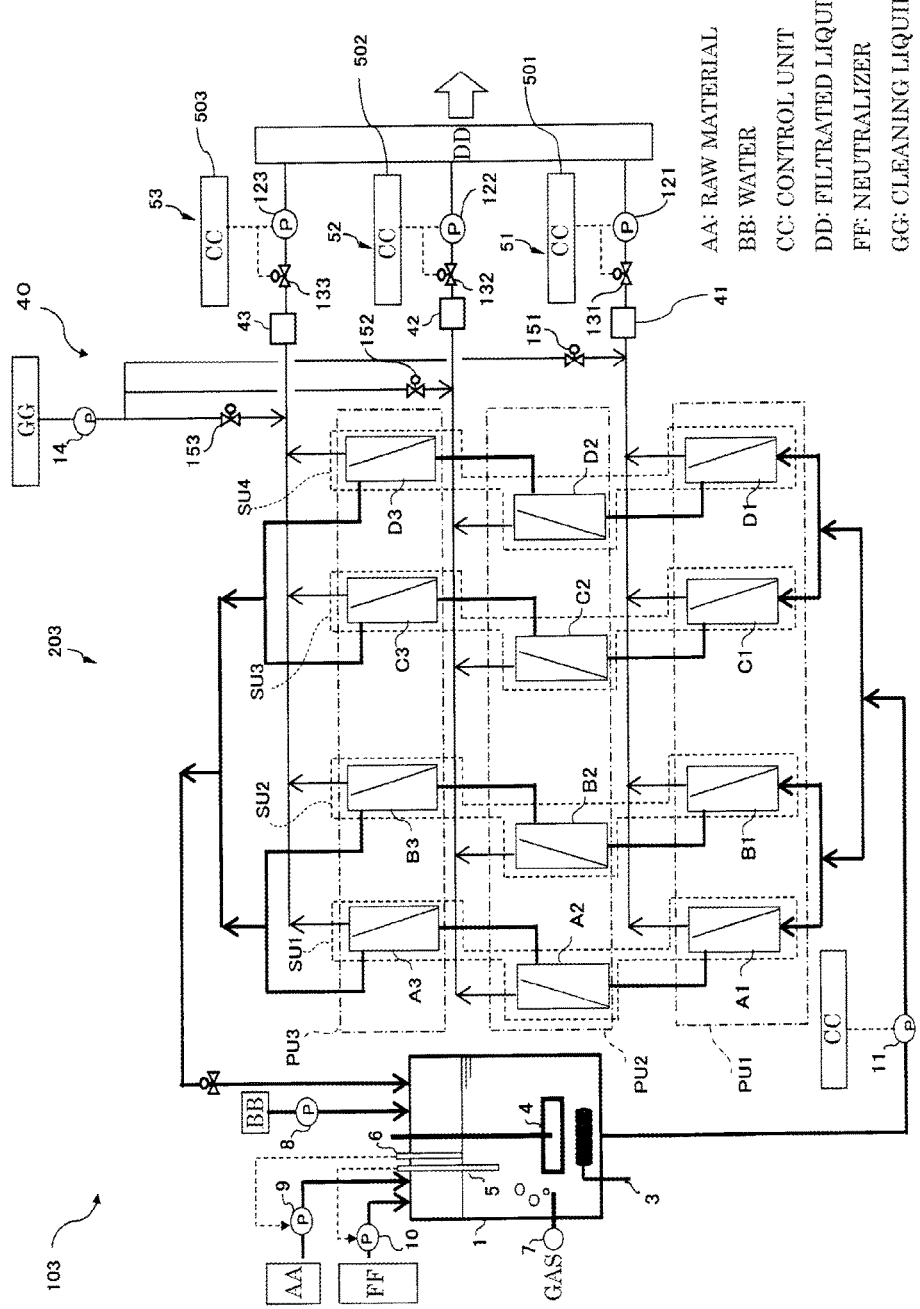
FIG. 4 is a schematic diagram of the continuous-fermentation apparatus which includes a mechanism for performing backwashing.

A fermentation apparatus 103 illustrated in FIG. 4 has a configuration similar to that of the continuous-fermentation apparatus 102 in the second embodiment except that a membrane cleaning device 40 is included to perform backwashing for the separation membrane modules. The fermentation apparatus 103 includes a filtration device 203.

As illustrated in FIG. 4, the membrane cleaning device 40 includes a cleaning liquid tank which stores a cleaning liquid, pipes through which the cleaning liquid is supplied to each of the parallel units, and a cleaning liquid pump 14. Moreover, a cleaning liquid valve 151, a cleaning liquid valve 152, and a cleaning liquid valve 153 are respectively disposed on the pipes through which the cleaning liquid is supplied to the parallel units.

It is preferable that the cleaning liquid tank, the cleaning liquid pump 14, the pipes provided from the cleaning liquid tank to the separation membrane modules, and a cleaning liquid valve 15 have excellent chemical resistance. A backwashing liquid can be manually injected. However, it is preferable that the control unit automatically controls the filtration pumps 121 to 123, the filtration control valves 131 to 133, the cleaning liquid pump 14, and the cleaning liquid valves 151 to 153 by utilizing a timer and the like.

As the non-permeation sides of the separation membrane modules are connected in series, the flow rate (the flow rate of cross-flow) of circulation in the filtration device in its entirety is reduced. In addition, since the liquid supply lines, the measuring gauges, and the like can be shared among the separation membrane modules disposed in series, the equipment can be simplified.

However, as described in the first embodiment, when the separation membrane modules are disposed in series, a difference occurs among the filtration amounts or the transmembrane pressure differences among the stages.

The transmembrane pressure difference applies resistance to a stream of the cleaning liquid when supplying the cleaning liquid from the permeation sides of the separation membranes to the non-permeation sides thereof. The resistance becomes larger as a value of the transmembrane pressure difference becomes larger. Therefore, when a difference occurs in the transmembrane pressure difference among the separation membrane modules, a difference occurs in flowability of the cleaning liquid among the modules. For example, when the transmembrane pressure difference of the modules in a later stage (the downstream side in the stream of an original fluid) is smaller as compared to that of the modules in a fore stage (the upstream side in the stream of the original fluid), the cleaning liquid is likely to flow toward the modules in the later stage, and an error may occur in supplying of the cleaning liquid to the modules in the fore stage, thereby resulting in insufficiently cleaned fore stage modules. Moreover, the flow rate of supplying the cleaning liquid may be greater than the filtration flow rate. In such a case, resistance further becomes larger, and the bias in the supply amount of the cleaning liquid becomes notable depending on the module.

Therefore, in order to equally supply the cleaning liquid among the separation membrane modules disposed in series, it is preferably considered to be controlled individually. However, in order to perform such individual controlling, there is a need to provide the control device for each of the separation membrane modules so that the equipment increases in size and the equipment increases in cost as well.

In contrast, in the filtration device of the present embodiment, the pipes for the permeated liquid, the measuring gauges, and the like can be shared as the permeation sides of the separation membrane modules included in the series units different from one another are connected in parallel, and therefore, the equipment can be simplified further. As described above, since a difference in the transmembrane pressure difference is small among the separation membrane modules which are disposed in the same stage, even though the separation membrane modules share the permeated liquid pipes, it is possible to reduce the difference in the supply amount of the cleaning liquid among the separation membrane modules. Furthermore, the cleaning step for the plurality of separation membrane modules connected in parallel can be collectively controlled.

The membrane cleaning device can also be applied to the filtration device of the first embodiment.

(4) Fourth Embodiment

Figure 6:
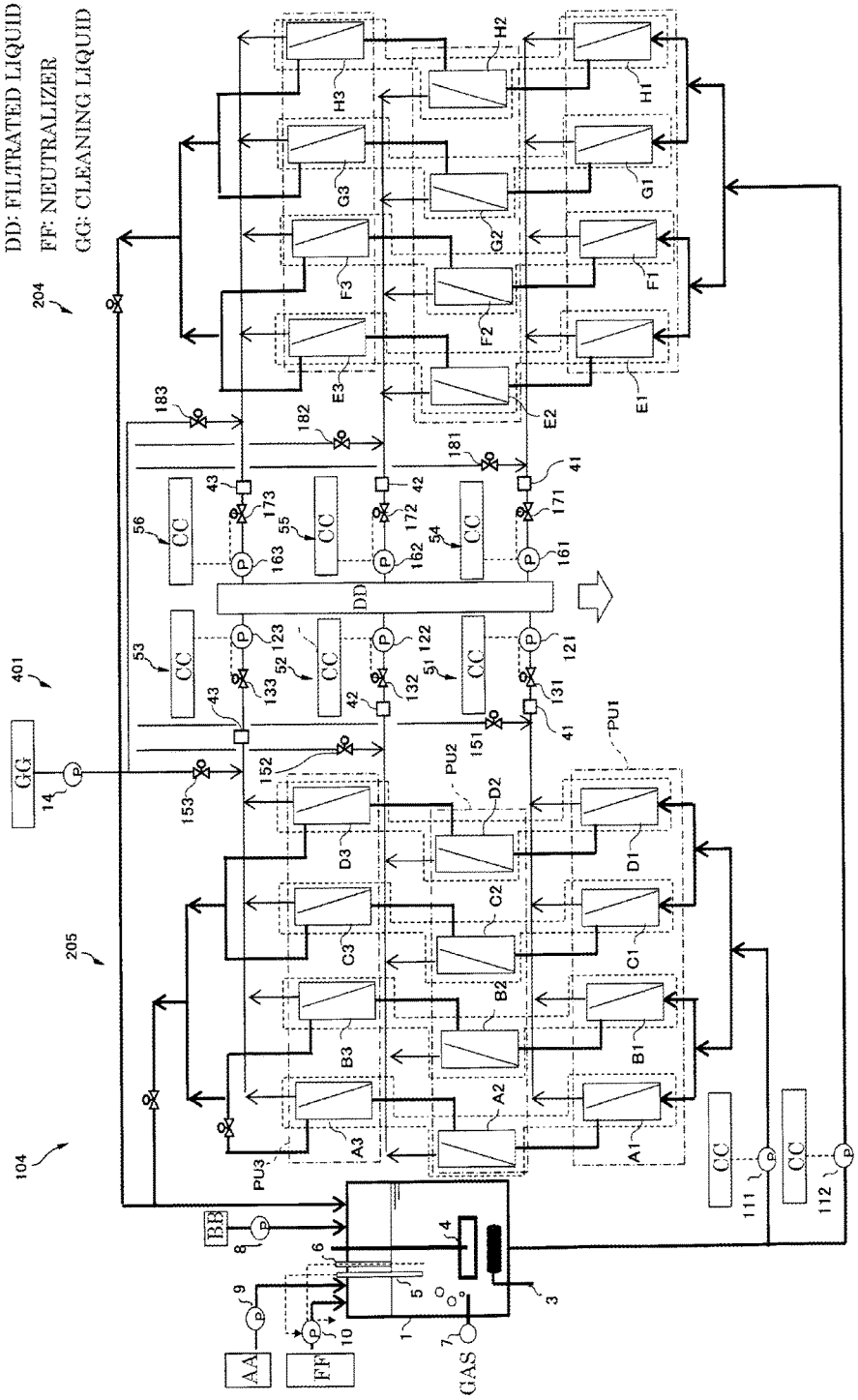
FIG. 6 is a schematic diagram of the continuous-fermentation apparatus according to another embodiment.

As illustrated in FIG. 6, a fermentation apparatus 104 of the present embodiment has a filtration device 204 and a filtration device 205 each of which has twelve separation membrane modules. The filtration device 204 and the filtration device 205 respectively includes two module groups each of which includes the twelve separation membrane modules disposed so as to form a bilaterally symmetrical matrix similar to that of the third embodiment. The foremost stage and the lattermost stage of each of the two module groups are also connected in parallel. In other words, the fermentation apparatus 104 includes two filtration devices which are substantially similar to that of the third embodiment.

The filtration device 204 includes filtrating operation control devices (control units) 54, 55, and 56, filtration pumps 161, 162, and 163, filtration control valves 171, 172, and 173, and cleaning liquid valves 181, 182, and 183. Moreover, the filtration device 204 includes separation membrane modules E1, F1, G1 and H1, separation membrane modules E2, F2, G2 and H2, and separation membrane modules E3, F3, G3 and H3.

The permeated liquids of the modules in the same stage within each of the matrix arrangement are connected in parallel, and the filtrating operation control device is provided for each stage in each matrix. In this manner, in the present embodiment, the modules are disposed so as to be bilaterally symmetrical in the entire filtration device.

II. Method for Manufacturing Chemical and Operations of Device and Apparatus

Hereinafter, descriptions will be given regarding the method for manufacturing a chemical performed by utilizing the filtration device and the fermentation apparatus of the present invention.

1. Fermentation Step

In the present embodiment, the method for manufacturing a chemical includes a fermentation step in which fermentation is performed by using cells so as to convert a raw material into a fermentation liquid containing a chemical.

(A) Cell

In the present embodiment, the term "cells" is referred to as a general term of microorganisms and cultured cells.

The microorganisms used for the manufacture of a chemical are not particularly limited. For example, yeast such as bakery yeast; eukaryotic cells such as filamentous bacteria; and prokaryotic cells such as colon bacteria, lactic acid bacteria, coryneform group of bacteria and actinomycetes, which are frequently used in the fermentation industry can be exemplified. Animal cells, insect cells, and the like can be exemplified as the cultured cells. The microorganisms and the cultured cells to be used may be a result of isolation obtained from a natural environment, or a result of which properties are partially modified through mutation or gene recombination.

When manufacturing a lactic acid, it is preferable to use yeast for eukaryotic cells and to use lactic acid bacteria for prokaryotic cells. With regard to the yeast, it is preferable to use yeast in which genes encoding lactic acid dehydrogenase is introduced into cells thereof. With regard to the lactic acid bacteria, it is preferable to use lactic acid bacteria which produce a lactic acid in a yield based on sugar with respect to consumed glucose equal to or more than 50%, and it is more preferable to use lactic acid bacteria with a yield based on sugar equal to or more than 80%.

(B) Raw Material

With regard to a raw material, it is acceptable as long as the raw material can promote growth of cells to be cultivated and can favorably produce a chemical which is a targeted fermentation product.

A liquid culture medium is used as a raw material. A substance (that is, a raw material in a narrow sense) which is a component in the culture medium and is converted into a targeted chemical may be referred to as a raw material. However, in this Description, unless particularly discriminated, the entire culture medium will be referred to as a raw material. A raw material in a narrow sense is sugar, for example, glucose, fructose, and sucrose which are fermentation substrates for obtaining alcohol as a chemical.

A raw material suitably contains a carbon source, a nitrogen source, an inorganic salt, and an organic micronutrient such as an amino acid and a vitamin, as necessary. As the carbon source, saccharides such as glucose, sucrose, fructose, galactose, and lactose; a starch saccharified solution, sweet potato molasses, sugar beet molasses, and hi-test molasses containing the aforementioned saccharides; an organic acid such as an acetic acid; alcohols such as ethanol; glycerin; and the like are used. As the nitrogen source, ammonia gas; aqueous ammonia; ammonia salts; urea; nitrates; an organic nitrogen source which is auxiliarily used, for example, oil cakes, soybean hydrolyzate, and casein hydrolyzate; other amino acids; vitamins; corn steep liquor; yeast or yeast extract; meat extract; peptides such as peptone; various fermentation bacterial cells and hydrolyzates thereof; and the like are used. As the inorganic salt, phosphate, magnesium salt, calcium salt, iron salt, manganese salt, and the like may be added.

When a particular nutrient is necessary for growth of cells, the nutrient is added to a raw material as a specimen or a natural product containing the nutrient.

A raw material may contain an antifoaming agent as necessary.

(C) Cultivation Liquid

A cultivation liquid is a liquid which can be obtained as a result when cells proliferate in a culture medium including a raw material.

With regard to continuous fermentation, a raw material can be additionally added to the cultivation liquid. In this case, the composition of a raw material to be additionally added may be suitably changed from the composition at the initial stage of cultivation so as to enhance the productivity of targeted chemicals. For example, the concentration of a raw material in a narrow sense, the concentration of other components in the culture medium, and the like are changeable.

(D) Fermentation Liquid

A fermentation liquid is a liquid containing a substance which is generated as a result of fermentation. The fermentation liquid may contain a raw material, cells, and a chemical. In other words, the terms "the cultivation liquid" and "the fermentation liquid" may be used as substantially synonymous terms.

(E) Chemical

By using the above-described cells, a chemical, that is, a substance which has been converted is produced in the fermentation liquid. As the chemical, substances which are mass-produced in the fermentation industry can be exemplified, for example, alcohol, an organic acid, an amino acid, a nucleic acid, and the like. For example, as the alcohol, ethanol, 1,3-butanediol, 1,4-butanediol, glycerol, and the like can be exemplified. As the organic acid, an acetic acid, a lactic acid, a pyruvic acid, a succinic acid, a malic acid, an itaconic acid, a citric acid, and the like can be exemplified. As the nucleic acid, inosine, guanosine, cytidine, and the like can be exemplified. Moreover, the method of the present invention can be applied to the production of substances such as enzymes, antibiotics, and recombinant proteins.

In addition, the manufacturing method of the present invention can be applied to the manufacture of chemical products, dairy products, pharmaceuticals, food, and brewing products. Here, as the chemical product, for example, an organic acid, an amino acid, and a nucleic acid can be exemplified. As the dairy product, for example, low-fat milk and the like can be exemplified. As the food, for example, lactic acid drink and the like can be exemplified. As the brewing product, for example, beer and clear liquor distilled from sweet potatoes or the like can be exemplified. Enzymes, antibiotics, recombinant proteins, and the like manufactured by the manufacturing method of the present invention can be applied to medical and pharmaceutical products.

(F) Cultivation

In the manufacture of a chemical performed through continuous fermentation, the continuous fermentation (that is, removal of the cultivation liquid) may start after Batch cultivation or Fed-Batch cultivation is performed at the initial stage of cultivation and cell concentration is raised. Otherwise, after cell concentration is raised, the highly concentrated bacterial cells may become seeded. Then, cultivation may start and at the same time, the continuous fermentation may be performed. In the manufacture of a chemical performed through continuous fermentation, the supply of a raw material cultivation liquid and removal of cultures can be performed starting at a suitable time. The starting times of the supply of a raw material cultivation liquid and the removal of the cultivation liquid are not necessarily the same. Moreover, the supply of a raw material cultivation liquid and the removal of the cultivation liquid may be continuously performed or may be intermittently performed.

A nutrient which is necessary for causing bacterial cells to proliferate may be added to the cultivation liquid so that the bacterial cells continuously proliferate. As an aspect for achieving favorably efficient productivity, it is preferable that the cell concentration of the cultivation liquid is maintained to be high to the extent that a range in which the ratio of extinction caused by an environment of the cultivation liquid that is inappropriate for proliferation of cells, does not increase. With regard to the cell concentration of the cultivation liquid, as an example, favorable production efficiency can be obtained in D-lactic acid fermentation using lactic acid bacteria by maintaining cell concentration to be equal to or greater than 5 g/L, as a dry weight.

In the manufacture of a chemical performed through continuous fermentation, when saccharides are used as a raw material, it is preferable that the concentration of saccharides in the cultivation liquid is retained to be equal to or less than 5 g/L. The reason that retaining the concentration of the saccharides in the cultivation liquid to be equal or less than 5 g/L is preferable, is that it minimizes the occurrence of saccharides being swept away due to removal of the cultivation liquid.

Cultivation of cells is generally performed within a range from pH 3 to pH 8 and a temperature range from 20° C. to 60° C. The pH value of the cultivation liquid is generally adjusted to a predetermined value ranging from pH 3 to pH 8 in advance by using an inorganic acid, an organic acid, an alkaline substance, and furthermore, urea, calcium carbonate, ammonia gas, and the like. When the supply rate of oxygen needs to be raised, it is possible to adopt means such as adding oxygen to air for maintaining oxygen concentration to be equal to or greater than 21%, pressurizing the cultivation liquid, raising an agitating rate, increasing a quantity of airflow, and the like.

With regard to an operation of continuous fermentation, it is desirable to monitor cell concentration in the fermentor. The cell concentration can be measured by collecting and measuring a sample. However, it is desirable to install a cell concentration sensor such as an MLSS measuring instrument in the fermentor for cells, thereby continuously monitoring the changing state of the cell concentration.

In the manufacture of a chemical performed through continuous fermentation, as necessary, the cultivation liquid and cells can be removed from the inside of the fermentor. For example, when cell concentration inside the fermentor becomes too high, a blockage of a separation membrane is likely to occur. Therefore, it is possible to prevent the separation membrane from being blocked by performing the removal. Productive performance of a chemical may vary due to cell concentration inside the fermentor. However, it is possible to retain the productive performance by removing cells while taking the productive performance as an index.

In the manufacture of a chemical performed through continuous fermentation, the number of the fermentors does not matter. In the manufacture of a chemical performed through continuous fermentation, it is preferable that operations of continuous cultivation are generally performed in a simplex fermentor in view of cultivation management. Due to small capacity of the fermentor, it is also possible to use a plurality of the fermentors. In this case, continuous cultivation may be performed by using the plurality of fermenters which are connected in parallel or in series through pipes.

2. Filtration Step (A) Overall Filtration Step

Hereinafter, descriptions will be given regarding a filtration step performed in the continuous-fermentation apparatus 101 of the present embodiment illustrated in FIG. 1. The fermentation liquid including fermentation products is filtrated through the separation membrane module, thereby being separated into cells and the fermentation products. The permeated liquid including the fermentation products (that is, the targeted chemicals) is collected so as to be removed outside the fermentation apparatus 101. Since the separated cells return to the fermentor 1, cell concentration inside the fermentor is retained in a high state. As a result thereof, it is possible to perform fermentation production with high productivity.

When executing filtration, the fermentation liquid is supplied to all the series units SU1 to SU4 by the circulation pump 11 while the filtration control valves 131 to 133 are opened. The fermentation liquid supplied to the non-permeation side of the separation membrane module is separated into the permeated liquid and the non-permeated liquid. The permeated liquid is collected through the exit for the permeated liquid of the separation membrane module. In this manner, a chemical which is a fermentation product is collected by the filtration.

Pressure of the fermentation liquid which is to be supplied to the separation membrane module may be varied. A turbulent region can be locally formed by varying discharge pressure of the circulation pump 11 so that the shearing force of cross-flow can increase with respect to the fermentation liquid and sediments such as cells which are sedimented on the separation membrane surface can be eliminated.

With regard to variation in discharge pressure of the circulation pump 11, the discharge pressure may be continuously varied. Generally, discharge pressure of the circulation pump 11 is operated in a substantially uniform state. However, the control valve may be operated for the set time only so that the discharge pressure can intermittently vary during the set time only.

As the variation in the discharge pressure of the circulation pump 11 is large, the effect of removing sediments becomes large, and as the pressure variation thereof is small, the liquid supply pipe is prevented from leaking from a connection portion caused by hunting of the liquid supply pipe. Therefore, it is desirable that the magnitude of the pressure variation of the circulation pump 11 ranges from 3% to 20% with respect to the discharge pressure.

Gas can be mixed into the fermentation liquid to be supplied by supplying gas to the liquid supply line for circulation of cross-flow, for example, by supplying gas to the liquid supply pipes and the separation membrane modules at the same time gas so that the shearing force can be enhanced by the gas which has been mixed into the fermentation liquid. Accordingly, it is possible to further increase the effect of removing sediments such as cells from the separation membrane surface.

Solutions collected from each of the separation membrane modules are supplied to a permeated liquid collection section (not illustrated) via the pipe in each of the stages in the separation membrane modules which are disposed in parallel. Meanwhile, the fermentation liquid (the non-permeated liquid) which has not been filtrated through the separation membrane modules returns to the fermentor 1 via the pipes.

It is preferable that the transmembrane pressure difference (that is, driving power for filtration) at the time of performing filtration treatment of the fermentation liquid through the separation membrane in the separation membrane module is adjusted within a range in which the cultured cells and culture medium components are not easily clogged. As a specific example, the transmembrane pressure difference ranges from 0.1 kPa to 200 kPa, preferably ranges from 0.1 kPa to 10 kPa, and more preferably ranges from 0.1 kPa to 5 kPa. When the transmembrane pressure difference is within the aforementioned range, clogging of cells (particularly, prokaryotic cells) and the culture medium components, and deterioration in the filtration amount are prevented. As a result thereof, disadvantages in the continuous fermentation operation are effectively prevented from occurring.

Descriptions will be given regarding pressure of the circulation liquid in each of the stages in the filtration device with reference to the specific example. In this example, a pressure loss caused by the stream of cross-flow of one separation membrane module is 100 kPa, liquid supply pressure of the circulation pump 11 is 400 kPa, a pressure loss of the liquid supply pipe from the circulation pump 11 to the entrances of the separation membrane modules in series in the first stage is 20 kPa, a pressure loss of the liquid supply pipe from the exits of the separation membrane modules in series in the third stage to the fermentor 1 is 50 kPa, and a pressure loss of the liquid supply pipe for the separation membrane modules in series from the first stage to the second stage and the separation membrane modules in series from the second stage to the third stage is 10 kPa. In this example, pressure of the circulation liquid at the entrances of the separation membrane modules A1, B1, C1, and D1 is reduced as much as a pressure loss of the liquid supply pipe from the circulation pump 11 to the separation membrane modules, thereby being 380 kPa.

Pressure of the circulation liquid at the entrances of the separation membrane modules A2, B2, C2 and D2 is reduced further as much as a pressure loss of the separation membrane modules in series in the first stage and the liquid supply pipe, thereby being 270 kPa.

Pressure of the circulation liquid at the entrances of the separation membrane modules A3, B3, C3 and D3 is reduced further as much as a pressure loss of the separation membrane modules in series in the second stage and the liquid supply pipe, thereby being 160 kPa.

Pressure of the liquid to be filtrated at the exits of the separation membrane modules A3, B3, C3 and D3 is reduced further as much as a pressure loss of the separation membrane modules in series in the third stage thereby being 60 kPa.

There may be a slight difference depending on an individual difference in the separation membrane modules and a difference in the liquid supply pipes. However, the transmembrane pressure difference necessary for filtration ranges approximately from several kPa to 200 kPa. In other words, with the configuration described herein, it is possible to ensure the pressure necessary for filtration in each of the stages of the separation membrane modules by driving the circulation pump 11.

When the stream of the permeated liquid among such separation membrane modules disposed in series is collectively controlled, there is an occurrence of a difference in the transmembrane pressure difference, that is, a difference in pressure of the circulation liquid, as described above. In other words, in this example, a difference of 320 kPa occurs between the lower portions of the separation membrane modules in the lowermost stage and the upper portions of the separation membrane modules in the uppermost stage. In a case where the pressure of the permeated liquid is 0 kPa, the transmembrane pressure difference becomes 380 kPa at the lower portions of the separation membrane modules in the lowermost stage and becomes 60 kPa at the upper portions of the separation membrane modules in the uppermost stage, resulting in a difference of approximately six times therebetween when compared. Although it depends on the characteristics of the separation membrane, when the transmembrane pressure difference and the filtration amount have a relationship of being proportional to each other, it is considered that the difference of approximately six times also occurs in the filtration amounts therebetween, and thus, an overload is applied to the separation membrane modules in the lowermost stage.

It is desirable that the transmembrane pressure difference ranges from several kPa to 200 kPa. When the transmembrane pressure difference is 380 kPa, clogging progresses rapidly. Therefore, there is a need to lower the transmembrane pressure difference by raising pressure of the permeated liquid. However, when the pressure of the permeated liquid increases, the transmembrane pressure difference in the uppermost stage becomes much smaller, and the difference between the filtration amounts of the separation membrane modules becomes larger.

The other means for obtaining driving power which is necessary for performing filtration will be described later.

(B) Intermittent Filtration

Sediments on the separation membrane surface can be removed by the shearing force of a stream of cross-flow. Intermittent filtration is performed by alternately repeating filtration treatment and suspension of the filtration treatment. Particularly, at the time of the suspension of the filtration treatment for suspending filtration, it is preferable that sediments on the separation membrane surface are removed by increasing the shearing force of a stream of cross-flow.

For example, during intermittent filtration in which filtration treatment for nine minutes and the suspension of the filtration treatment for one minute are repeated, a raw material is added to the fermentor as much as the fermentation liquid is reduced through filtration during filtration performed for nine minutes, but since the entire amount of the fermentation liquid is refluxed to the fermentor 1 by the circulation pump 11 and there is no reduced amount of the fermentation liquid during suspension of the filtration held for one minute, no raw material is added to the fermentor. In the continuous-fermentation apparatus 101, when filtration treatment is performed for nine minutes and the suspension of filtration treatment is held for one minute at the same timing in all the separation membrane modules, a raw material is added during the filtration is performed but no raw material is added during the suspension of the filtration treatment. When a raw material is intermittently added, concentration of the raw material in the fermentor 1 becomes unstable, and thus, there is a concern about difficulties in stably performing fermentation. Therefore, in the present embodiment, it is preferable that suspension of filtration is not held at the same time for each of the parallel units of the separation membrane modules. It is preferable that the suspension of the filtration treatment is controlled so as to be not overlapped in the stages with one another and the filtration amounts are adjusted to be equalized.

Descriptions are given in detail by exemplifying continuous fermentation. However, as described in the present embodiment, suppressing a change in the filtration amounts is useful for other purposes as well.

Figure 2:
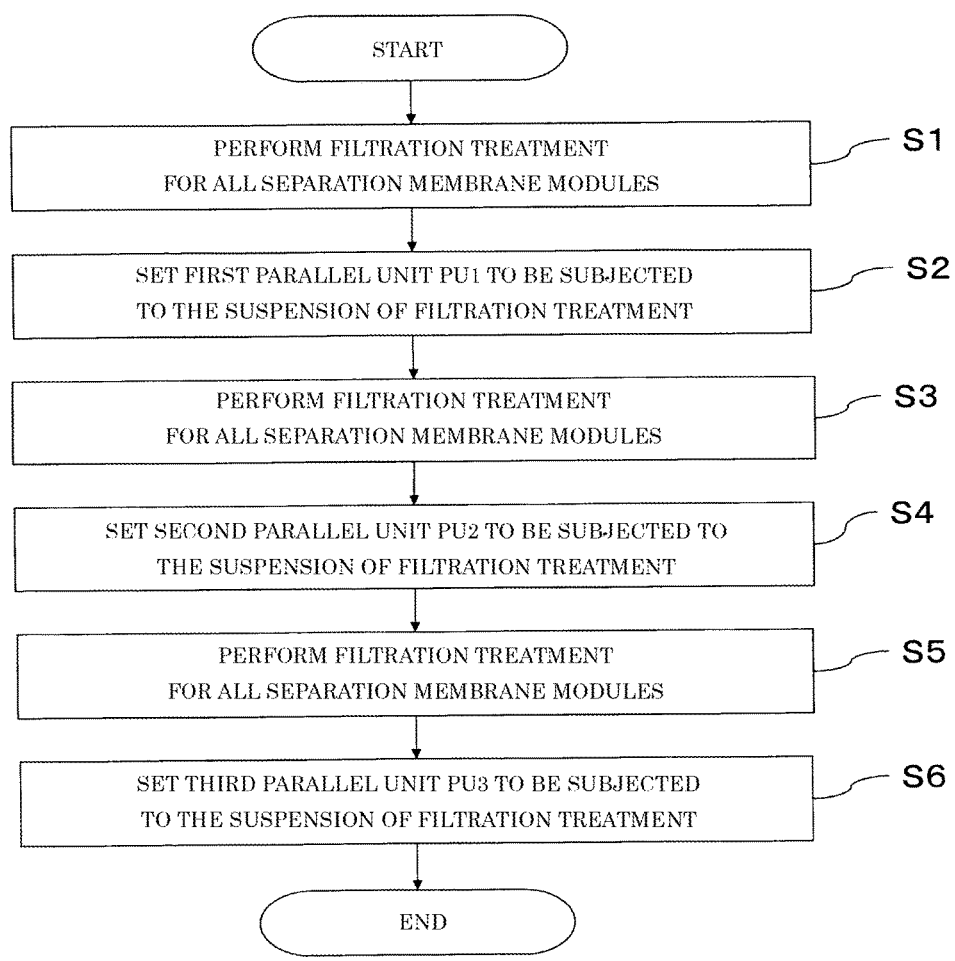
FIG. 2 is a flow chart illustrating intermittent filtration treatment according to the first embodiment.

Intermittent filtration treatment according to the first embodiment will be described with reference to FIG. 2. FIG. 2 is a flow chart illustrating the intermittent filtration treatment according to the first embodiment. In the first embodiment, when performing the intermittent filtration treatment, it is preferable that the intermittent filtration treatment is performed while controlling the timing of the suspension of the filtration treatment for each of the parallel units of the separation membrane modules.

In the first embodiment, for example, controlling of the timing of suspension of the filtration treatment denotes that the suspension of the filtration treatment is performed for the parallel units in at least one stage while filtration treatment is performed for other parallel units. Preferably, the suspension of the filtration treatment is controlled so as to be not overlapped in the parallel units with one another. When performing intermittent filtration so as to cause the suspension of the filtration treatment to be not overlapped in the parallel units with one another, the filtration treatment is firstly performed for all the separation membrane modules (Step S1). In order to perform the filtration treatment for all the separation membrane modules, the filtration control valves 131, 132, and 133 are opened, the filtration pumps 121, 122, and 123 are operated, and the fermentation liquid is supplied to each of the series units (SU1 to SU4) of the separation membrane modules by the circulation pump 11, thereby being filtrated. In all the steps described below, the fermentation liquid which is not filtrated through the separation membrane modules is subjected to cross-flow to the fermentor 1.

After a predetermined time elapsed (for example, after two minutes), the first parallel unit PU1 is subjected to the suspension of the filtration treatment (Step S2). When the first parallel unit PU1 is subjected to the suspension of the filtration treatment and the filtration treatment is performed for the parallel units in other stages, the filtration control valves 132 and 133 are opened, the filtration control valve 131 is closed, the filtration pumps 122 and 123 are operated, the filtration pump 121 is suspended, and the fermentation liquid is supplied to the separation membrane modules by the circulation pump 11, thereby being filtrated in the second and third parallel units PU2 and PU3. The first parallel unit PU1 is subjected to the suspension of the filtration treatment, and sediments of the membranes are removed by the fermentation liquid of cross-flow inside the separation membrane modules.

After a predetermined time elapsed (for example, after one minute), the suspension of the filtration treatment for the first parallel unit PU1 ends, and the filtration treatment is performed for the separation membrane modules in all the stages disposed in series (Step S3). The filtration control valve 131 is switched to be opened, and filtration treatment is performed for the separation membrane modules in all the stages by operating the filtration pump 121.

After a predetermined time elapsed (for example, after two minutes), the second parallel unit PU2 is subjected to the suspension of the filtration treatment (Step S4). When the second parallel unit PU2 is subjected to the suspension of the filtration treatment and the filtration treatment is performed for the parallel units in other stages, the filtration control valve 132 is switched to be closed and the filtration pump 122 is suspended, thereby being filtrated in the first and third parallel units PU1 and PU3. The second parallel unit PU2 is subjected to the suspension of the filtration treatment. Sediments of the membranes are removed by the fermentation liquid of cross-flow inside the separation membrane modules.

After a predetermined time elapsed (for example, after one minute), the suspension of the filtration treatment for the second parallel unit PU2 ends, and the filtration treatment is performed for the separation membrane modules in all the stages (Step S5). The filtration control valve 132 is switched to be opened, and the filtration treatment is performed for the separation membrane modules in all the stages by operating the filtration pump 122.

After a predetermined time elapsed (for example, after two minutes), the third parallel unit PU3 is subjected to the suspension of the filtration treatment (Step S6). When the third parallel unit PU3 is subjected to the suspension of the filtration treatment and the filtration treatment is performed for the parallel units in other stages, the filtration control valve 133 is switched to be closed and the filtration pump 123 is suspended, thereby being filtrated in the first and second parallel units PU1 and PU2. The third parallel unit PU3 is subjected to the suspension of the filtration treatment. Sediments of the membranes are removed by the fermentation liquid of cross-flow inside the separation membrane modules.

By repeating the intermittent filtration treatment in this manner, the suspension of the filtration treatment can be controlled so as to be not overlapped in the parallel units with one another.

Since it is expected that contaminants on the membrane surfaces in the separation membrane modules are removed by the circulation pump 11 with the shearing force of a stream of cross-flow, it is preferable that there is a stream of cross-flow even during the suspension of the filtration.

In the apparatus in FIG. 6, all the separation membrane modules of the filtration device 204 are subjected to suspension of filtration, and on the other hand, filtration can be continued for the filtration device 205 in its entirety or for a portion of the separation membrane modules. However, it is preferable to perform the suspension of the filtration treatment with respect to each of the separation membrane module parallel units, since variation in the filtration amounts is small.

3. Cleaning Step (A) Overview of Cleaning Step

The method for manufacturing a chemical may include the cleaning step for the separation membranes. The cleaning step is not limited to a specific method. However, it is preferable that sediments such as cells on the separation membrane are removed by the shearing force of cross-flow on surfaces of the separation membranes on the non-permeation sides by performing the intermittent filtration treatment in which filtration treatment and the suspension of filtration treatment are repeated. Moreover, it is preferable to suspend cleaning (normal cleaning) or filtration in which the cleaning liquid is caused to pass through from the non-permeation sides to the permeation sides, and to perform cleaning (backwashing) in which the cleaning liquid is caused to pass through from the permeation sides to the non-permeation sides of the separation membranes or to perform submerging with the backwashing liquid, thereby cleaning the separation membranes. When the intermittent filtration treatment is performed by using the plurality of separation membrane modules, it is preferable to control the suspension of the filtration treatment for the plurality of separation membrane modules disposed in parallel or in series so as to be not overlapped so that filtration is not entirely suspended.

When filtration is suspended and the separation membranes are cleaned, gas may be continuously or intermittently supplied to the modules at the same time. When the separation membranes are subjected to the backwashing, a stream of cross-flow may be either present or absent. When the backwashing is performed while a stream of cross-flow is present, the backwashing may be performed at pressure greater than a total sum of pressure of cross-flow and a differential pressure between the separation membranes.

(B) Backwashing

Here, the backwashing is a method of removing contaminants on the membrane surface by supplying the cleaning liquid from the permeation sides of the separation membranes to the fermentation liquid sides which is the non-permeation sides. The backwashing can be performed by using water or the cleaning liquid. As the cleaning liquid, water including an alkali, an acid, an oxidizing agent, or a reducing agent can be used within a range in which fermentation is not significantly impaired. As the cleaning liquid within a range in which the effect of the invention is not impaired, in a case of sodium hypochlorite, for example, it is preferable to use the cleaning liquid of which effective chlorine concentration ranges from 10 ppm to 5,000 ppm, and in cases of sodium hydroxide and calcium hydroxide, for example, it is preferable to use the cleaning liquid of which pH value ranges from 10 to 13. If the concentration exceeds the above-mentioned range, damage to the separation membranes and negative effects to cells are conceivable. If the concentration is less than the above-mentioned range, there is a concern about deterioration of the effect of membrane cleaning.

Here, as an example of the alkali, calcium hydroxide, sodium hydroxide, and the like can be exemplified. As an example of the acid, an oxalic acid, a citric acid, a hydrochloric acid, a nitric acid, and the like can be exemplified. As an example of the oxidizing agent, hypochlorite, hydrogen peroxide, and the like can be exemplified. As an example of the reducing agent, inorganic reducing agents such as sodium bisulfite, sodium sulfite, sodium thiosulfate can be exemplified. The backwashing liquid can be used at a high temperature.

In the backwashing, since the cleaning liquid is caused to permeate from the permeation sides of the separation membranes to the non-permeation sides thereof, it is preferable that the cleaning liquid includes no solid. For example, in a case where the concentration of calcium hydroxide is greater than approximately 0.01 N, the calcium hydroxide exists as a solid without being dissolved so that calcium hydroxide with such a high concentration is not suitable for the backwashing liquid.

If the pH value of the fermentation liquid deviates from the proper range even momentarily, there are concerns about deterioration in fermentation results obtained during the period, and deterioration in activation of cells. Therefore, when an alkali or an acid is added when performing the backwashing, there is a need to be separately provided with a pH adjusting control device in order to control the pH value of the fermentation liquid within the proper range.

Since the backwashing is performed so as to prevent the transmembrane pressure difference of the separation membranes from chronologically rising, it is preferable to be cyclically performed at suitable time intervals. The cycle of the backwashing can be determined based on the transmembrane pressure difference and variation of the transmembrane pressure difference. The cycle of the backwashing ranges from 0.5 times to 12 times per hour, and more preferably ranges from 1 time to 6 times per hour. If the cycle of the backwashing exceeds the range, there is a concern of damage to the separation membranes, thereby resulting in a reduced filtration time. If the cycle is smaller than the range, the cleaning effect cannot be sufficiently obtained sometimes.

It is preferable that a speed of the backwashing performed with the backwashing liquid ranges from 0.5 times to 10 times the speed of membrane filtration, and more preferably ranges from one time to 5 times thereof. As the speed of the backwashing is equal to or less than 10 times the speed of the membrane filtration, the concern of damage to the separation membranes can be reduced, and as the speed thereof is equal to or greater than 0.5 times thereof, the cleaning effect can be sufficiently obtained.

A time for the backwashing performed with the backwashing liquid can be determined based on the cycle of the backwashing, the transmembrane pressure difference, and variation of the transmembrane pressure difference. The time for the backwashing ranges from 5 seconds to 300 seconds per cycle, and more preferably ranges from 30 seconds to 120 seconds per cycle. If the time for the backwashing exceeds the range, there is a concern of damage to the separation membranes, and if the time is less than the range, the cleaning effect cannot be sufficiently obtained sometimes.

(C) Method of Cleaning Membranes in Plurality of Lines of Modules in Series

In the filtration device including the plurality of separation membrane modules which are disposed in a matrix, when one cleaning liquid valve is provided for one parallel unit as those in the third and fourth embodiments, each of the stages can be individually cleaned. When two or more cleaning liquid valves are provided for one parallel unit, the plurality of separation membrane modules included in one parallel unit can be divided into two or more groups and cleaned.

When submersion cleaning of the membranes is performed, cross-flow filtration is stopped once with respect to the separation membrane module which is a cleaning target, and then, for example, submersion cleaning for the membranes can be performed by supplying the cleaning liquid to the membranes for each of the parallel units.

Descriptions will be given regarding the backwashing for the fermentation apparatus 103 of a third embodiment.

When performing the backwashing during suspension of filtration, for example, during nine minutes of filtration, a raw material as much as the amount of the fermentation liquid reduced through filtration is added to the fermentor. However, for one minute in which the backwashing is performed during the suspension of the filtration, the cleaning liquid for the backwashing flows into the fermentor 1. Therefore, the amount of the fermentation liquid in the fermentor 1 increases. When the amount of the liquid in the fermentor 1 exceeds the setting value, no raw material is added to the fermentor 1 until the increased amount of the backwashing liquid is cancelled. When all the plurality of separation membrane modules repeat the filtration for nine minutes, and the suspension of the filtration and the backwashing for one minute at the same timing, the raw material is added intermittently so that the concentration of the raw material in the fermentor 1 is not in a stable state, and thus, there is a concern about difficulties in realizing stable fermentation. Therefore, it is effective to adjust the filtration amount so as to be equalized by shifting the timing so that the backwashing is not performed for each of the stages of the separation membrane modules at the same time.

Figure 5:
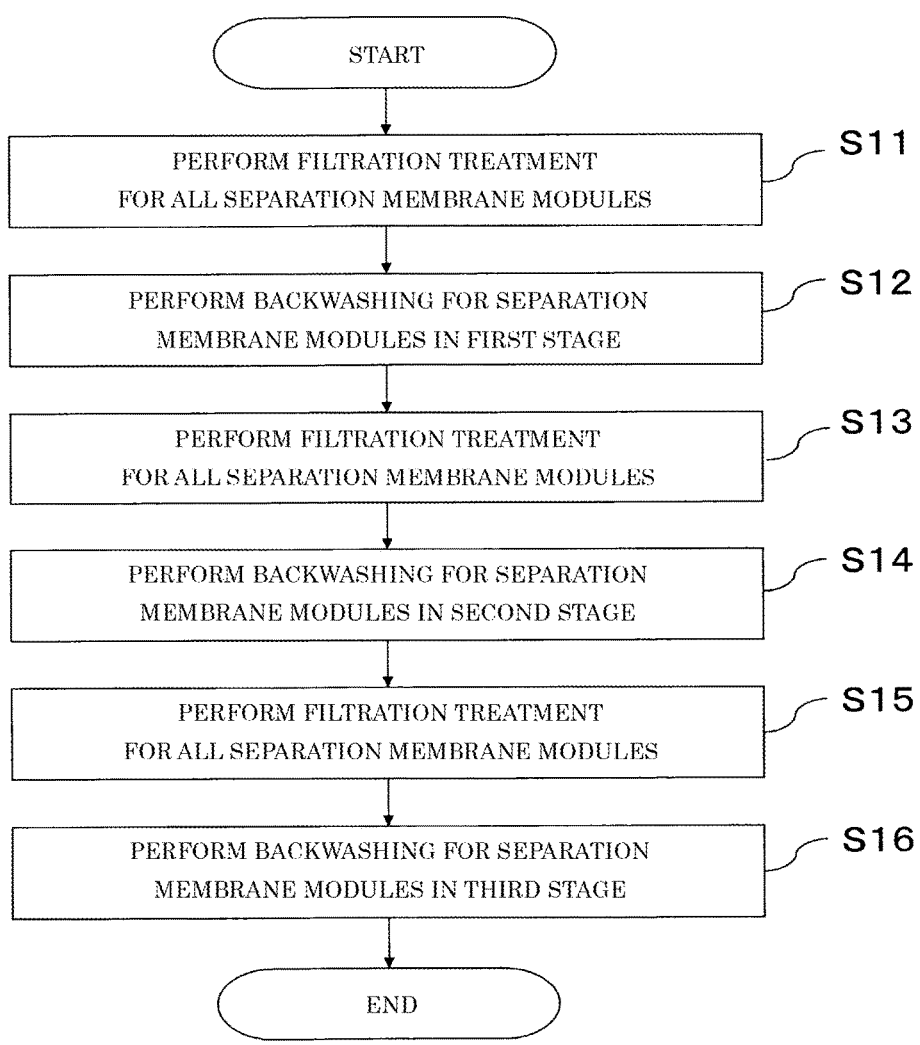
FIG. 5 is a flow chart illustrating the intermittent filtration treatment according to the third embodiment of the present invention.

With reference to FIG. 5, descriptions will be given regarding the intermittent filtration treatment in a case where the backwashing is performed during the suspension of the filtration treatment in the third embodiment. FIG. 5 is a flow chart illustrating the intermittent filtration treatment of the third embodiment in the present invention. When the backwashing is performed for the separation membrane modules disposed in series during the suspension of the filtration, it is preferable to perform the intermittent filtration treatment by controlling the timing of the backwashing for each of the stages of the separation membrane modules disposed in series. In the third embodiment, for example, controlling of the timing of the backwashing denotes that the backwashing treatment for at least one stage of the separation membrane modules disposed in series is performed during the filtration treatment performed for the separation membrane modules in other stages. Preferably, the backwashing treatment for each of the stages of the separation membrane modules disposed in series is controlled so as to be not overlapped with one another. When performing intermittent filtration so as to cause the backwashing treatment for each of the stages of the separation membrane modules disposed in series to be not overlapped with one another, filtration treatment is firstly performed for all the separation membrane modules (Step S11).

In order to perform filtration treatment for all the separation membrane modules, the filtration control valves 131, 132, and 133 are opened, the filtration pumps 121, 122, and 123 are operated, and the fermentation liquid is supplied to the separation membrane modules by the circulation pump 11, thereby being filtrated. In all the steps described below, the fermentation liquid which is not filtrated through the separation membrane modules disposed in series is refluxed to the fermentor 1.

After a predetermined time elapsed (for example, after two minutes), the first parallel unit PU1 is subjected to the backwashing treatment (Step S12). When the first parallel unit PU1 is subjected to the backwashing treatment and filtration treatment is performed for other parallel units, the filtration control valves 132 and 133 are opened, the filtration control valve 131 is closed, the filtration pumps 122 and 123 are operated, the filtration pump 121 is suspended, and the fermentation liquid is supplied to each of the series units SU1, SU2, SU3 and SU4 by the circulation pump 11.

Furthermore, as the cleaning liquid valves 152 and 153 are closed, the cleaning liquid valve 151 is opened, and the cleaning liquid pump 14 is operated, the second and third parallel units PU2 and PU3 are subjected to filtration and the first parallel unit PU1 is subjected to the backwashing. In the first parallel unit PU1, the cleaning liquid is supplied to the permeated liquid sides of the first parallel unit PU1 by the cleaning liquid pump 14, and the cleaning liquid is filtrated through the non-permeation sides, thereby removing sediments on the membranes.

After a predetermined time elapsed (for example, after one minute), the backwashing treatment for the first parallel unit PU1 ends, and filtration treatment is performed for all the separation membrane modules (Step S13). The cleaning liquid valve 151 is switched to be closed, the cleaning liquid pump 14 is suspended, the filtration control valve 131 is switched to be opened, and the filtration pump 121 is operated, thereby performing the filtration treatment for all the separation membrane modules.

After a predetermined time elapsed (for example, after two minutes), the second parallel unit PU2 is subjected to the backwashing treatment (Step S14). When the second parallel unit PU2 is subjected to the backwashing treatment and filtration treatment is performed for other stages, the filtration control valve 132 is switched to be closed, the filtration pump 122 is suspended, the cleaning liquid valve 152 is switched to be opened, and the cleaning liquid pump 14 is operated, and thus, the first and third parallel units PU1 and PU3 disposed in series are subjected to filtration, and the second parallel unit PU2 is subjected to the backwashing. In the second parallel unit PU2, the cleaning liquid is supplied to the permeated liquid sides of the second parallel unit PU2 by the cleaning liquid pump 14, and the cleaning liquid is filtrated through the non-permeation sides, thereby removing sediments on the membranes.

After a predetermined time elapsed (for example, after one minute), the backwashing treatment for the second parallel unit PU2 ends, and filtration treatment is performed for all the separation membrane modules (Step S15). The cleaning liquid valve 152 is switched to be closed, the cleaning liquid pump 14 is suspended, the filtration control valve 132 is switched to be opened, and the filtration pump 122 is operated, thereby performing the filtration treatment for all the separation membrane modules.

After a predetermined time elapsed (for example, after two minutes), the third parallel unit PU3 is subjected to the backwashing treatment (Step S16). When the third parallel unit PU3 is subjected to the backwashing treatment and filtration treatment is performed for other stages, the filtration control valve 133 is switched to be closed, the filtration pump 123 is suspended, the cleaning liquid valve 153 is switched to be opened, and the cleaning liquid pump 14 is operated, and thus, the first and second parallel units PU1 and PU2 are subjected to filtration, and the third parallel unit PU3 is subjected to the backwashing. In the third parallel unit PU3, the cleaning liquid is supplied to the permeated liquid sides of the third parallel unit PU3 by the cleaning liquid pump 14, and the cleaning liquid is filtrated through the non-permeation sides, thereby removing sediments on the membranes.

The backwashing treatment can be controlled so as to be not overlapped in each of the parallel units of the separation membrane modules with one another by repeating the intermittent filtration treatment in such a manner.

Hereinbefore, descriptions are given regarding a case of performing the backwashing for the membranes during the suspension of the filtration treatment in the intermittent filtration treatment. However, the backwashing is not necessarily performed during entire the suspension of the filtration treatment in the intermittent filtration treatment. As long as the separation membranes can be prevented from being blocked, the backwashing may be performed only during a part of the suspension of the filtration treatment. For example, intermittent filtration treatment 1 (the suspension of the filtration treatment for each of the stages of the separation membrane modules disposed in series is controlled so as to be not overlapped with one another) illustrated in FIG. 2, and intermittent filtration treatment 2 (the backwashing treatment for each of the stages of the separation membrane modules disposed in series is controlled so as to be not overlapped with one another) illustrated in FIG. 5 may be alternately repeated. Otherwise, the treatment may be repeated, for example, the intermittent filtration treatment 1 is continuously performed twice, and the intermittent filtration treatment 2 is performed once thereafter. The combination may be determined in consideration of filtration conditions such as performance of the separation membrane module, the filtration treatment target, and the amount of filtration treatment. Otherwise, no backwashing may be performed during the suspension of the filtration treatment in the intermittent filtration treatment, and the backwashing may be performed in a different step so that the backwashing step for the separation membrane modules is controlled so as to be not overlapped with one another.

In the second embodiment, as described above, as the timing of the suspension of the filtration treatment or the backwashing treatment for the separation membrane modules is controlled to be dispersed, variation in the amount of the fermentation liquid and variation in the supply amount of the culture medium is reduced. Therefore, fermentation can be stably performed and chemicals can be collected at a high collect rate.

Similar to intermittent filtration, as the separation membrane modules are subjected to the backwashing for each of the parallel units instead of each of the series units, it is possible to share the equipment related to the backwashing among the separation membrane modules inside the parallel units, and thus, the equipment cost can be reduced.

(D) Submersion Cleaning

When performing the backwashing, filtration is suspended once, and then, the separation membrane can be submerged in the backwashing liquid. The submersion time can be determined based on a submersion cleaning cycle, the transmembrane pressure difference, and variation of the transmembrane pressure difference. The submersion time ranges preferably from one minute to 24 hours per event and ranges more preferably from ten minutes to 12 hours per event.

In the continuous-fermentation apparatus, when there are a plurality of lines of the separation membranes and the separation membranes are subjected to submersion cleaning with the backwashing liquid, it can be preferably employed that the lines are switched so as to allow only a portion thereof to be subjected to submersion cleaning so that filtration is not entirely suspended.

4. Controlling of Filtrating Operation

With reference to FIGS. 1, 7, and 8, descriptions will be given regarding the specific example of the operation of controlling a filtrating operation in the first embodiment. The operation can be applied to the filtration devices of all the embodiments described in this Description.

FIG. 8 is a flow chart illustrating a flow of an example of the operation of controlling a filtrating operation in the filtration device 201. FIG. 8 is illustrated on the premise that a worker inputs a criterial setting value into the control device, for each of the stages. However, as described above, the setting value is set so as to avoid an occurrence of bias in the filtration flow rate in each of the stages.

The filtrating operation control device controls the filtration flow rate of each of the stages to be close to the filtration flow rate of the setting value. In addition, each of the filtrating operation control devices 51 to 53 illustrated in FIG. 1 includes the functional blocks similar to those in FIG. 7, a storage device corresponding to the memory 501c stores the extent to which pressure of the permeated liquid is to be raised or reduced (the magnitude of the driving power of the filtration pump) while being associated with the difference between the setting value of the flow rate of the permeated liquid and the flow rate of the permeated liquid in each of the stages.

First, a setting flow rate F0_1 of the permeated liquid in the first stage is read by the input section 501a (Steps S21 and S22). The setting flow rate F0_1 of the permeated liquid is temporarily stored in the memory 501c of the control unit 501.

Subsequently, an output value F1 of the permeated liquid flow rate sensor in the first stage is read by the control unit 501 (Step S23). Then, the output value F1 is also temporarily stored in the memory 501c. Reading of the output value F1 is repeated for a predetermined time (for example, for one minute) ("No" in Step S24, Step S23). After a predetermined time elapsed, an average value F1_ave of the stored output values F1 is calculated and is stored in the memory 501c ("Yes" in Step S24, Step S25). The determination section 501b reads the setting flow rate F0_1 in the first stage and the average value F1_ave of the flow rate from the memory 501c, calculates the flow rate difference (F0_1−F1_ave), and compares the calculation result and a threshold value $\alpha$.

When $\alpha$<(F0_1−F1_ave) is satisfied ("Yes" in Step S26), the pump control section 501d increases the driving power of the filtration pump 121 in the first stage (Step S27). When −$\alpha$≤(F0_1−F1_ave)≤$\alpha$ is satisfied ("No" in Step S26, "Yes" in Step S30), the driving power of the filtration pump 121 in the first stage is retained (Step S31). When (F0_1−F1_ave)<−$\alpha$ is satisfied, the driving power of the filtration pump 121 is reduced ("No" in Step S26, "No" in Step S30, Step S32). In this case, changed amounts of the driving power of the filtration pump may be stored in the memory 501c in accordance with the values of (F0_1−F1_ave) by being divided into several levels.

In this manner, controlling of a filtrating operation of the separation membrane modules in the first stage is completed. Therefore, subsequently, controlling thereof in the second stage is performed (Step S28, "No" in Step S29, S22).

When controlling of the third stage is completed, a series of control operations end ("Yes" in Step S27, End).

The threshold value α is preferably equal to or less than 10% of the setting flow rate, more preferably equal to or less than 5% of the setting flow rate, and still more preferably equal to or less than 1% of the setting flow rate.

The timing for performing the operation of controlling a filtrating operation is not particularly limited. For example, at the time when starting to use the filtration device, or at the time when the operation period reaches a predetermined period, the control operation may be performed. From a view point of the step management, it is preferable to frequently perform the above-described control operation. For example, a worker in charge of the step management may perform the control operation once a day, or automatic control may be performed in sequence, thereby performing the control operation every 10 minutes.

With regard to controlling of pressure of the permeated liquid, in addition to adjusting the driving power of the filtration pump, the pressure can be controlled by adjusting the degree of the open state of the filtration control valve. In other words, as the degree of the open state of the filtration control valve is increased, pressure of the permeated liquid can be reduced, and thus, it is possible to attain an effect similar to that of increasing the driving power of the filtration pump.

The control operation may be performed by using an output value of the permeated liquid pressure sensor in place of the permeated liquid flow rate sensor. The permeated liquid pressure sensor can measure the transmembrane pressure difference by reading the values at the times of filtrating operation and suspension of the filtration and calculating the difference therebetween. The output value used in the control operation may be any one of the value of pressure of the permeated liquid and the value of the transmembrane pressure difference which is calculated based on the pressure of the permeated liquid obtained through the above-described method as long as both the setting value and the detection value are unified into one therebetween.

In this manner, the filtrating operation control device can collectively control pressure of the permeated liquid in the plurality of separation membrane modules to which the filtrating operation control device is connected so as to reduce the difference between the filtration flow rates of the separation membrane modules in the stages different from each other. Similar controlling can be collectively performed so as to reduce the difference in the transmembrane pressure difference.

5. Sterilization or Disinfection Step (5-1) Overview of Sterilization and Disinfection When unwanted microorganisms are mixed into the fermentation liquid, manufacturing efficiency of a chemical is deteriorated due to deterioration of fermentation efficiency, foaming occurred inside the fermentor, and the like. Therefore, in order to prevent unwanted microorganisms from being mixed in, it is preferable that the fermentor, the separation membrane, and the peripheral equipment are sterilized or disinfected before performing fermentation so that unwanted microorganisms are prevented from being mixed in (contamination).

As a sterilization method, flame sterilization, dry heat sterilization, boiling sterilization, steam sterilization, ultraviolet sterilization, gamma sterilization, gas sterilization, and the like can be exemplified. As the sterilization method, steam sterilization is particularly preferable. In addition, as a disinfection method, warm water disinfection is preferable.

According to steam sterilization or warm water disinfection, for example, even a module has a complicated inner structure, such as a hollow fiber membrane module, the module can be sufficiently sterilized.

Moreover, according to steam sterilization and warm water disinfection, a membrane is unlikely to be dried and is effective against microorganisms which have acquired resistance to chemicals.

(5-2) Steam Sterilization

Generally, it is preferable to perform steam sterilization at 121° C., for 15 minutes to 20 minutes. When steam sterilization is performed with equipment on the industrial scale, for example, sterilization can be performed by supplying saturated water vapor of 125° C. to the fermentor, the separation membrane modules, and the peripheral equipment; heating each item of the equipment up to 121° C., and retaining the temperature for 20 minutes or longer.

When performing steam sterilization, steam may be supplied to the non-permeation sides of the separation membrane modules and may be supplied to the permeation sides thereof. With regard to an external pressure-type hollow fiber membrane, it is general to supply steam to the non-permeation sides. Depending on the type of the membrane, sterilization may be performed on not only the non-permeation sides but also the permeation sides by ventilating steam from the non-permeation sides to the permeation sides.

Descriptions will be given below regarding an aspect of the step of sterilizing the filtration device which includes the plurality of lines of the modules in series and has been described in Section I above, by particularly exemplifying steam sterilization of the filtration device which has the structure illustrated in FIG. 1.

When steam sterilization is performed, steam drainage is generated due to heat exchange. In order to cause the steam drainage to be easily discharged, it is preferable to supply steam to the module through an upper portion and to discharge the steam through a lower portion thereof when performing steam sterilization. Accordingly, steam can be supplied to all the modules connected in series, by supplying steam from the modules in the uppermost stage among the modules connected in series. Discharging of drainage will be described later.

When performing steam sterilization, steam may be supplied from the liquid to be filtrated sides of the separation membrane modules or steam may be supplied from the permeation sides. With regard to the external pressure-type hollow fiber membrane, steam may be supplied from the liquid to be filtrated sides, and sterilization may be performed by heating the liquid to be filtrated sides up to a predetermined temperature. Furthermore, depending on the type of the membrane, sterilization may also be performed on the permeation sides by ventilating steam from the liquid to be filtrated sides to the permeation sides.

As the separation membrane modules are vertically disposed (so as to cause the longitudinal direction to be along the vertical direction), the following advantages are achieved. First, when the liquid to be filtrated is applied from below, it is easy to fill the inside of the module with the liquid to be filtrated without accumulating air. As a result thereof, the membrane area can be effectively used. In addition, the liquid to be filtrated can be prevented from foaming, and cells included in the liquid to be filtrated are unlikely to be damaged. Furthermore, when the separation membrane modules are connected in series and the series of the connected separation membrane modules are collectively sterilized, drainage can be efficiently discharged.

In a specific aspect, a steam supply device (not illustrated) is connected to a steam supply port (not illustrated) which is provided on the reflux line 60. As the filtration device 201 is connected to the reflux line 60, the steam supply device can supply steam to all the separation membrane modules via one steam supply port.

However, even though the device is configured to be able to supply steam to all the series units at a time via one steam supply port, when there are many series units, it is preferable that the series units are divided into a plurality of groups, and first, steam is caused to pass through the series units for each group, and thereafter, steam sterilization for the series units all together is performed at the same time. In this manner, as steam is caused to pass through, even in the case where many series units are provided, the series unit which is far away from the steam supply port can also be able to be prevented from occurring sterilization failure.

Descriptions will be given specifically by exemplifying a case where the steam supply port is provided on the downstream side farther than a pipe 61 which is connected to the reflux line 60 farthest on the downstream side in a flowing direction of the circulation liquid, on the reflux line 60. In the configuration, when steam is caused to pass through the series units SU1, SU2, SU3 and SU4 all together at the same time from the steam supply port, the steam reaches early in the order of the series units SU1, SU2, and SU3 from the side close to the steam supply port. The timing when the steam reaches the series unit SU4 farther from the steam supply port is the latest among all the series units. Inside all the series units, there may be air which exists before the supply of steam starts. However, since steam quickly passes through the series unit SU1 from the upper portion to the lower portion, air is easily pushed out. Incidentally, when steam reaches the series unit SU4, the steam which has passed through the series unit SU1 reaches the lower portion of the filtration device 201, and pressure inside the pipe at the lower portion of the filtration device 201 may be already high due to the steam. Even though air inside the series unit SU4 is pushed down by the steam supplied from above, since the pressure inside the pipe at the lower portion is already high, air is not pushed out and remains inside the series unit SU4. The portion where air remains is unlikely to be heated up so that there is a concern of an occurrence of sterilization failure.

Therefore, as described above, for example, in the configuration of FIG. 1, steam is caused to pass through the series units SU1 and SU2 first, and then, the supply of steam to the series units SU1 and SU2 is temporarily suspended. Thereafter, steam is caused to pass through the series units SU3 and SU4. After steam passes through each of the series units, there is no remaining air which exists before steam is ventilated. Therefore, even though steam restarts to be supplied to the series units all together at the same time, sterilization failure is unlikely to occur.

The number of the lines of the separation membrane module series units to which steam can be supplied at a time can be determined by performing a ventilation test of steam in advance and checking for whether or not each portion of the separation membrane modules is heated up to the set temperature for steam sterilization.

In this manner, in the filtration device including the plurality of series units, steam is supplied from ends on one side of the separation membrane modules connected in series, and thus, sterilization can be performed for a series of the separation membrane modules connected thereto.

(5-3) Drainage Discharge

Steam is supplied through the upper portion of the matrix formed with the plurality of separation membrane modules, and steam drainage is discharged through the lower portion thereof.

In the configuration illustrated in FIG. 1 and the like, between the two separation membrane modules connected in series via the entrance for the liquid to be filtrated, drainage generated inside the module at the upper portion (that is, on the upstream side in the flowing direction of steam) passes through the entrance for the liquid to be filtrated of the module and flows inside the separation membrane module at the lower portion through the exit for the non-permeated liquid of the separation membrane module at the lower portion. In this manner, all drainage which flows inside the separation membrane modules of which the non-permeation sides are connected in series are collected in the separation membrane modules in the lowermost stage (for example, the separation membrane modules A1, B1, and the like), thereby being discharged. In this manner, in the series units, drainage in one series unit can be collectively discharged through the modules in the lowermost stage. As a result thereof, it is possible to reduce the size of the equipment for operation, and operation cost.

When a large amount of drainage stays inside the module, steam does not pervade the place where drainage exists, thereby causing a case of difficulties in heating up to or greater than a predetermined temperature of sterilization. Therefore, it is preferable that the longitudinal direction of the separation membrane module is perpendicular to a horizontal direction (that is, parallel to the vertical direction) or is obliquely disposed with respect to the horizontal direction. It is because drainage is promptly discharged in that manner.

Specifically, it is preferable that the longitudinal direction of the separation membrane module is perpendicular or oblique with respect to the horizontal direction. In other words, it is preferable that an angle between the longitudinal direction of the separation membrane module and the horizontal direction ranges from 1° to 90°. The angle of the separation membrane module will be described later in detail.

When a drainage discharge port is located at a bottom portion of the separation membrane module, drainage can be promptly discharged.

The present invention is not limited to the embodiments disclosed in this Description. The plurality of steam supply devices may be connected to one filtration device, or the plurality of steam supply ports may be provided to one filtration device. In addition, the position of the steam supply port is not limited to particular positions.

(3) Case of Warm Water Disinfection

Generally, when performing warm water disinfection, liquid-passing of warm water at a hot temperature ranging approximately from 70° C. to 90° C. is performed for each of the separation membrane modules for a predetermined time, for example, for one hour, thereby performing disinfection. In this case, in order to prevent air and the like from remaining inside the separation membrane modules or the pipes, for example, in the filtration device 201 of FIG. 1, warm water is supplied through the lower portion of the unit of the filtration device 201, and the warm water is discharged through the upper portion of the unit of the filtration device 201. Similar to steam sterilization, when air remains inside the separation membrane module to which warm water is supplied late and liquid-passing of warm water is performed for other separation membrane modules, the remaining air may be unlikely to be discharged. Therefore, the series units may be suitably divided into groups by several units, and warm water may be supplied for each of the groups.

For example, in a case of FIG. 1, the series units SU1 and SU2 are ventilated with warm water first, and then, warm water supplied to the series units SU1 and SU2 is temporarily suspended. Thereafter, liquid-passing of warm water is performed for the series units SU3 and SU4. After performing liquid-passing of warm water for each of the series units, there is no remaining air which exists before liquid-passing of warm water is performed. Therefore, the supply of warm water can be restarted all together at the same time.

III. Other Modification Examples

According to the filtration device that includes the plurality of separation membrane modules each of which separates the liquid to be filtrated into the permeated liquid and the non-permeated liquid, and is provided with the series non-permeated liquid flow channel that forms the series unit by connecting the non-permeation sides of the plurality of separation membrane modules in series and the parallel permeated liquid flow channel that forms the parallel unit by connecting the permeation sides of the plurality of separation membrane modules in parallel, simplification of the equipment can be realized.

In addition, according to the filtration device that includes the plurality of separation membrane modules each of which separates the liquid to be filtrated into the permeated liquid and the non-permeated liquid, and is provided with the above-described series non-permeated liquid flow channel and the filtrating operation control device that controls at least one of the filtration flow rate and the transmembrane pressure difference of the separation membrane modules by collectively controlling pressures of the permeated liquids flowing out from the plurality of separation membrane modules, simplification of the equipment can also be realized.

The filtration devices according to the above-described embodiments described with reference to FIG. 1 and the like are examples of the filtration devices.

As illustrated in FIG. 1 and the like, one series non-permeated liquid flow channel is acceptable as long as the series non-permeated liquid flow channel connects a portion among the plurality of separation membrane modules included in one filtration device, that is, at least two separation membrane modules therebetween. In other words, one filtration device may have the plurality of series units, or one filtration device may have a separation membrane module which is included in the series unit and a separation membrane module which is not included in the series unit. The parallel permeated liquid flow channel and the parallel unit can also have a similar configuration.

Hereinafter, descriptions will be given in more detail regarding the specific example and the modification example of the configuration of the filtration device.

<Connection Among Separation Membrane Modules and the Like>

In the plurality of series units inside the matrix, the number of the separation membrane modules may be different from that in one another. However, when the number of the separation membrane modules in each of the series units is the same, a pressure loss in each of the series units is mutually approximated, and thus, pressure can be more easily controlled.

The series units may be connected to one another by a pipe. In this case, movement occurs among the series units having cross-flow different from one another. However, the flow rate of cross-flow can be adjusted by providing a valve or the like. Moreover, even though the flow of steam branches off when steam sterilization is performed, air and the like which exist inside each of the separation membrane modules before steam sterilization is performed can be eliminated by causing steam to individually pass through each of the branches. It is preferable that the lengths of the pipes by which the separation membrane modules belonging to the same stage (belonging to the same line) and the separation membrane modules in the later stage thereof are respectively connected in series are substantially the same as one another. In other words, it is preferable that the length of the pipe between the separation membrane module A1 and the separation membrane module A2 of the first series unit SU1 is substantially the same as the length of the pipe between the separation membrane module B1 and the separation membrane module B2 of the second series unit SU2.

However, for example, the required membrane area may vary due to improved performance of the separation membrane modules, a changed filtration amount, and the like. In other words, the number of the separation membrane modules may be reduced from the number thereof set at the stage of designing the apparatus due to reduction of cost, and the like. When the number of the separation membrane modules is reduced in one series unit as compared to the number assumed at the stage of designing the apparatus, for example, the pressure loss in the series unit can be adjusted so as to be equivalent to that of the original series unit by changing the diameter of the pipe connecting the separation membrane modules in series or providing the orifice in the pipe. Moreover, when one series unit is entirely omitted, it is possible to similarly generate a suitable pressure loss by changing the diameter of the pipe or utilizing the orifice.

When the number of the separation membrane modules is increased as compared to that at the initial stage of the design, the number of modules per series unit may be increased, or the number of the series units may be increased.

When the filtrating operation control device and the like are shared among the modules connected in parallel, with regard to all the separation membrane modules in each of the stages, the filtrating operation control device and the like may be shared, or the separation membrane modules in each of the stages may be divided into several units so as to share the permeated liquid lines and the like. For example, in FIG. 1, the separation membrane modules A2, B2, C2, and D2 as one parallel unit share filtration lines and the filtrating operation control device 52. However, the separation membrane modules A2 and B2 may be set as one parallel unit, the separation membrane modules C2 and D2 may be set as another parallel unit, and the filtrating operation control devices may be respectively provided so as to correspond thereto.

As described above, it is preferable that the filtration device includes the permeated liquid parallel flow channel, and it is preferable for the permeated liquid parallel flow channel to have the unit-crossing parallel flow channel by which two or more separation membrane modules belonging to the series units different from one another are connected in parallel via the permeated liquid sides thereof.

The separation membrane modules connected by the permeated liquid parallel flow channel form a parallel unit. In FIG. 1, pipes 121, 122, and 123 are the specific examples of the permeated liquid parallel flow channel. In the example of FIG. 1, all the modules included in one parallel unit are disposed in the same stage. Then, pressures of the permeated liquids of the modules included in one parallel unit are collectively controlled.

It is desirable that a difference between lengths of the permeated liquid pipes respectively connected to the separation membrane modules inside one parallel unit is small. Therefore, for example, the modules can be connected to one another in a leader-board manner (that is, in a tree-diagram manner). Specifically, in the configuration of FIG. 1, the separation membrane module A1 and the module B1 are connected to each other by the permeated liquid pipe, and similarly, the module C1 and the module D1 are connected by the permeated liquid pipe. Furthermore, in the exemplified configuration, an intermediate point of the pipe connecting the modules A1 and B1 is connected to an intermediate point of the pipe connecting the modules C1 and D1.

Figure 9:
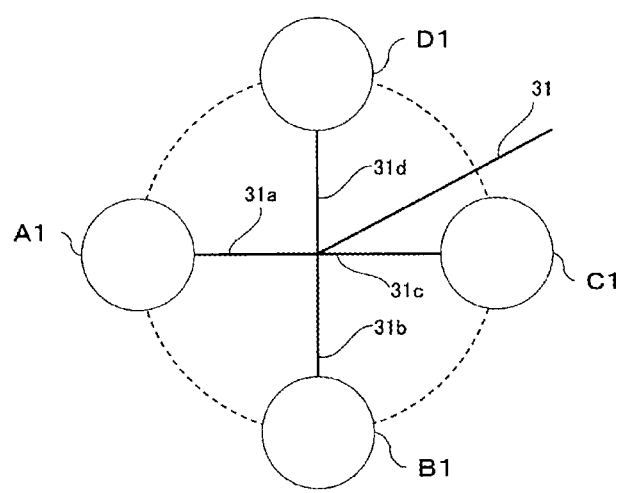
FIG. 9 is a schematic diagram viewed from above a parallel module unit of further embodiment.

For example, in the configuration FIG. 9, the separation membrane modules A1, B1, C1, and D1 are disposed on the circumference (indicated by the dotted virtual line in the diagram) rendered in a horizontal plane direction. Permeated liquid pipes 31a, 31b, 31c and 31d extend from each of the separation membrane modules A1, B1, C1, and D1 toward the center of the circle. At the center of the circle, the permeated liquid pipes are connected to one pipe 31 centered on the circle.

A pressure loss varies due to factors such as the velocity of cross-flow, the structure of the separation membrane module, and the like. The velocity of cross-flow varies due to a measuring gauge such as a flow rate sensor provided on the pipe through which the circulation liquid flows, the valve (and the degree of the open state thereof), the driving power of the circulation pump, and the like. Even though the velocity of cross-flow is the same, pressure of a stream of cross-flow varies depending on the degree of the open state of the valve installed on the liquid to be filtrated side or the magnitude of the driving power of the circulation pump. Therefore, by adjusting the driving power of the pump or the degree of the open state of the valve, pressure of the circulation liquid is raised or reduced so that the transmembrane pressure difference and/or the filtration amount can be adjusted.

It is desirable that the pressure loss of the parallel permeated liquid flow channel connecting the separation membrane modules in the same stage together is small. As the pressure loss of the parallel permeated liquid flow channel is small, the difference in the transmembrane pressure difference between the separation membrane modules in the same stage becomes small. Therefore, collective control performed by one filtrating operation control device is preferably applied. Although the pressure loss varies depending on the type of the separation membrane module, in a case of hollow fiber membrane modules having precise filtration membranes, pressure loss of the parallel permeated liquid flow channel connecting the separation membrane modules in the same stage is preferably equal to or less than 10 kPa, more preferably equal to or less than 5 kPa, and further preferably equal to or less than 1 kPa.

As the configuration for reducing a pressure loss of the permeated liquid pipe, there are considerations such as increasing of the diameter of the pipe, providing no extra measuring gauge and the like which become origins of a pressure loss, reducing the number of the separation membrane modules to be shared, and causing the permeated liquid pipe to branch off into several pipes and to be connected to the separation membrane modules while sharing the filtrating operation control device. It is preferable that the lengths of the permeated liquid pipes between the filtrating operation control device to be shared and each of the separation membrane modules are substantially equal to one another.

When it is difficult to reduce the pressure loss of the permeated liquid pipe, a water head difference may be utilized so as to adjust pressure of the permeated liquid by installing the permeated liquid pipe of the separation membrane module far from the filtrating operation control device at a high position and installing the permeated liquid pipe of the separation membrane module close to the filtrating operation control device at a low position. Otherwise, influences caused by a pressure loss can be eliminated by installing a liquid-passing resistor such as an orifice and a valve on the separation membrane module side (the upstream side) from the merging point of the permeated liquid pipes.

Furthermore, when the separation membrane modules in the stages different from one another are connected to one another among the separation membrane modules belonging to the series units different from one another, influences can be eliminated by installing a liquid-passing resistor such as an orifice which generates a pressure difference between the separation membrane modules on the non-permeated liquid sides or a pressure loss as much as the water head difference.

<Angle of Separation Membrane Module>

As describe above, it is preferable that the separation membrane modules are disposed so as to cause the longitudinal direction thereof to be perpendicular or oblique with respect to the horizontal direction. The term "oblique" denotes that the disposition deviates from the parallel and perpendicular directions.

Figure 10:
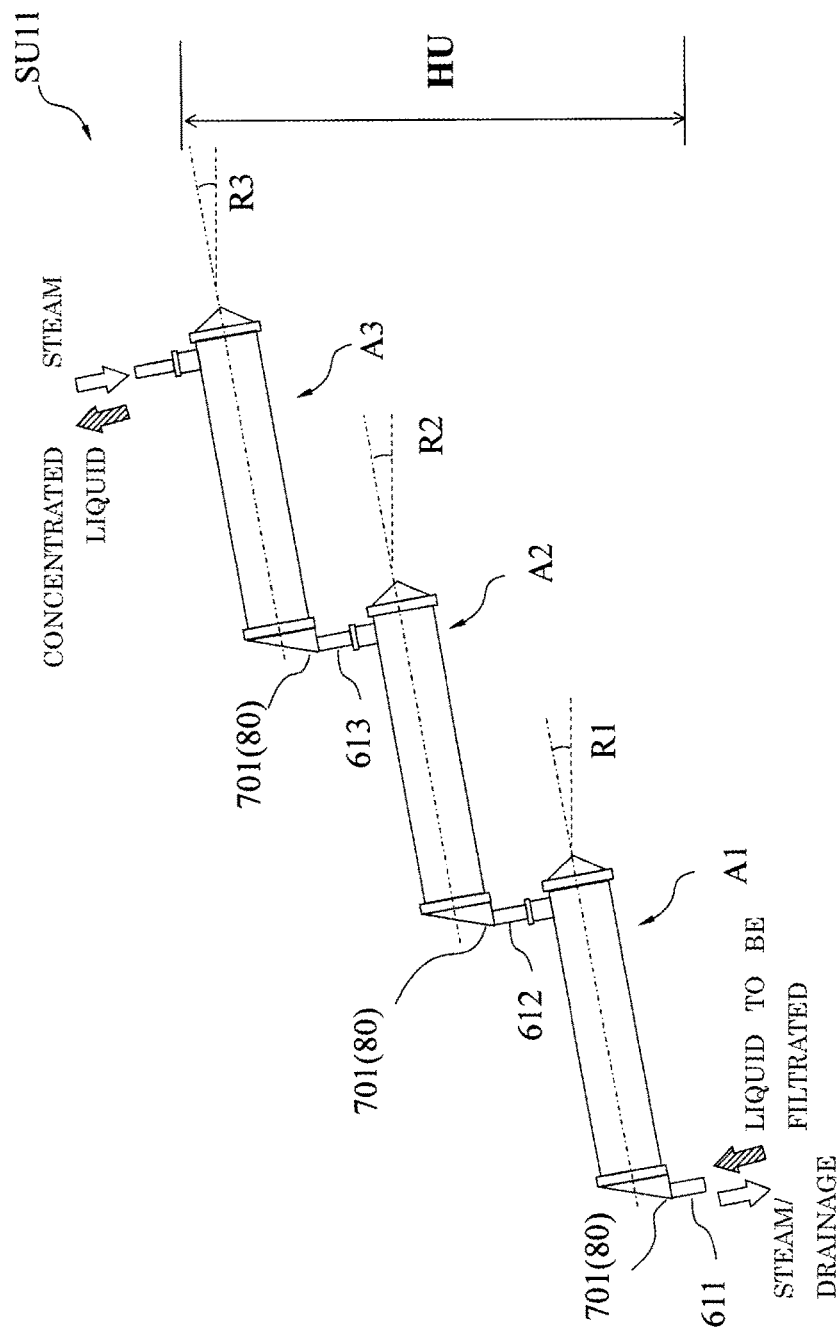
FIG. 10 is a schematic diagram of a separation membrane module unit in which separation membrane modules are obliquely disposed.

The term "angle" indicates an angle which becomes an acute angle among the angles between a straight line parallel to the longitudinal direction of the separation membrane module and a straight line parallel to the horizontal direction (angles R1, R2, and R3 in FIG. 10).

As the separation membrane modules are disposed in this manner, drainage at the time of steam sterilization can be promptly discharged as described above. When there are many modules to be connected in series, as much drainage corresponding thereto flows into the separation membrane modules in the lowermost stage. Therefore, in order to increase the down-flow velocity of drainage, it is preferable that an angle between the longitudinal direction of the separation membrane module and the horizontal direction is large.

Accordingly, even in the continuous-fermentation apparatus which includes equipment for performing steam sterilization, it is possible to reduce the size of the equipment for operation, and operation cost.

Moreover, among the separation membrane modules connected in series, it is acceptable when at least two modules have the angle within the range of the numerical values described above.

More specifically, in the separation membrane modules, it is preferable that the entrances for the liquid to be filtrated are disposed so as to be positioned higher than the exits for the non-permeated liquid. According to the configuration, drainage can be promptly discharged outside the separation membrane modules.

The positions of the separation membrane modules inside one series unit may be misaligned in the horizontal direction or may be overlapped with one another. When one series unit is viewed from above, the longitudinal direction of the plurality of separation membrane modules included in the series unit may be parallel to one another or may intersect with one another.

An amount of generated drainage varies depending on the outside temperature, the separation membrane module, the pipe on the periphery of the separation membrane modules, the heat-retention state of the equipment, and the like. Therefore, a suitable angle and the like can be checked by performing a steam heating test of the separation membrane modules in advance. In the steam heating test, for example, as heating steam is supplied to the inside of the separation membrane module through the exit for the non-permeated liquid of the separation membrane module (A3 in FIG. 1) at the upper portion, heating steam is supplied to the inside of the separation membrane module via the supply port of the liquid to be filtrated of the separation membrane module and the exit for the non-permeated liquid of the separation membrane module (A2 in FIG. 1) in the lower stage. Similarly, the heating is conducted to the separation membrane module (A1 in FIG. 1) in the lowermost stage. According to the experiment, if the temperature of the separation membrane module, particularly the temperature of the lower portion of each module can be raised to a predetermined sterilization temperature, the angle of each module is appropriate. Meanwhile, when there is a module which cannot be sufficiently heated up, it may be considered to increase the angle of the separation membrane module.

<Specific Example of Disposition of Separation Membrane Module in Series Unit>

Hereinafter, the specific example of disposition of the separation membrane modules in the series unit will be shown. The disposition of the modules can be applied to the above-described filtration device.

The series unit described below includes the separation membrane modules which are two or more separation membrane modules and which are separation membrane modules obliquely disposed; the liquid supply line by which primary sides of any one of the separation membrane modules and the other separation membrane module disposed lower than the separation membrane module are connected in series; and a drainage discharge line which supplies drainage of any one of the separation membrane modules to the other separation membrane module disposed lower than the separation membrane module.

Generally, the separation membrane module is usually long in one direction such as a cylinder or a rectangular parallelepiped. In a case where the plurality of such separation membrane modules are installed so as to cause the length direction to be parallel to the vertical direction (vertical mounting) and are connected in series, as the separation membrane modules are arranged in the vertical direction, the overall height of the equipment becomes equal to or greater than the product of (the length of each of the separation membrane modules)×(the number of overlapped modules).

In contrast, as the separation membrane modules are disposed so as to cause the longitudinal direction thereof to be oblique with respect to the vertical direction, the height of the equipment can be suppressed.

Figure 11:
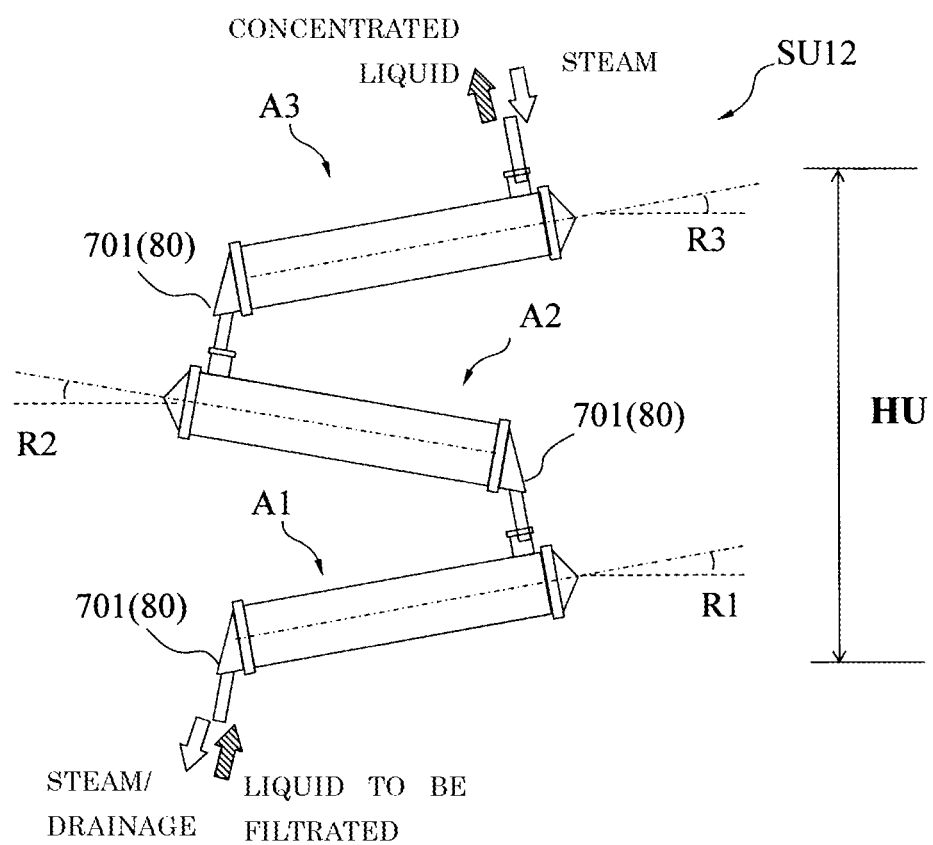
FIG. 11 is a schematic diagram of the separation membrane module unit in which the separation membrane modules are obliquely disposed.
Figure 12:
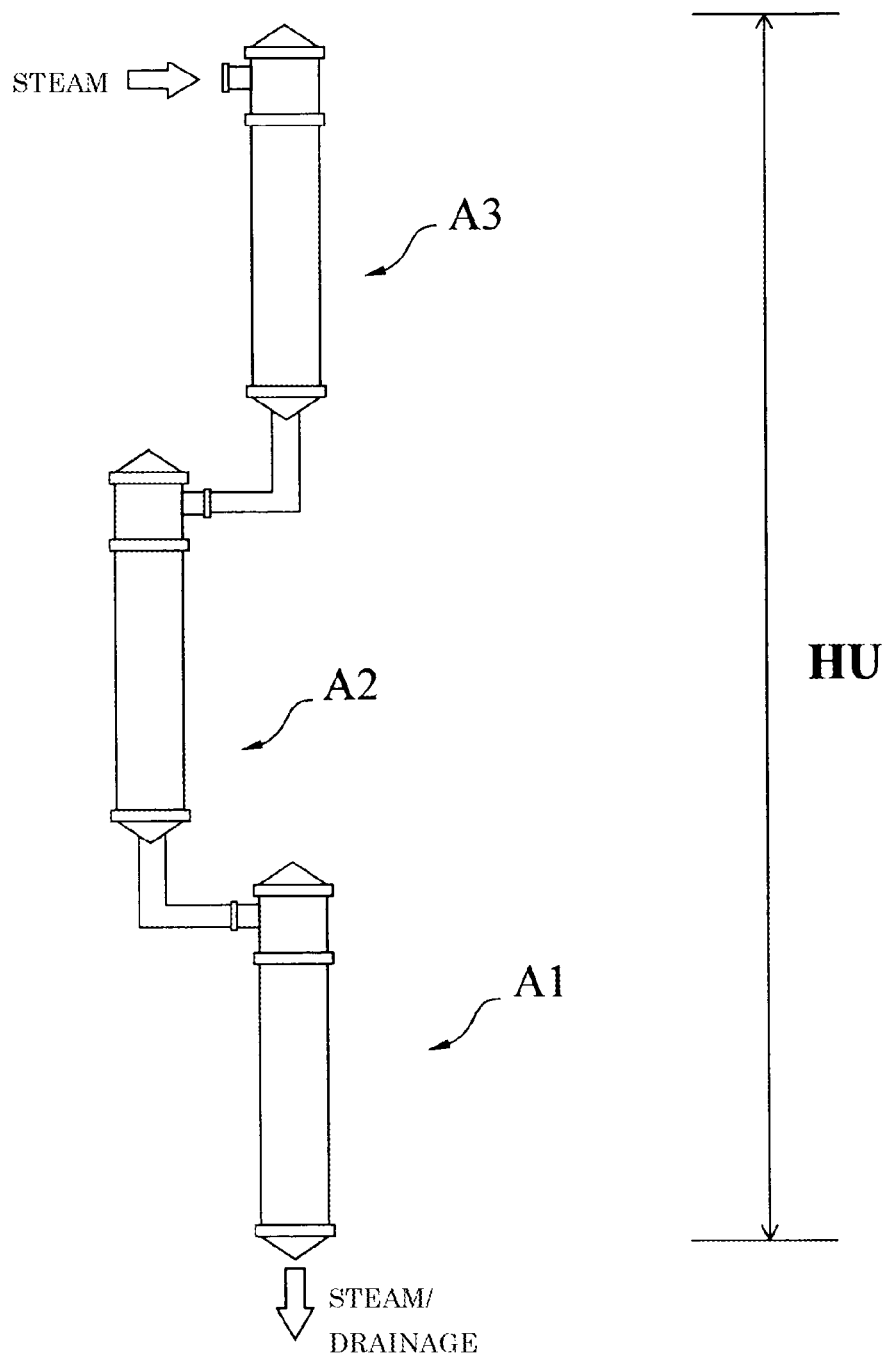
FIG. 12 is a schematic diagram of the separation membrane module unit in which the separation membrane modules are vertically disposed in series.
Figure 13:
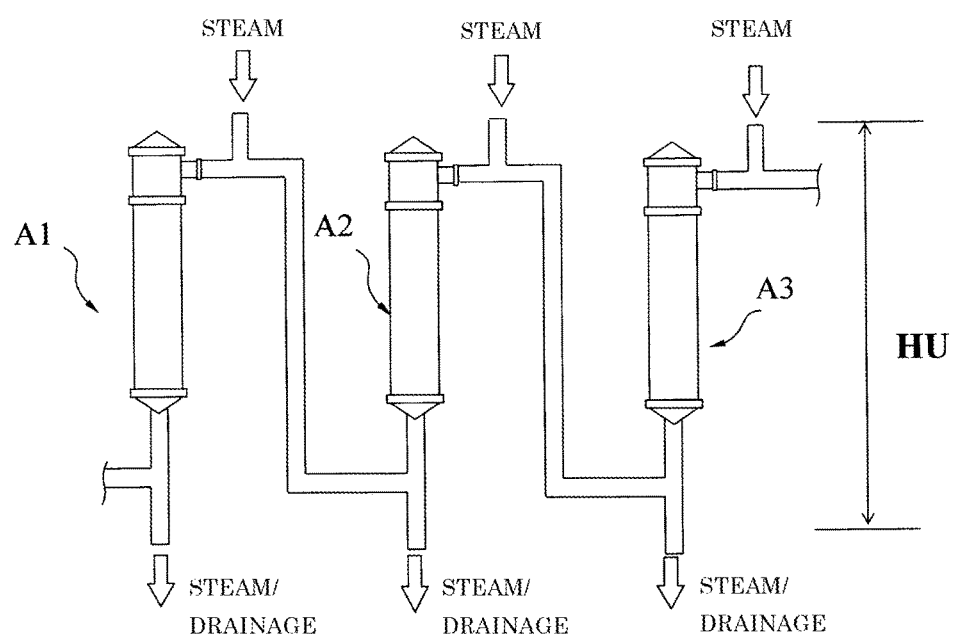
FIG. 13 is a schematic diagram of the separation membrane module unit in which the separation membrane modules are vertically disposed in parallel.

In FIGS. 10 and 11, the module unit including the external pressure-type hollow fiber membrane modules is exemplified. However, the present invention is not limited thereto and can be applied to various types of the separation membrane modules.

A series unit SU11 illustrated in FIG. 10 includes the plurality of separation membrane modules A1, A2, and A3, and series non-permeated liquid flow channels (examples of the liquid supply lines) 611, 612, and 613 which respectively connect between the separation membrane modules A1 and A2 and between the separation membrane modules A2 and A3 in series.

Figure 18:
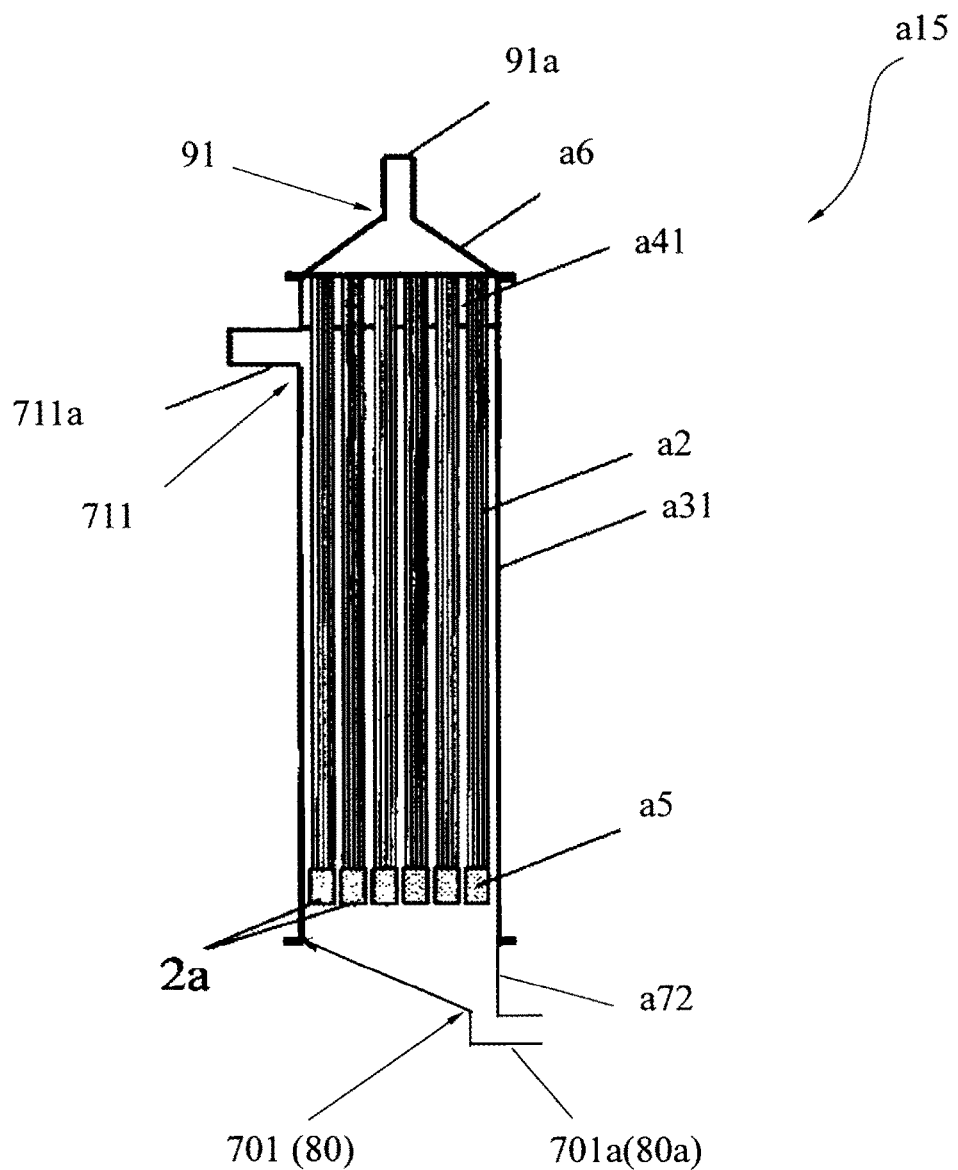
FIG. 18 is a schematic diagram of the separation membrane module according to still further embodiment.

Each of the separation membrane modules A1, A2, and A3 has a configuration similar to that of a hollow fiber membrane module a15 in FIG. 18. However, all the below-described separation membrane modules can be applied to the configurations in FIGS. 10 and 11.

The separation membrane module A1 is disposed at the lowermost position, the module A2 is disposed on the module A1, and the module A3 is disposed on the module A2. In this manner, when the separation membrane modules are stacked in the vertical direction, the pipe connecting the separation membrane modules can be shortened as compared to a case of being arranged in the horizontal direction, and thus, energy for operation can be reduced.

It is preferable that each angle between the longitudinal direction of the separation membrane modules A1, A2, and A3 (the height direction of the cylindrical case: indicated by the alternate long and short dash line in the drawing) and the horizontal direction (indicated by the dotted line in the drawing) ranges from 1° to 90°. Each angle between the longitudinal direction of the aforementioned modules and the horizontal direction may range from 1° to below 90°. Furthermore, the angle ranges more preferably from 1° to 45°, and ranges still preferably from 5° to 30°.

When the angle is equal to or greater than 1°, drainage can be prevented from staying inside separation membrane module when steam sterilization is performed, and sterilization failure can be effectively prevented. As the angle becomes large (as the longitudinal direction becomes close to the vertical direction), the velocity of drainage discharge (that is, the down-flow velocity of drainage) becomes large. Particularly, since drainage of the separation membrane modules in the upper stage gathers in the separation membrane modules in the lower stage, there is a concern about deterioration in heating-up properties in the separation membrane modules in the lower stage and the flow channel in the lower stage. When there are many modules to be connected in series, as much drainage corresponding thereto flows into the separation membrane modules in the lowermost stage. Therefore, it is preferable that the down-flow velocity of drainage is increased so as to quickly discharge drainage by increasing the angle between the longitudinal direction of the separation membrane modules and the horizontal direction.

Meanwhile, when the angle is small, a height HU of the separation membrane module unit can be minimized. Therefore, the equipment cost and operation cost can be reduced. Furthermore, time-consuming work in maintenance such as replacement of the separation membrane module can be reduced. Therefore, it is preferable that the inclination of the separation membrane module obliquely disposed is a necessity minimum, and an example thereof is the above-described range of from 1° to 45°.

In FIG. 10, the angles R2 and R3 between the longitudinal direction of all the modules A1, A2, and A3 inside the series unit SU11 and the horizontal direction are equivalent to each other. However, the angles of the plurality of separation membrane modules included in one series unit may be different from one another.

For example, a series unit SU12 in FIG. 11 has a configuration similar to that of the series unit SU11 in FIG. 10 except that each module is disposed so as to cause the longitudinal direction thereof to be in a zig-zag state together with the longitudinal direction of the adjacent module.

Among the modules connected in series, it is acceptable as long as at least two modules have the angle within the range of the numerical values described above. In other words, a separation membrane module having an angle which deviates from the range of the numerical values described above may be additionally connected to the separation membrane module having the angle within the range of the numerical values described above. Namely, the series unit is acceptable as long as the unit includes a first separation membrane module which is disposed so as to cause the angle between the longitudinal direction thereof and the horizontal direction to range from 1° to 45°, a second separation membrane module which is disposed so as to cause the angle between the longitudinal direction thereof and the horizontal direction to range from 1° to 45° while being disposed above the first separation membrane module, and the liquid supply line by which the primary sides of the first separation membrane module and the second separation membrane module are connected in series. Another separation membrane module having an angle different from the above-mentioned range may be connected between the first separation membrane module and the second separation membrane module.

The positions of the separation membrane modules inside one series unit may be misaligned in the horizontal direction or may be overlapped with one another. When one series unit is viewed from above, the longitudinal direction of the plurality of separation membrane modules included in the series unit may be parallel to one another or may intersect one another.

The angle of the separation membrane module may be determined by performing the steam heating test of the module in advance before being actually used. In the steam heating test, for example, as heating steam is supplied to the inside of the module through an exit 711 for the concentrated liquid of the module A3 at the upper portion, heating steam is supplied to the module A2 via an entrance 701 for the liquid to be filtrated of the module A3 and the exit 711 for the concentrated liquid of the module A2 below thereof. Similarly, the heating is conducted to the module A1 at the lower portion. According to the experiment, if the temperature of the separation membrane module, particularly the temperature of the lower portion of each module can be raised to a predetermined sterilization temperature, the angle of each module is appropriate. Meanwhile, when there is a module which cannot be sufficiently heated up, it may be considered to increase the angle of the separation membrane module.

In order to discharge drainage without staying, it is preferable that the drainage discharge ports of the modules are provided at the lowest positions in installation postures of the modules. When the modules are installed so as to cause the longitudinal direction of the modules to be along the vertical direction, the drainage discharge ports of the separation membrane modules may be provided at the lower end of the modules in the vicinity of the vertical axis of the modules (that is, in the vicinity of the center in the cross-sectional view). However, when the modules are obliquely installed, it is preferable that the drainage discharge ports are provided at an eccentric position. In other words, the drainage discharge port may be provided at a position where drainage is likely to be accumulated in the casing. In this manner, when the separation module is disposed so as to cause the longitudinal direction to be substantially parallel to the vertical direction or to be oblique, drainage is discharged without staying. A specific configuration thereof is illustrated in FIGS. 14, 16, 17 and 18.

For example, it is assumed that three cylindrical separation membrane modules having the diameter of 159 mm and the length of 1,500 mm are connected in series. In this case, as illustrated in FIGS. 10 and 11, when the modules are obliquely disposed, the height of the series unit in which the separation membrane modules are connected to one another can be suppressed to be approximately 1.5 m.

The series non-permeated liquid flow channels 611, 612, and 613 are acceptable as long as the flow channels can connect the primary sides of each module. In FIGS. 10 and 11, the series non-permeated liquid flow channel 612 connects a drainage discharge nozzle 80*a* of the upper module and a concentrated liquid discharge nozzle 711*a* of the lower module. In any case where any of the above-described modules is applied, the series non-permeated liquid flow channel may be connected to the similar position.

In the present embodiment, the number of the series units connected to one circulation pump in parallel is determined in consideration of specification and the like of the circulation pump. However, when considering the easiness of maintenance, it is desirable to be equal to or less than 10 units. When there is an occurrence of an abnormality such as a sudden rise of a differential pressure of membrane filtration, it is possible to detect the position of the separation membrane module in the series direction to be the origin of the occurrence of an abnormality (i.e., as to which stage in the line direction is the origin of the occurrence of an abnormality), based on the measurement result of the measuring gauge.

The number of the separation membrane modules included in one series unit is not limited to a specific numerical value. As the number of the separation membrane modules to be disposed in series increases, the total quantity of a pressure loss in the separation membrane module increases. Therefore, the circulation pump for cross-flow requires large power.

<Filtration Driving Power>

In FIG. 1, the fermentation liquid is supplied to all the separation membrane modules by the circulation pump 11. According to the configuration of the module in the specific example described above, while a pressure loss is taken into consideration, the driving power for filtration required in the filtration device of FIG. 1 can be covered by only the circulation pump 11.

However, when the driving power for filtration is covered by single pump only, as the number of the modules increases, the pump requires a large capacity. The separation membrane modules included in the entire filtration device may be divided into several groups, and the pump for supplying the fermentation liquid to the non-permeation sides of each group may be connected thereto. Moreover, in the order of the pump, the series unit, the pump and the series unit, two or more series units having the pump to be interposed therebetween may be connected in series. A part of the units may be disposed in series in the later stage of the other units.

In FIG. 1, the driving power for filtration is generated by the circulation pump 11. However, the driving power may be generated by other configuration. As the other configuration, for example, a siphon utilizing the liquid level difference (the water head difference) between the non-permeated liquid and the permeated liquid can be exemplified. The driving power for filtration may be obtained by adjusting pressure of the permeated liquid by the filtration pumps 121 to 123 which are installed in the permeated liquid pipe, in place of driving of the circulation pump 11, or together with the driving of the circulation pump 11. Additionally, the driving power for filtration can also be controlled by installing the control valve in at least one of the non-permeation sides and the permeation sides. The circulation pump 11 raises or reduces the driving power for filtration of all the separation membrane modules to which the fermentation liquid is supplied. The filtration pumps 121 to 123 and the control valve connected to the permeated liquid pipe adjust the driving power for filtration of the separation membrane modules which are connected to the same pipe. Moreover, the driving power for filtration is controlled by adjusting pressure of gas or a liquid introduced to the non-permeation side.

<Filtrating Operation Control Device>

The filtrating operation control device collectively controls pressures of the permeated liquids so as to reduce the transmembrane pressure difference and/or a difference in the filtration flow rate between the plurality of separation membrane modules to which the filtrating operation control device is connected and the separation membrane modules in a different stage.

The filtrating operation control device may be configured to include at least one of the permeated liquid flow rate sensor, the permeated liquid pressure sensor, and a differential pressure sensor (hereinafter, collectively referred to as "the sensor"), and may perform controlling based on an output result of the sensor. Since the sensor can obtain the filtration amount, filtration resistance, and information related thereto, the sensor can be referred to as an example of a detection unit for detecting filtrating operation circumstances.

The sensor is not necessarily installed so as to correspond to all the separation membrane modules, and may be installed in a representative separation membrane module. For example, the sensor may be provided in the permeated liquid pipe which is shared by the separation membrane modules disposed in the same stage.

The control unit may be configured to perform controlling based on data measured in advance, without measuring the values related to filtrating operation circumstances by using the sensor. Moreover, the control unit may drive each of the filtration pumps by the driving power set in advance for each of the filtration pumps.

<Membrane Cleaning Device>

In FIGS. 4 and 6, the membrane cleaning devices 40 and 401 are disposed so as to supply the cleaning liquid to the permeation sides of the separation membrane modules. However, the cleaning devices may be disposed so as to supply the cleaning liquid to the non-permeation sides of the separation membrane modules.

In FIGS. 4 and 6, the membrane cleaning devices 40 and 401 can switch ON/OFF of the supply of the cleaning liquid for each of the stages of the separation membrane modules. In other words, when the cleaning liquid is supplied to one stage, the membrane cleaning devices 40 and 401 supply the cleaning liquid to all the separation membrane modules included in the stage.

However, when the separation membrane modules in each of the stages are divided into two or more groups, and the pipes and the valves for supplying the cleaning liquid are provided for each group, ON/OFF of the supply of the cleaning liquid for each of the groups can be switched.

It is desirable that a pressure loss in the cleaning liquid supply line for each of the stages of the separation membrane modules is small. As the pressure loss in the cleaning liquid supply line is small, a gap between the transmembrane pressure differences of the separation membrane modules in the same stage is small, and thus, a uniform cleaning effect can be achieved. For example, when the gap between the transmembrane pressure differences is large, the cleaning liquid is unlikely to flow to the separation membrane module of which the transmembrane pressure difference is high, and there is a concern that the cleaning effect decreases. Even though the pressure loss depends on the type of the separation membrane module, in a case of the hollow fiber membrane module for precise filtration, a pressure loss in the cleaning liquid supply line in each of the stages is preferably equal to or less than 10 kPa, more preferably equal to or less than 5 kPa, and further preferably equal to or less than 1 kPa.

In order to reduce a pressure loss of the cleaning liquid supply line, there are considerations such as increasing of the diameter of the pipe, providing no extra measuring gauge and the like which become origins of a pressure loss, reducing the number of the separation membrane modules sharing one membrane cleaning device, and causing the cleaning liquid supply line to branch off in several lines and to be connected to the separation membrane modules while sharing the membrane cleaning device. From a view point of the pressure loss of the cleaning liquid supply line, it is preferable that the lengths of the cleaning liquid supply lines are substantially equal to one another for the modules sharing thereof in each of the stages.

Even though the pressure loss in the cleaning liquid supply line cannot be reduced, a head difference may be utilized by providing inclination such as installing the cleaning liquid supply line of the separation membrane module close to the membrane cleaning device at a high position and the cleaning liquid supply line of the separation membrane module far away from the membrane cleaning device at a lower position.

When the permeated liquid line and the cleaning liquid supply line are shared, the membrane cleaning device may be installed on a side opposite to the filtrating operation control device via the separation membrane modules sharing together.

<Separation Membrane Module>

The separation membrane may adopt any type of shape such as a flat membrane, a hollow fiber membrane, a spiral-type membrane. The hollow fiber membrane module may be any one of an external pressure type or an inner pressure type.

It is preferable that the fermentation liquid is equally supplied to the separation membrane modules. Therefore, it is preferable that liquid supply resistance is smaller with respect to the liquid supply pressure by the viscosity of the fermentation liquid to be supplied, the length and the diameter of the pipe of the liquid supply line.

One filtration device may include the plurality of separation membrane modules having the configurations different from one another (for example, the length of the separation membrane module, the filling ratio of the membrane, the type of the separation membrane, and the like), or all the separation membrane modules may have the same configuration. However, when the separation membrane modules having the filling ratio different from one another are included, if each of the modules has the velocity of cross-flow different from one another, a difference occurs in the cleaning effect of the separation membranes obtained by the shearing force of cross-flow depending on the module even though the flow rate of the fermentation liquid is controlled to be the same as one another. In addition, filtration velocity of the module also needs to be individually set. Moreover, since the management of the modules different from one another requires more time-consuming work as compared to the management of the modules of the same type, it is preferable that the specification of the separation membrane modules is the same as one another from a view point of production management.

Even though the separation membrane modules have the same specification, membrane filtration resistance (liquid-passing resistance of the membrane) may be different from one another depending on the lot. When the membrane filtration resistance is different from one another among the plurality of separation membrane modules sharing the permeated liquid pipe, filtration is actively performed in the separation membrane module having a smaller membrane filtration resistance, and clogging of the membrane is also promoted in such a separation membrane module.

Therefore, it is desirable to dispose the modules so as to reduce a difference between the sum of the membrane filtration resistance of the separation membrane modules sharing one permeated liquid pipe together and the sum of the membrane filtration resistance of the separation membrane modules sharing the other permeated liquid pipe. Accordingly, it is possible to unify the progress rate of clogging even in the separation membrane modules not sharing the permeated liquid pipe. As a result thereof, the frequency of maintenance and a workload for clogging is reduced.

When the membrane filtration resistance of the separation membrane modules on the upstream side is greater than the membrane filtration resistance of the separation membrane modules on the downstream side, it is possible to obtain the equivalent filtration velocity between the modules on the upstream side and the downstream side by increasing the transmembrane pressure difference in the separation membrane modules on the upstream side. In this case, in order to increase the transmembrane pressure difference, the valve or power of the pump in the filtrating operation control device is lowered, and pressure of the permeated liquid of the separation membrane modules on the upstream side is reduced. Thus, it is possible to increase the transmembrane pressure difference. In this manner, as the separation membrane modules having large membrane filtration resistance is disposed on the upstream side, it is possible to reduce the difference between the fluxes of the separation membrane modules with low power, and thus, an energy saving effect can be achieved.

With regard to the gap between the magnitudes of the membrane filtration resistance for each of the lots of the separation membrane modules, values listed in the inspection table of the separation membrane module may be referred, or measurement may be performed by filtrating water while applying certain predetermined pressure thereto and measuring the filtration amount per unit time.

(1) Configuration of Separation Membrane Module

Descriptions will be given regarding a specific configuration of the separation membrane module with reference to the drawings while exemplifying the external pressure-type hollow fiber membrane module.

Figure 14:
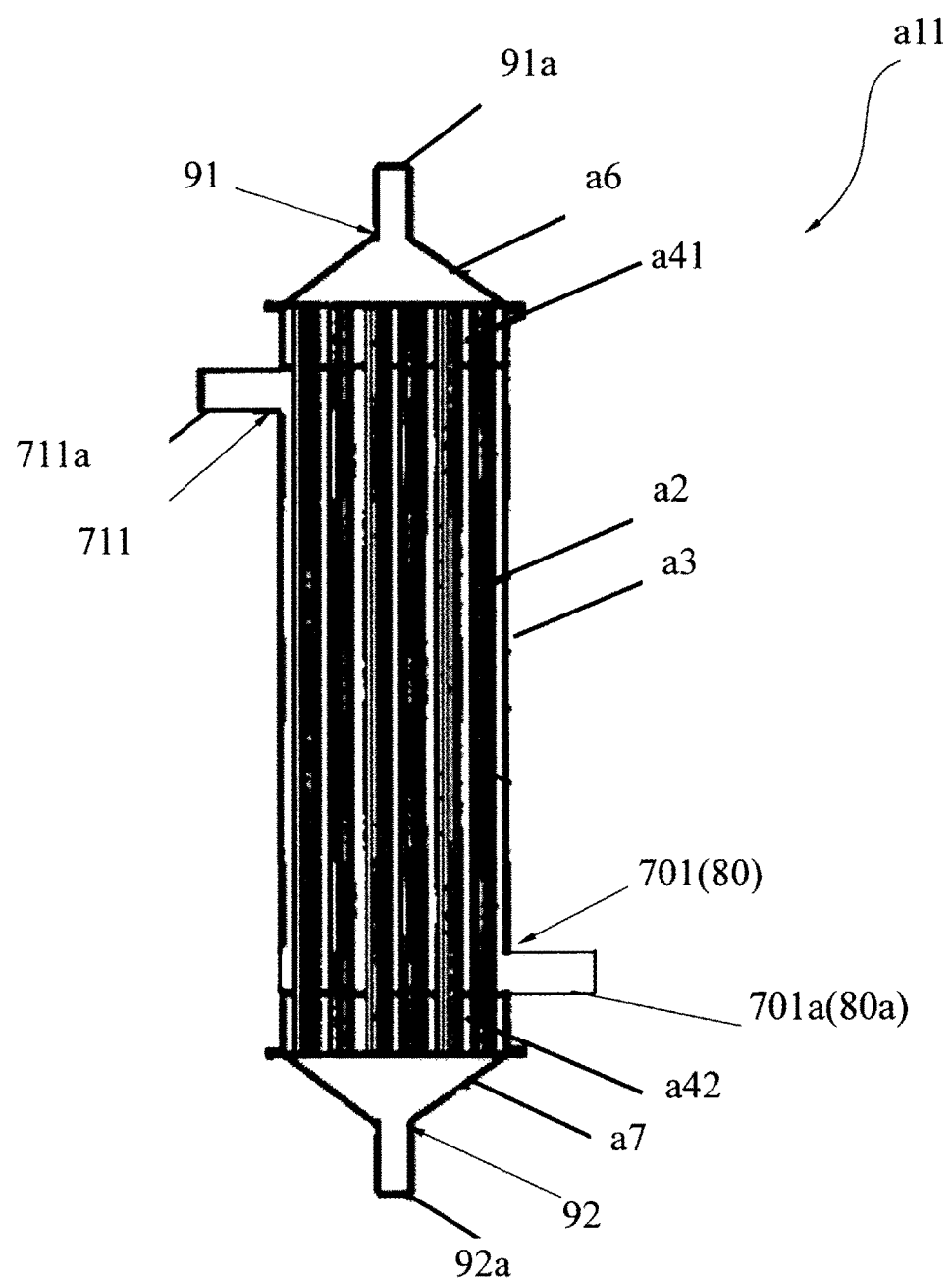
FIG. 14 is a schematic diagram of the separation membrane module according to one embodiment of the present invention.

A hollow fiber membrane module a11 in FIG. 14 includes a cylindrical case a3 of which both ends are opened, an upper cap a6, a lower cap a7, and a large number of hollow fiber membranes a2 which are stored inside the cylindrical case a3.

The cylindrical case a3, the upper cap a6, and the lower cap a7 correspond to the casing.

The cylindrical case a3 is a cylindrical case of which both ends are opened. On the side surface thereof, the entrance 701 for the liquid to be filtrated is provided in the vicinity of the lower end of the cylindrical shape in the height direction, and the exit 711 for the concentrated liquid is provided in the vicinity of the upper end in the height direction. In addition, nozzles 701a (80a) and 711a protrude respectively from the entrance 701 for the liquid to be filtrated and the exit 711 for the concentrated liquid.

The upper cap a6 is mounted at the upper end of the cylindrical case a3. A first exit 91 for the filtrated liquid is provided on the upper cap a6. The lower cap a7 is mounted at the lower end of a cylindrical case a4. A second exit 92 for the filtrated liquid is provided on the lower cap a7. The nozzles 91a and 92a protrude respectively from the exits 91 and 92 for the filtrated liquid. In the present embodiment, the entrance 701 for the liquid to be filtrated also serves as a drainage discharge port 80. The entrance 701 for the liquid to be filtrated also functions as an air supply port.

In the present embodiment, both ends of the hollow fiber membrane a2 are opened. However, the present invention is not limited thereto. The hollow fiber membrane is acceptable as long as at least one of two end surfaces is opened. In the present embodiment, the upper end and the lower end of the hollow fiber membrane a2 are respectively bundled with the hollow fiber membrane bundling members a41 and a42. In FIG. 14, as both the hollow fiber membrane bundling members a41 and a42 are fixed to the inside of the cylindrical case a3, the hollow fiber membrane bundles are fixed to the inside of the cylindrical case a3. The hollow fiber membrane bundling members a41 and a42 are formed with a so-called potting material. The hollow fiber membrane bundles may be fixed to the inside of the cylindrical case a3 as a cartridge-type membrane having the hollow fiber membrane a2 and the hollow fiber membrane bundling members a41 and a42 by causing the hollow fiber membrane bundling members a41 and a42 to be bonded and fixed to the inside of a container having a cylindrical shape or the like as necessary and to be fixed to the inside of the cylindrical case a3 in a liquid-tight sealing by using a sealing material such as an O-ring and a packing.

In the hollow fiber membrane module a11, for example, in a case of total amount filtration, the liquid to be filtrated is supplied through the entrance 80 for the liquid to be filtrated to the inside of the cylindrical case a3, specifically to the outside of the hollow fiber membrane a2 (the non-permeation side: the primary side). The permeated liquid which has permeated the hollow fiber membrane a2 passes through the inside of the hollow fiber membrane (the permeation side: the secondary side), flows into the upper cap a6 through the open upper end of the hollow fiber membrane a2, and then, flows out of the hollow fiber membrane module a11 through the first exit 91 for the filtrated liquid. The permeated liquid can also flow into the lower cap a7 through the open lower end of the hollow fiber membrane a2. The permeated liquid which has flowed into the lower cap a7 as described above flows out of the hollow fiber membrane module a11 through the second exit 92 for the filtrated liquid. Since the hollow fiber membrane bundling members a41 and a42 are fixed to the inner wall (that is, the inner wall of the casing) of the cylindrical case a3 in a liquid-tight sealing, the permeated liquid, the liquid to be filtrated, and the concentrated liquid are isolated so as to be not mixed with one another.

Figure 15:
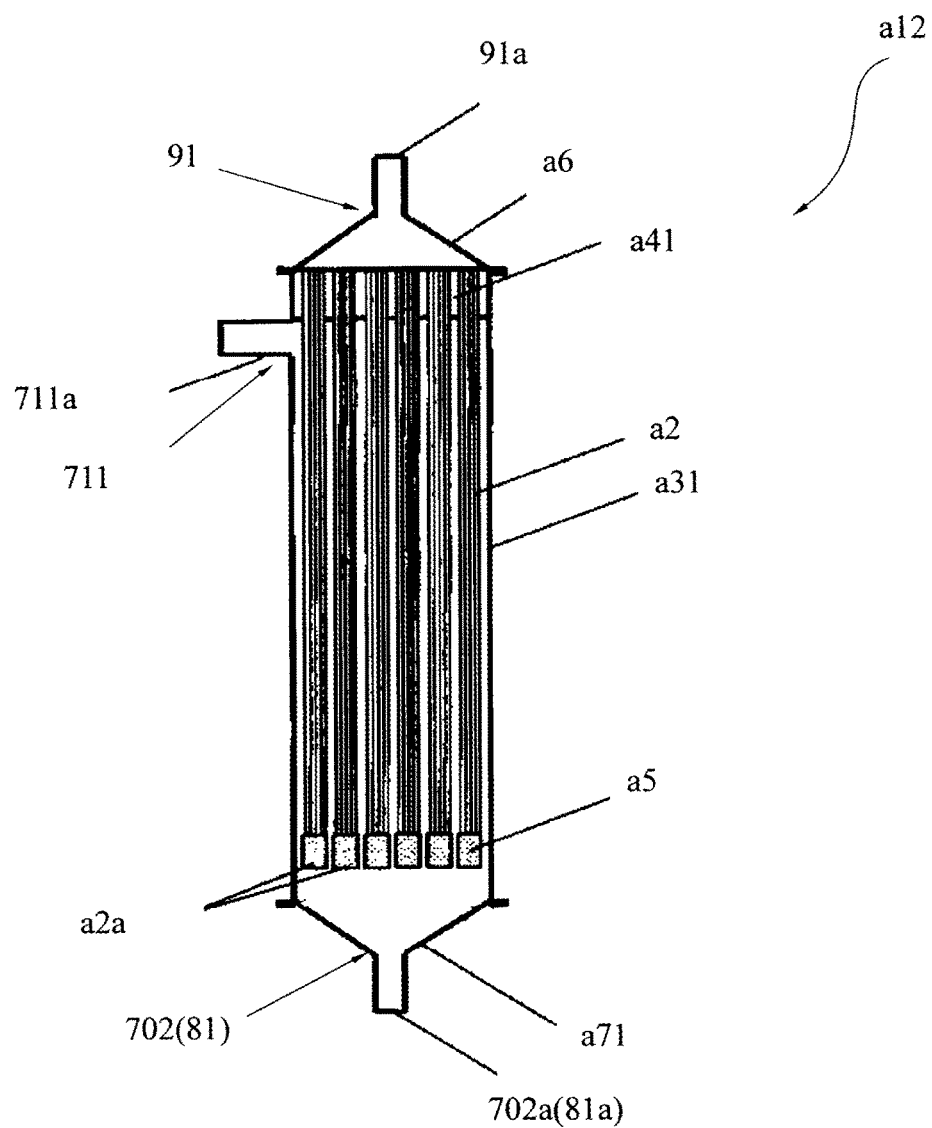
FIG. 15 is a schematic diagram of the separation membrane module according to another embodiment.

A hollow fiber membrane module a12 in FIG. 15 is bundled with a small bundle blocking member a5 in a state where the lower end of the hollow fiber membrane a2 is blocked, and has substantially the same configuration as that in FIG. 14 except that a cylindrical case a31 and a lower cap a71 are provided in place of the cylindrical case a3 and the lower cap a7. The same reference numerals and signs will be applied to the members that have already been described, and descriptions therefor will be omitted.

In the embodiment in FIG. 15, the upper end of the hollow fiber membrane a2 is bundled with the hollow fiber membrane bundling member a41 while being in an open state. The hollow fiber membrane bundling member a41 is fixed in the vicinity of the upper end of the cylindrical case a3 in a liquid-tight sealing, similar to the embodiment in FIG. 14. Meanwhile, the lower end portion of the hollow fiber membrane a2 is divided into small bundles a2a of approximately from 1 bundle to 300 bundles. Each of the small bundle a2a is bundled with the small bundle blocking member a5 and the lower end thereof is blocked.

In the lower end portion, the small bundle a2a is not fixed to the casing, thereby being able to freely move. Each of the small bundles a2a may include string-like or rod-like members having high strength and low elasticity for reinforcement, such as steel wires and aramid fiber cords.

The cylindrical case a31 has a configuration similar to that of the cylindrical case a3 except that the entrance for the liquid to be filtrated is not included. The lower cap a71 has a structure similar to that of the lower cap a7 in FIG. 14. However, the structure corresponding to the exit 92 for the filtrated liquid in the lower cap a7 functions as an entrance 702 for the liquid to be filtrated, a drainage discharge port 81, and the air supply port.

In the hollow fiber membrane module a12 of FIG. 15, for example, in a case of cross-flow filtration, the liquid to be filtrated passes through among the plurality of small bundles a2a through the entrance 702 for the liquid to be filtrated, and is supplied to the inside of the cylindrical case a3, specifically to the outside of the hollow fiber membrane a2. The permeated liquid which has permeated the hollow fiber membrane a2 passes through the inside of the hollow fiber membrane, flows into the upper cap a6 through the open upper end of the hollow fiber membrane a2, and then, flows out of the hollow fiber membrane module a12 through the first exit 91 for the filtrated liquid. The concentrated liquid which has not permeated the hollow fiber membrane a2 flows out of the hollow fiber membrane module a12 through the exit 711 for the concentrated liquid. Since the hollow fiber membrane bundling member a41 is fixed to the inner wall (that is, the inner wall of the casing) of the cylindrical case a3 in a liquid-tight sealing, the permeated liquid, the liquid to be filtrated, and the concentrated liquid are isolated so as to be not mixed with one another.

It is possible to combine the configuration of FIG. 14 and the configuration of FIG. 15. In other words, in the configuration of FIG. 14, end portions of the hollow fiber membranes a2 on one side may be blocked. For example, the hollow fiber membranes a2 of FIG. 14 bundled with the hollow fiber membrane bundling members a41 and a42 may be accommodated inside the casing of FIG. 15 including the cylindrical case a31, the upper cap a6, and the lower cap a71. The hollow fiber membrane bundling member a42 may block the lower end of the hollow fiber membrane a2. In this case, the cylindrical case a3 may not be fixed to the hollow fiber membrane bundling member a42, and a gap may be provided between the cylindrical case a3 and the hollow fiber membrane bundling member a42.

In all the configurations described above, the curved portion of the bundle which are bent in a U-shape may be bundled with a blocking member or a bundling member at the end portion to be blocked among the upper end and the lower end of the membrane.

Figure 16:
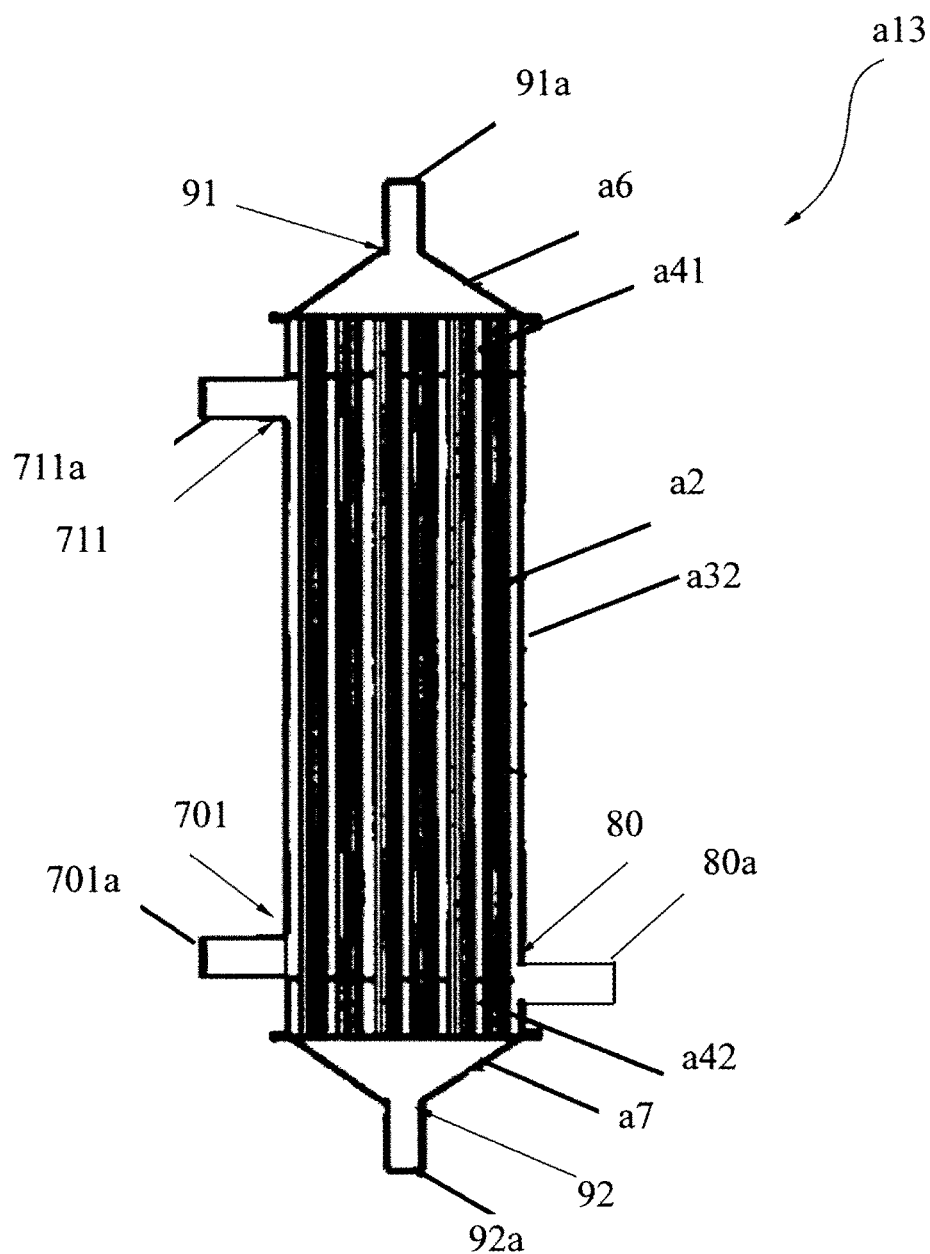
FIG. 16 is a schematic diagram of the separation membrane module according to still another embodiment.
Figure 17:
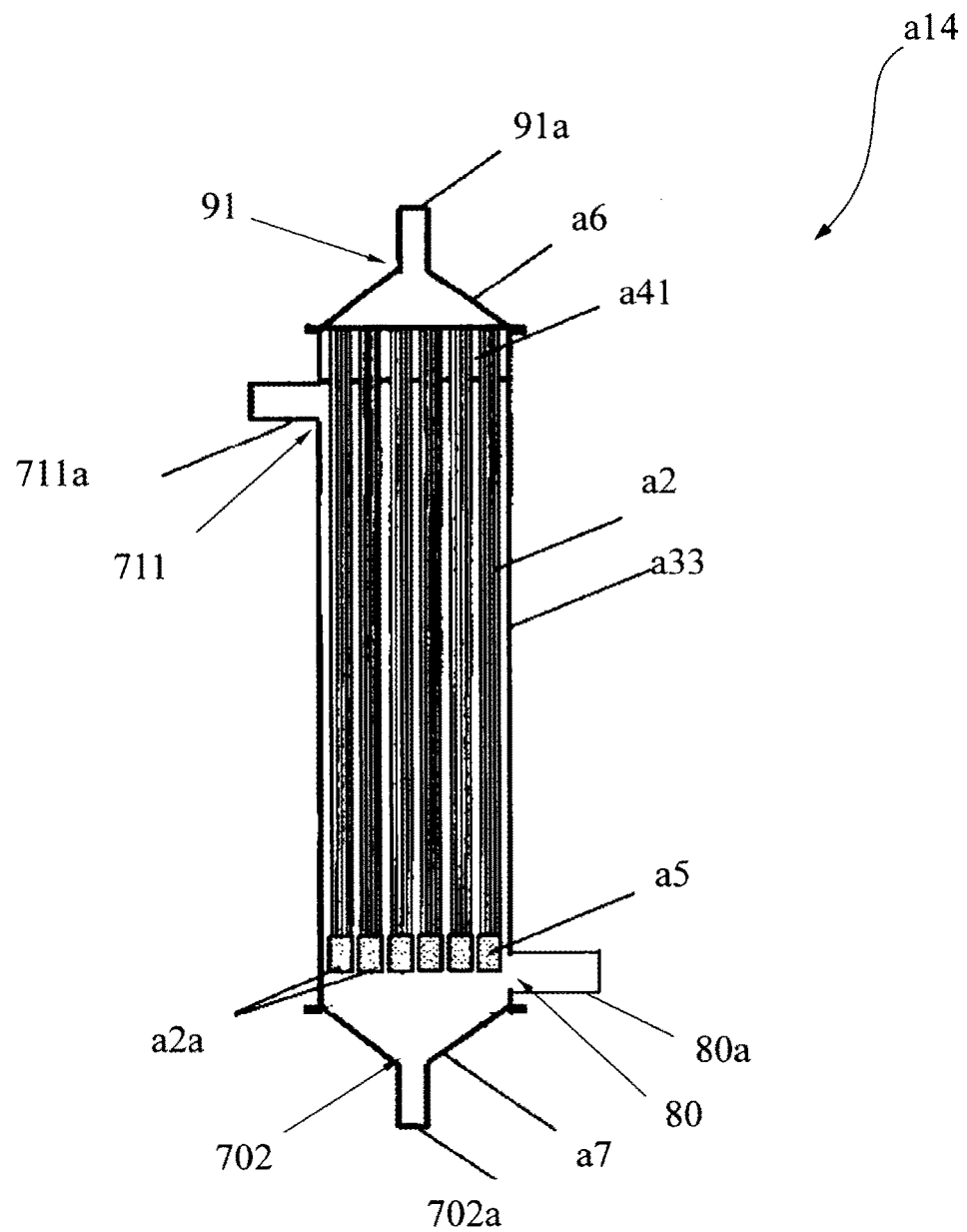
FIG. 17 is a schematic diagram of the separation membrane module according to further embodiment.

Furthermore, as illustrated in FIGS. 16 and 17, the drainage discharge port 80 may be provided separately from the entrance 701 for the liquid to be filtrated.

Specifically, a separation membrane module a13 of FIG. 16 has the same configuration as the hollow fiber membrane module a11 of FIG. 14 except that a cylindrical case a32 is included in place of the cylindrical case a3. The cylindrical case a32 includes the entrance 701 for the liquid to be filtrated and the drainage discharge port 80 which are separately provided in the vicinity of the lower end. The position of the entrance 701 for the liquid to be filtrated may be close to or far away from the drainage discharge port 80 in the circumferential direction of the cylindrical case.

A separation membrane module a14 of FIG. 17 has the same configuration as the hollow fiber membrane module a12 of FIG. 15 except that a cylindrical case a33 is included in place of the cylindrical case a31. The cylindrical case a33 includes the drainage discharge port 80 at the lower end thereof. In the configuration of FIG. 17, the positions of the entrance 702 for the liquid to be filtrated and the drainage discharge port 80 may be switched each other.

The hollow fiber membrane module a15 of FIG. 18 has a configuration similar to that of the hollow fiber membrane module a12 of FIG. 15 except that the entrance 701 for the liquid to be filtrated (the drainage discharge port 80) is provided at an eccentric position. In FIGS. 14, 16, and 17, the drainage discharge port 80 is provided at an eccentric position.

Descriptions will be given regarding more specific configurations of the above-described members and members that the separation membrane module can additionally include.

(2) Casing

It is preferable that the cylindrical case a3, the upper cap a6, and the lower cap a7 have heat resistance with respect to steam sterilization. For example, as a material of the members, a heat resistant resin such as polysulfone, polycarbonate, and polyphenylene sulfide is adopted in an independent or mixed manner. As a material other than the resin, aluminum, stainless steel, and the like are preferable. Additionally, as a preferable material, a composite of a resin and metal and a composite material such as a glass fiber reinforced resin, carbon fiber reinforced resin, and the like can be exemplified.

The shape of the casing is not particularly limited. However, it is preferable that the casing has a cylindrical body. The shape of the body portion is not necessarily a cylinder, and the shape can be changed in consideration of easiness in the manufacture of the casing, minimization of a dead space inside the separation membrane module, and the like.

(3) Rectification Member

The separation membrane module may include the rectification member inside the casing in order to rectify a stream inside the separation membrane module. For example, the rectification member is a cylindrical member and is disposed in the vicinity of the upper end of the casing (for example, in the vicinity of the upper end of the cylindrical case a3 and the cylindrical case a31).

The separation membrane may be fixed to the casing or a rectification member by using an adhesive or the like. The separation membrane may be a cartridge-type membrane. In other words, the separation membrane may be attachable and detachable with respect to the casing or the rectification member.

(4) Bundling Member

A member such as the hollow fiber membrane bundling members a41 and a42 which bundles the hollow fiber membranes in an open state, and a member such as the small bundle blocking member a5 which blocks and bundles the hollow fiber membranes are collectively referred to as the bundling member. As the bundling member, an adhesive is preferably adopted.

As an adhesive, a synthetic resin having type D durometer hardness in a range approximately from 50 to 80 after being cured is preferably adopted. The type D durometer hardness is measured in accordance with JIS-K6253 (2004).

As the hardness is caused to be equal to or greater than 50, even when a differential pressure is applied to the primary sides and the secondary sides of the separation membranes, such as a case where saturated high pressure water vapor is input through the primary sides of the separation membranes during filtration, backwashing, and steam sterilization, it is possible to minimize the deformation of the hollow fiber membrane bundling members a4. As a result thereof, it is possible to prevent detachment occurring between the hollow fiber membranes and the bundling member, thereby reducing the concern of rupture of the hollow fiber membranes a2 causing a leak.

The hardness being equal to or less than 80 also reduces the risk of damage to the hollow fiber membranes. At a portion on the surface of the bundling member where the hollow fiber membranes protrude, the corner of the bundling member and the hollow fiber membranes are in contact with each other. When vibration of the hollow fiber membranes occurs during filtration, backwashing, and the like, there is a concern that the corner of the bundling member and the outer surfaces of the hollow fiber membranes strongly come into contact with each other. However, in such a case as well, since the hardness is equal to or less than 80, an occurrence of damage and rupture of the hollow fiber membranes can be prevented.

As the above-mentioned adhesive for the hollow fiber membrane bundling member a4 and the small bundle blocking member a5, it is preferable to adopt a synthetic resin which is an inexpensive general-purpose product and has less influence on the quality of water, such as an epoxy resin and a polyurethane resin.

(5) Filling Ratio of Separation Membrane

Descriptions will be given regarding a filling ratio of the separation membranes in the separation membrane module with reference to an example of the hollow fiber membrane module. Here, the filling ratio of the hollow fiber membranes in the hollow fiber membrane module can be obtained through the following Expression 1.

$$\phi = \frac{\pi\left(\frac{OD}{2}\right)^2 \times n \times N}{\pi\left(\frac{ID}{2}\right)^2} \times 100$$

Φ: filling ratio of hollow fiber membrane module (%)
OD: outer diameter of hollow fiber membrane (mm)
n: the number of hollow fiber membranes in hollow fiber membrane bundle (number/bundle)
N: the number of hollow fiber membrane bundles per one module (bundle/module)
ID: inner diameter of casing of module (mm)

The filling ratio of the hollow fiber membranes in the hollow fiber membrane module can be suitably determined in accordance with the purpose of use and circumstances. Specifically, it is preferable that the filling ratio ranges from 30% to 60%. In the present embodiment, since the hollow fiber membrane modules are obliquely disposed and are connected in series and steam sterilization is performed, the filling ratio of the hollow fiber membranes is preferably equal to or greater than 40%, and more preferably equal to or greater than 45%.

The reason therefor is as follows. When the hollow fiber membrane modules are obliquely installed, the hollow fiber membranes are biased inside the casing in the vertical direction, and the bias possibly affects heating-up properties and the stream of cross-flow during sterilization. Therefore, it is preferable that the casing is filled with the hollow fiber membranes so as to prevent the bias of the hollow fiber membranes from being large in the casing, thereby suppressing the gap to be minimum necessary. Accordingly, it is preferable to set the filling ratio of the hollow fiber membranes to be higher than that in a general case.

In order to prevent the hollow fiber membranes from biasing in the casing, the hollow fiber membranes may be retained by using a retention plate and the like. It is preferable that a retention member such as the retention plate has heat resistance with respect to steam sterilization, and it is preferable to have a structure having no concave portion so as to allow no steam drainage to stay.

Another reason for requiring the filling ratio to be preferably equal to or greater than 30% will be described below. As the filling ratio becomes greater, the membrane area per module increases, and thus, filtration efficiency is improved. As the filling ratio is equal to or greater than 30%, the cross section area inside the hollow fiber membrane module excluding the hollow fiber membranes can be minimized. Therefore, the linear velocity on the membrane surface can be enhanced without increasing the circulation flow rate. In other words, since a linear velocity suitable for filtration can be obtained without requiring a large-sized circulation pump, instrument cost and operation electricity can be suppressed. Moreover, since the circulation flow rate can be small, pipes having a small diameter can be used. As a result thereof, it is possible to suppress cost for pipes and valves such as automatic valves.

As the filling ratio of the hollow fiber membranes is equal to or less than 60%, steam, the liquid to be filtrated, and the cleaning liquid are likely to pervade inside the modules during sterilization, filtrating operation, and cleaning, respectively.

In addition, as the filling ratio of the hollow fiber membranes is equal to or less than 60%, microorganisms can be easily discharged out of the modules so that it is easy to prevent clogging of the membranes. Moreover, when the filling ratio is equal to or less than 60%, the hollow fiber membrane bundle can be easily inserted into the casing. Furthermore, an adhesive configuring the bundling member can easily infiltrate among the hollow fiber membranes, thereby allowing the manufacture to be easy.

<Separation Membrane>

The separation membrane may be any one of an organic membrane and an inorganic membrane. Since the separation membrane is cleaned by performing backwashing, chemical liquid submerging, or the like, it is preferable that the separation membrane has pressure resistance and chemical resistance.

From a view point of separation performance, water permeability, and fouling resistance, it is preferable that the separation membrane contains an organic polymer compound as a main component. As the organic polymer compound, for example, a resin such as a polyethylene resin, a polypropylene resin, a polyvinyl chloride resin, a polyvinylidene fluoride resin, a polysulfone resin, a polyether sulfone resin, a polyacrylonitrile resin, a cellulose resin, and a cellulose triacetate resin can be exemplified. The separation membrane contains the above-mentioned resin as the main component, and may include a mixture of multiple resins.

It is preferable to adopt a polyvinyl chloride resin, a polyvinylidene fluoride resin, a polysulfone resin, a polyether sulfone resin, and a polyacrylonitrile resin which allow the manufacture of membranes performed by a solution to be easy and are excellent in physical durability and chemical resistance. A polyvinylidene fluoride resin or a resin having a polyvinylidene fluoride resin as a main component is preferably adopted for the reason of having a feature including chemical strength (particularly, chemical resistance) and physical strength together.

More preferably, the separation membrane is a hollow fiber membrane including a fluorine resin-based polymer and has both a three-dimensional network structure and a spherical structure. The separation membrane is a hollow fiber membrane having hydrophilicity by containing a hydrophilic polymer which includes at least one component selected from fatty acid vinyl ester, vinylpyrrolidone, ethylene oxide, and propylene oxide; or cellulose ester in the three-dimensional network structure.

Here, the three-dimensional network structure denotes a structure in which solid contents spread out three-dimensionally in a network manner. The three-dimensional network structure has pores and voids partitioned by the solid contents forming the net.

The spherical structure denotes a structure in which a large number of solid contents having spherical shapes or substantially spherical shapes are connected directly to one another or connected via stripe-shaped solid contents.

The separation membrane may include a layer other than the spherical structure layer and the three-dimensional network structure layer, for example, a support layer such as a porous substrate. The porous substrate is not particularly limited and may be formed with an organic material, an inorganic material, and the like. It is preferable to adopt an organic fiber in a view of being easily lightened in weight. More preferably, the porous substrate is a woven fabric or a non-woven fabric made with an organic fiber such as a cellulosic fiber, a cellulose acetate fiber, a polyester fiber, a polypropylene fiber, and a polyethylene fiber.

The three-dimensional network structure layer and the spherical structure layer can be changed with regard to disposition of being top, bottom, in, and out depending on the filtration method. However, since the three-dimensional network structure layer exhibits the separation function and the spherical structure layer exhibits physical strength, it is preferable that the three-dimensional network structure layer is disposed on a separation target side. Particularly, in order to prevent filtration performance from deteriorating due to adhered contaminants, it is preferable that the three-dimensional network structure layer exhibiting the separation function is disposed on the outermost layer on the separation target side.

The average pore diameter of the membrane can be suitably determined in accordance with the purpose of use and circumstances. However, it is preferable that the average pore diameter is small to a certain extent. Generally, it is favorable that the average pore diameter ranges from 0.01 µm to 1 µm. When the average pore diameter of the hollow fiber membrane is less than 0.01 µm, membrane contamination components, for example, components such as sugar and protein, aggregates thereof, and the like block the pores, and thus, operations cannot be stably performed. When considering balance with respect to the water permeability, the average pore diameter is preferably equal to or greater than 0.02 µm, and is more preferably equal to or greater than 0.03 µm. When exceeding 1 µm, detachment of contaminant components from the pores performed by the shearing force generated by smoothness of the membrane surface and a stream on the membrane surface, and physical cleaning such as backwashing and air scrubbing becomes insufficient, and thus, operations cannot be stably performed. Furthermore, when the average pore diameter of the hollow fiber membrane approximates the size of cells, the cells may block the pore directly. In addition, debris of cells generated by extinction of a portion of cells in the fermentation liquid may be produced. Therefore, in order to avoid the hollow fiber membranes from being blocked by the debris, it is preferable that the average pore diameter is equal to or less than 0.4 µm, and when the average pore diameter is equal to or less than 0.2 µm, it is possible to more favorably perform operations.

Here, the average pore diameter can be obtained by measuring and averaging the diameters of a plurality of pores which are observed through observation using a scanning-type electron microscope at a magnification of 10,000 times or higher. It is preferable that ten or more, preferably twenty or more pores are randomly selected, and the diameters thereof are measured, thereby obtaining the average pore diameter through number average. When the pores are not circular, it is possible to preferably employ a method in which a circle having an area equivalent to the area of the pore, that is, an equivalent circle is obtained by using an image processing apparatus and the like, and the diameter of the equivalent circle is considered as the diameter of the pore.

EXAMPLES

Hereinafter, effects of the embodiments of the present invention will be described in more detail with reference to Examples. However, the present invention is not limited to the following Examples.

(1) Manufacture of External Pressure-Type Hollow Fiber Membrane (a) A vinylidene fluoride homopolymer having a weight average molecular weight of 417,000 and γ-butyrolactone were dissolved at the temperature of 170° C. in the respective ratios of 38% by mass and 62% by mass. This polymer solution was discharged through a cap while causing γ-butyrolactone to be associated as a hollow portion forming liquid, the output was solidified in the cooling bath containing an aqueous solution having 80% by mass of γ-butyrolactone at a temperature of 20° C., and then, a hollow fiber membrane having a spherical structure was manufactured.

(b) Subsequently, in a ratio of a vinylidene fluoride homopolymer having the weight average molecular weight of 284,000 of 14% by mass, cellulose acetate propionate (manufactured by Eastman Chemical Company, CAP482-0.5) of 1% by mass, N-methyl-2-pyrrolidone of 77% by mass, T-20C of 5% by mass, and water of 3% by mass, the components were mixed and dissolved at the temperature of 95° C., and a polymer solution was prepared. This membrane-forming raw liquid was uniformly applied to the surface of the spherical-structured hollow fiber membrane which was obtained at the above-described process (a). Then, the membrane was immediately coagulated in the water bath, and the hollow fiber membrane having a three-dimensional network structure on the spherical structure layer was manufactured. The thus-obtained hollow fiber membrane was brought into contact with 125° C.-saturated water vapor for 1 hour.

(c) The average pore diameter on the surface of the water to be treated side of the hollow fiber membrane which was obtained through the above-described process (b) was 0.04 μm. The pure water permeation amount of the hollow fiber membrane which was obtained through the above-described process (b) was evaluated, and the result was $5.5 \times 10^{-9}$ m$^3$/m$^2$/s/Pa. The measurement of the water permeation amount was performed at the head height of 1 m by using purified water at the temperature of 25° C. obtained through the reverse osmosis membrane.

(2) Manufacture of External Pressure-Type Hollow Fiber Membrane Module

The separation membrane module was manufactured by using the hollow fiber membrane which was manufactured through the above-described process (1). Specifically, the hollow fiber membrane was bundled with the potting material (polyurethane manufactured by SANYU REC CO., LTD., SA-7068A/SA-7068B, of the mixing ratio thereof is 64:100 in terms of the weight ratio). A portion of the potting material was cut off at the upper end of the hollow fiber membrane so that the hollow fiber membrane was opened. The hollow fiber membrane bundled as described above was fixed to the inside of the casing which is a polysulfone resin-made cylindrical container, whereby the module was formed. The casing having the size of 10 mm in inner diameter and 15 cm in length was used.

Example 1

Example 1 was conducted by using the produced porous hollow fiber membrane and membrane filtration module. The operational condition of Example 1 was as follows unless otherwise noted particularly.

Capacity of fermentor: 2 (L)
Effective volume of fermentor: 1.5 (L)
Separation membrane used: 22 polyvinylidene fluoride hollow fiber membranes (effective length: 8 cm, total effective membrane area: 0.023 m$^2$)

The number of hollow fiber membrane modules: 12, as shown in FIG. 4, three hollow fiber membrane modules were connected in series, and four lines of the modules were installed.

Temperature adjustment: 32 (° C.)
Quantity of airflow in fermentor: nitrogen gas 0.2 (L/min)
Agitation rate in fermentor: 600 (rpm)
pH Adjustment: adjusted to pH 6 by using 3NCa(OH)$_2$
Supply of culture medium for lactic acid: the quantity of liquid in the fermentor was controlled to be uniform approximately at 1.5 L and was added
Cross-flow flux by fermentation liquid circulating apparatus: 0.3 (m/s)
Controlling of flow rate of membrane filtration: flow rate was controlled by suctioning pump
Intermittent filtration treatment: cyclical operation of filtration treatment (for nine minutes) and suspension of filtration treatment (for nine minutes)
Membrane filtration flux: changeable so as to cause the transmembrane pressure difference to be equal to or less than 20 kPa within the range from 0.01 (m/day) to 0.3 (m/day). When the transmembrane pressure difference exceeded the range and continued to rise, continuous fermentation was ended.

A culture medium was used after being subjected to steam sterilization under saturated water vapor at the temperature of 121° C. for 20 minutes. *Sporolactobacillus laevolacticus* JCM2513 (SL root) was used as the microorganisms, a lactic acid fermentation culture medium having compositions shown in Table 1 was used as the culture medium, and evaluation of concentration of a lactic acid which was a product has been performed under the following conditions by using high performance liquid chromatography (HPLC) shown below.

TABLE 1

Lactic Acid Fermentation Culture Medium

| Component | Quantity |
| --- | --- |
| Glucose | 100 g |
| Yeast nitrogen base W/O amino acid (Difco Laboratories, Inc.) | 6.7 g |
| Standard amino acids excluding Leucine (19 types) | 152 mg |
| Leucine | 760 mg |
| Inositol | 152 mg |
| p-aminobenzoic acid | 16 mg |
| Adenine | 40 mg |
| Uracil | 152 mg |
| Water | 892 g |

Column: Shim-Pack SPR-H (manufactured by Shimadzu Corporation)
Moving phase: 5 mM p-toluene sulfonic acid (0.8 mL/min)
Reactional phase: 5 mM p-toluene sulfonic acid, 20 mM Bis-Tris, 0.1 mM EDTA.2Na (0.8 mL/min)
Detection method: electric conductivity
Column temperature: 45° C.

The analysis of optical purity of the lactic acid was performed under the following condition.

Column: TSK-gel Enantio L1 (manufactured by Tosoh Corporation)
Moving phase: 1 mM copper sulfate aqueous solution
Flux: 1.0 mL/min
Detection method: UV 254 nm
Temperature: 30° C.

The optical purity of the D-lactic acid was calculated using the following expression.

$$\text{Optical purity (\%)} = 100 \times (D-L)/(D+L)$$

Here, L represents the concentration of the L-lactic acid, and D represents the concentration of the D-lactic acid.

With regard to cultivation, first, an SL root was subjected to vibration cultivation one overnight in a lactic acid fermentation culture medium of 5 mL in a test tube (first preculture). The obtained cultivation liquid was inoculated with a fresh lactic acid fermentation culture medium of 100 mL, and was subjected to vibration cultivation for 24 hours at 30° C. in a Sakaguchi flask having capacity of 100 mL (second preculture). With regard to the cultivation liquid of the second preculture, the culture medium was input to the fermentor of 1.5 L of the membrane separation-type continuous-fermentation apparatus 103 illustrated in FIG. 4 and was inoculated. The fermentor 1 was agitated by the attached agitation device 4. Adjustment of the quantity of airflow, adjustment of the temperature, adjustment of the pH value were performed for the fermentor 1. Without operating the circulation pump 11, cultivation was performed for 24 hours (final preculture). Immediately after the completion of the final preculture, the circulation pump 11 was operated. In addition to the operational conditions at the time of the final preculture, continuous supply of the lactic acid fermentation culture medium was performed. Continuous cultivation was performed while controlling the amount of the membrane permeated water so as to cause the amount of the fermentation liquid in the continuous-fermentation apparatus to be 1.5 L, thereby manufacturing the D-lactic acid through continuous fermentation. With regard to controlling of the amount of the membrane permeated water when performing the continuous fermentation test, the filtration amount was controlled to be the same as the flow rate of supplying the fermentation culture medium by using the filtration pumps 121, 122, and 123 and the filtration control valves 131, 132, and 133. The concentration of the produced D-lactic acid in the membrane permeated fermentation liquid and the concentration of the remaining glucose were measured accordingly.

In the membrane separation-type continuous-fermentation apparatus 103, while performing the backwashing during the suspension of filtration treatment in the intermittent filtration treatment, continuous fermentation of the D-lactic acid was performed. In the intermittent filtration treatment, the separation membrane module parallel units PU1, PU2, and PU3 were disposed in accordance with the flow illustrated in FIG. 4, and the backwashing treatment was controlled so as to not be overlapped in the separation membrane module parallel units PU1, PU2, and PU3 with one another. In the intermittent filtration treatment, all the separation membrane modules were subjected to filtration treatment operation for two minutes, and only the separation membrane module parallel unit PU1 was subjected to the backwashing treatment for one minute. Thereafter, all the separation membrane modules were operated again for two minutes, and only the separation membrane module parallel unit PU2 was subjected to the backwashing treatment for one minute. All the separation membrane modules were operated again for two minutes, and only the separation membrane module parallel unit PU3 was subjected to the backwashing treatment for one minute. The intermittent filtration treatment was continuously repeated while performing continuous fermentation and the produced D-lactic acid was collected. The backwashing flux was set twice the filtration flux, and the backwashing was performed using distilled water.

Table 2 shows the result of the continuous fermentation test performed by the intermittent filtration treatment described above. In the membrane separation-type continuous-fermentation apparatus 103 illustrated in FIG. 4, continuous fermentation could be carried on for 400 hours, and the D-lactic acid production rate was 4.2 g/L/hr at the maximum. There was no rise of the transmembrane pressure difference and the operation could be stably performed.

Example 2

In Example 2, the separation membrane module parallel units PU1, PU2, and PU3 were simultaneously subjected to the suspension of filtration treatment of the intermittent filtration treatment in the membrane separation-type continuous-fermentation apparatus 103, and continuous fermentation for the D-lactic acid was performed while performing the backwashing during the suspension of the filtration treatment. In the intermittent filtration treatment, all the separation membrane modules were operated for two minutes. Thereafter, all the separation membrane modules were subjected to the backwashing treatment for one minute, and filtrating operation was performed again for all the separation membrane modules for six minutes. While performing continuous fermentation by continuously repeating the intermittent filtration treatment, the produced D-lactic acid was collected. Other conditions were the same as those in Example 1.

Table 2 shows the result of the continuous fermentation test performed by the intermittent filtration treatment described above. In the membrane separation-type continuous-fermentation apparatus 103 illustrated in FIG. 4, continuous fermentation could be carried on for 380 hours, and the D-lactic acid production rate was 4.0 g/L/hr at the maximum. There was no rise of the transmembrane pressure difference and the operation could be stably performed.

TABLE 2

|  | Example 1 | Example 2 |
|---|---|---|
| Fermentation period [hr] | 400 | 380 |
| Maximum D-lactic acid production rate [g/L] | 4.2 | 4.0 |

The present application is based on Japanese Patent Application No. 2013-130368 filed on Jun. 21, 2013, the contents of which is incorporated herein by reference.

INDUSTRIAL APPLICABILITY

According to a filtration device of the present invention, equipment can be shared among a plurality of separation membrane modules, a flow rate of cross-flow can be reduced as the separation membrane modules are disposed in series, and the equipment can be simplified.

DESCRIPTION OF REFERENCE NUMERALS AND SIGNS

1: FERMENTOR
A1, B1, C1, D1: SEPARATION MEMBRANE MODULE
A2, B2, C2, D2: SEPARATION MEMBRANE MODULE
A3, B3, C3, D3: SEPARATION MEMBRANE MODULE
E1, F1, G1, H1: SEPARATION MEMBRANE MODULE
E2, F2, G2, H2: SEPARATION MEMBRANE MODULE
E3, F3, G3, H3: SEPARATION MEMBRANE MODULE
3: TEMPERATURE CONTROL DEVICE
4: AGITATION DEVICE
5: pH SENSOR
6: LEVEL SENSOR
7: GAS SUPPLY DEVICE
8: WATER SUPPLY PUMP
9: CULTURE MEDIUM SUPPLY PUMP
10: pH ADJUSTER SUPPLY PUMP
11: CIRCULATION PUMP
121, 122, 123: FILTRATION PUMP
131, 132, 133: FILTRATION CONTROL VALVE
14: CLEANING LIQUID PUMP
151, 152, 153: CLEANING LIQUID VALVE
161, 162, 163: FILTRATION PUMP
171, 172, 173: FILTRATION CONTROL VALVE
181, 182, 183: CLEANING LIQUID VALVE
20: LIQUID SUPPLY LINE
21, 22, 23, 24: PIPE FOR LIQUID TO BE FILTRATED
40, 401: MEMBRANE CLEANING DEVICE
41, 42, 43, 44, 45, 46: PERMEATED LIQUID FLOW RATE SENSOR
51, 52, 53: FILTRATING OPERATION CONTROL DEVICE
60: REFLUX LINE
61, 62, 63, 64: CIRCULATION LIQUID PIPE

611, 612, 613: SERIES NON-PERMEATED LIQUID FLOW CHANNEL
501, 502, 503: CONTROL UNIT
101, 102, 103, 104: CONTINUOUS-FERMENTATION APPARATUS
201, 202, 203, 204, 205: FILTRATION DEVICE
PU1, PU2, PU3, PU4: SEPARATION MEMBRANE MODULE PARALLEL UNIT
SU1, SU2, SU3, SU4, SU11, SU12: SEPARATION MEMBRANE MODULE SERIES UNIT
a11, a12, a13, a14, a15, A1, A2, A3: HOLLOW FIBER MEMBRANE MODULE
a2: HOLLOW FIBER MEMBRANE
a2a: SMALL BUNDLE OF HOLLOW FIBER MEMBRANES
a3: CYLINDRICAL CASE
a41, a42: HOLLOW FIBER MEMBRANE BUNDLING MEMBER
a5: SMALL BUNDLE BLOCKING MEMBER
a6: UPPER CAP
a7: LOWER CAP
701, 702: ENTRANCE FOR LIQUID TO BE FILTRATED
701a, 702a: NOZZLE FOR LIQUID TO BE FILTRATED
711: EXIT FOR CONCENTRATED LIQUID
711a: CONCENTRATED LIQUID NOZZLE
80, 81: DRAINAGE DISCHARGE PORT
80a, 81a: DRAINAGE DISCHARGE NOZZLE
91, 92: EXIT FOR FILTRATED LIQUID
92a: FILTRATED LIQUID DISCHARGE NOZZLE

The invention claimed is:

1. A filtration device comprising a plurality of separation membrane modules each of which separates a liquid to be filtrated into a permeated liquid and a non-permeated liquid, wherein the filtration device comprises:
 a series non-permeated liquid flow channel that forms a plurality of series units by connecting non-permeation sides of the plurality of separation membrane modules in series; and
 a parallel permeated liquid flow channel that forms a parallel unit by connecting permeation sides of the plurality of separation membrane modules in parallel;
 wherein the parallel permeated liquid flow channel comprises a unit-crossing parallel flow channel that forms the parallel unit by connecting permeation sides of the plurality of separation membrane modules belonging to the series units different from one another in parallel,
 a filtrating operation control device disposed on the unit-crossing parallel flow channel and controls at least one of a filtration flow rate and a transmembrane pressure difference of the separation membrane modules by collectively controlling the pressures of the permeated liquids flowing out from the plurality of separation membrane modules belonging to the parallel unit.

2. The filtration device according to claim 1, wherein the filtrating operation control device collectively controls the pressures of the permeated liquids flowing out from the plurality of separation membrane modules which are included in the series units different from one another and are disposed in a same stage.

3. A filtration device comprising a plurality of separation membrane modules each of which separates a liquid to be filtrated into a permeated liquid and a non-permeated liquid, wherein the filtration device comprises:
 a series non-permeated liquid flow channel that forms a plurality of series units by connecting non-permeation sides of separation membrane modules in series; and
 a parallel permeated liquid flow channel that forms a parallel unit by connecting permeation sides of the plurality of separation membrane modules in parallel, and
 wherein the filtration device comprises, as the parallel permeated liquid flow channel, at least a unit-crossing parallel flow channel that connects the plurality of separation membrane modules belonging to the series units different from one another, and
 the filtration device further comprises a filtrating operation control device that controls at least one of a filtration flow rate and a transmembrane pressure difference of the separation membrane modules by collectively controlling pressures of the permeated liquids flowing out from the plurality of separation membrane modules belonging to the parallel unit and that is disposed on the unit-crossing parallel flow channel.

4. The filtration device according to claim 1, which comprises first and second parallel units, wherein the second parallel unit is disposed in a later stage than the separation membrane modules included in the first parallel unit.

5. The filtration device according to claim 3, which comprises first and second parallel units, wherein the second parallel unit is disposed in a later stage than the separation membrane modules included in the first parallel unit.

6. The filtration device according to claim 5, wherein the filtrating operation control device controls the pressures of the permeated liquids flowing out from the separation membrane modules so as to reduce a difference in the filtration flow rate between the separation membrane modules belonging to the first and second parallel units.

7. The filtration device according to claim 5, wherein the filtrating operation control device controls the pressures of the permeated liquids flowing out from the separation membrane modules so as to reduce a difference in the transmembrane pressure difference between the separation membrane modules belonging to the first and second parallel units.

8. The filtration device according to claim 3, further comprising a cleaning liquid supply unit that is connected to the parallel permeated liquid flow channel and supplies a cleaning liquid for backwashing.

9. The filtration device according to claim 1, comprising a plurality of the filtrating operation control devices.

10. The filtration device according to claim 3, comprising a plurality of the filtrating operation control devices.

11. The filtration device according to claim 1, wherein a longitudinal direction of the separation membrane module is perpendicular to or inclined with respect to a horizontal direction.

12. The filtration device according to claim 3, wherein a longitudinal direction of the separation membrane module is perpendicular to or inclined with respect to a horizontal direction.

13. The filtration device according to claim 1, which further comprises:
 a filtrating operation control device that controls at least one of a filtration flow rate and a transmembrane pressure difference of the separation membrane modules by collectively controlling pressures of the permeated liquids flowing out from the plurality of separation membrane modules,
 wherein the filtrating operation control device has, on the parallel permeated liquid flow channel, at least one of a permeated liquid flow rate sensor and a permeated liquid pressure sensor, and at least one of a filtration pump and a filtration control valve, and the filtrating operation control device further has a control unit which controls at least one of driving power of the filtration pump and a degree to which the filtration control valve is open based on an output result of the permeated liquid flow rate sensor or the permeated liquid pressure sensor.

* * * * *